(12) United States Patent
Bitner et al.

(10) Patent No.: US 8,658,360 B2
(45) Date of Patent: *Feb. 25, 2014

(54) NUCLEIC ACID PURIFICATION WITH A BINDING MATRIX

(75) Inventors: Rex M. Bitner, Cedarburg, WI (US); Michelle M. Mandreker, Oregon, WI (US); Paula R. Brisco, Oregon, WI (US)

(73) Assignee: Promega Corporation, Madison, WI (US)

( * ) Notice: Subject to any disclaimer, the term of this patent is extended or adjusted under 35 U.S.C. 154(b) by 99 days.

This patent is subject to a terminal disclaimer.

(21) Appl. No.: 13/223,904

(22) Filed: Sep. 1, 2011

(65) Prior Publication Data

US 2012/0059160 A1    Mar. 8, 2012

Related U.S. Application Data

(63) Continuation of application No. 11/636,174, filed on Dec. 8, 2006, now Pat. No. 8,030,034.

(60) Provisional application No. 60/748,825, filed on Dec. 9, 2005.

(51) Int. Cl.
    *C12Q 1/68* (2006.01)

(52) U.S. Cl.
    USPC .......................................................... 435/6.1

(58) Field of Classification Search
    None
    See application file for complete search history.

(56) References Cited

U.S. PATENT DOCUMENTS

| | | |
|---|---|---|
| 3,652,761 A | 3/1972 | Weetall |
| 3,897,309 A | 7/1975 | Grabner |
| 4,001,197 A | 1/1977 | Mitchell et al. |
| 4,059,512 A | 11/1977 | Harris |
| 4,224,413 A | 9/1980 | Burbidge |
| 4,233,169 A | 11/1980 | Beall et al. |
| 4,297,337 A | 10/1981 | Mansfield et al. |
| 4,298,500 A | 11/1981 | Abbott |
| 4,395,271 A | 7/1983 | Beall et al. |
| 4,491,660 A | 1/1985 | Gendrich et al. |
| 4,523,996 A | 6/1985 | Charles et al. |
| 4,661,260 A | 4/1987 | Kodama et al. |
| 4,661,407 A | 4/1987 | Henderson |
| 4,672,040 A | 6/1987 | Josephson |
| 4,683,202 A | 7/1987 | Mullis |
| 4,695,393 A | 9/1987 | Whitehead et al. |
| 4,699,717 A | 10/1987 | Riesner et al. |
| 4,743,545 A | 5/1988 | Torobin |
| 4,767,670 A | 8/1988 | Cox et al. |
| 4,808,314 A | 2/1989 | Karplus et al. |
| 4,861,705 A | 8/1989 | Margel |
| 4,866,034 A | 9/1989 | Ribi |
| 4,885,168 A | 12/1989 | Hashimoto et al. |
| 4,925,818 A | 5/1990 | Schneider et al. |
| 4,927,749 A | 5/1990 | Dorn |
| 4,927,750 A | 5/1990 | Dorn |
| 4,966,613 A | 10/1990 | Beaver |
| 5,057,426 A | 10/1991 | Henco et al. |
| 5,059,527 A | 10/1991 | White et al. |
| 5,075,430 A | 12/1991 | Little |
| 5,076,950 A | 12/1991 | Ullman et al. |
| 5,126,239 A | 6/1992 | Livak et al. |
| 5,155,018 A | 10/1992 | Gillespie et al. |
| 5,169,535 A | 12/1992 | Adachi et al. |
| 5,185,415 A | 2/1993 | Kawabata et al. |
| 5,234,809 A | 8/1993 | Boom et al. |
| 5,279,936 A | 1/1994 | Vorpahl |
| 5,316,680 A | 5/1994 | Frechet et al. |
| 5,346,994 A | 9/1994 | Chomczynski |
| 5,389,449 A | 2/1995 | Afeyam et al. |
| 5,395,498 A | 3/1995 | Gombinsky et al. |
| 5,401,415 A | 3/1995 | Rauh et al. |
| 5,403,917 A | 4/1995 | Boos et al. |
| 5,523,231 A | 6/1996 | Reeve |
| 5,561,064 A | 10/1996 | Marquet et al. |
| 5,563,068 A | 10/1996 | Zhang et al. |
| 5,576,185 A | 11/1996 | Coulter et al. |
| 5,582,988 A | 12/1996 | Backus et al. |
| 5,585,236 A | 12/1996 | Bonn et al. |
| 5,589,459 A | 12/1996 | Porro |
| 5,591,628 A | 1/1997 | Baek et al. |

(Continued)

FOREIGN PATENT DOCUMENTS

| | | |
|---|---|---|
| CA | 2223821 | 6/1996 |
| DE | 3935098 | 4/1991 |

(Continued)

OTHER PUBLICATIONS

Lin et al., "Chromatography of nucleic acids on polynucleotide-coated kieselguhr," Biochim. Et Biophys. Acta—Nucl. Acids and Prot Synth. (1970) 217(2):1 page, abstract.
United States Patent Office Action for U.S. Appl. No. 11/715,761 dated Apr. 18, 2012 (22 pages).
European Patent Office Examination Report for Application No. 06845029.5 dated Oct. 26, 2011 (7 pages).
Japanese Patent Office Action for Application No. 2009-053541 dated Sep. 1, 2011 (10 pages).
Xu et al. "Induction of B-A Transitions of Deoxyoligonucleotides by Multivalent Cations in Dilute Aqueous Solution" Biophysical Journal, vol. 65, dated Sep. 1993, 1039-1049.
European Patent Office Action for Application No. 07752594.7 dated Jun. 11, 2012 (4 pages).

(Continued)

*Primary Examiner* — Kenneth R. Horlick
*Assistant Examiner* — David Thomas
(74) *Attorney, Agent, or Firm* — Michael Best & Friedrich LLP

(57) ABSTRACT

The present invention relates to methods, kits, and compositions for generating purified RNA samples and purified DNA samples. In particular, the present invention provides methods for generating a purified RNA or DNA sample from a sample containing both DNA and RNA molecules using a binding matrix that preferentially binds DNA or RNA in the presence of an acidic dilution buffer, or using a binding matrix that comprises acid zeolites, as well as compositions and kits for practicing such methods.

15 Claims, 36 Drawing Sheets

(56) References Cited

U.S. PATENT DOCUMENTS

| | | |
|---|---|---|
| 5,610,274 A | 3/1997 | Wong et al. |
| 5,652,348 A | 7/1997 | Burton et al. |
| 5,658,548 A | 8/1997 | Padhye et al. |
| 5,660,984 A | 8/1997 | Davis et al. |
| 5,674,997 A | 10/1997 | Woodard et al. |
| 5,681,946 A | 10/1997 | Reeve |
| 5,683,875 A | 11/1997 | Lichtenwalter et al. |
| 5,693,785 A | 12/1997 | Woodard et al. |
| 5,728,822 A | 3/1998 | Macfarlane |
| 5,734,020 A | 3/1998 | Wong et al. |
| 5,747,663 A | 5/1998 | Colpan et al. |
| 5,783,686 A | 7/1998 | Gonzalez |
| 5,789,148 A | 8/1998 | Van Vlasselaer et al. |
| 5,792,651 A | 8/1998 | Colpan et al. |
| 5,808,041 A | 9/1998 | Padhye et al. |
| 5,861,315 A | 1/1999 | Nakahata |
| 5,898,071 A | 4/1999 | Hawins |
| 5,904,848 A | 5/1999 | Wong et al. |
| 5,945,525 A | 8/1999 | Uematsu et al. |
| 5,981,235 A | 11/1999 | Shultz et al. |
| 5,990,301 A | 11/1999 | Colpan et al. |
| 6,027,945 A | 2/2000 | Smith et al. |
| 6,045,697 A | 4/2000 | Girot et al. |
| 6,048,695 A | 4/2000 | Bradley et al. |
| 6,051,380 A | 4/2000 | Sosnowski et al. |
| 6,117,398 A | 9/2000 | Bienhaus et al. |
| 6,180,778 B1 | 1/2001 | Bastian et al. |
| 6,194,562 B1 | 2/2001 | Smith et al. |
| 6,218,531 B1 | 4/2001 | Ekenberg |
| 6,270,970 B1 | 8/2001 | Smith et al. |
| 6,284,470 B1 | 9/2001 | Bitner et al. |
| 6,310,199 B1 | 10/2001 | Smith et al. |
| 6,344,326 B1 | 2/2002 | Nelson et al. |
| 6,376,194 B2 | 4/2002 | Smith et al. |
| 6,506,559 B1 | 1/2003 | Fire et al. |
| 6,617,108 B1 | 9/2003 | Willson et al. |
| 6,656,587 B2 | 12/2003 | Johnson et al. |
| 6,670,332 B1 | 12/2003 | Wheeler |
| 6,673,631 B1 | 1/2004 | Terba et al. |
| 6,787,307 B1 | 9/2004 | Bitner et al. |
| 6,806,362 B2 | 10/2004 | Smith et al. |
| 6,914,137 B2 | 7/2005 | Baker |
| 6,919,175 B1 | 7/2005 | Bienhaus et al. |
| 6,992,182 B1 | 1/2006 | Muller et al. |
| 7,078,224 B1 | 7/2006 | Bitner et al. |
| 7,208,269 B2 | 4/2007 | Bavykin |
| 8,030,034 B2 * | 10/2011 | Bitner et al. ............. 435/91.5 |
| 2002/0004111 A1 | 1/2002 | Matsubara et al. |
| 2002/0162797 A1 | 11/2002 | Johnson et al. |
| 2002/0165388 A1 | 11/2002 | Bavykin et al. |
| 2003/0013112 A1 | 1/2003 | Sprenger |
| 2003/0096366 A1 | 5/2003 | Knudsen |
| 2003/0138828 A1 | 7/2003 | Bost et al. |
| 2004/0018559 A1 | 1/2004 | Lau et al. |
| 2004/0023273 A1 | 2/2004 | Puget et al. |
| 2004/0086930 A1 | 5/2004 | Terba et al. |
| 2004/0180445 A1 | 9/2004 | Domanico et al. |
| 2004/0258570 A1 | 12/2004 | Beebe et al. |
| 2005/0059024 A1 | 3/2005 | Conrad |
| 2005/0079535 A1 | 4/2005 | Kirchgesser et al. |
| 2005/0214926 A1 | 9/2005 | Zielenski et al. |
| 2005/0260625 A1 | 11/2005 | Wang |
| 2005/0282202 A1 | 12/2005 | Brolaski et al. |
| 2006/0240448 A1 | 10/2006 | Bitner et al. |
| 2007/0015191 A1 | 1/2007 | Bitner et al. |
| 2007/0087385 A1 | 4/2007 | Muller-Schulte |
| 2007/0249821 A1 | 10/2007 | Bitner et al. |
| 2012/0309952 A1 | 12/2012 | Bitner et al. |

FOREIGN PATENT DOCUMENTS

| | | |
|---|---|---|
| DE | 4307262 | 9/1994 |
| DE | 19512368 | 10/1996 |
| EP | 0162819 | 11/1985 |
| EP | 0184710 | 6/1986 |
| EP | 0230768 | 8/1987 |
| EP | 0245986 | 11/1987 |
| EP | 0343934 | 11/1989 |
| EP | 0391608 | 10/1990 |
| EP | 0741141 | 11/1996 |
| EP | 0757106 | 2/1997 |
| EP | 0875271 | 11/1998 |
| EP | 0992583 | 4/2000 |
| EP | 1479769 | 11/2004 |
| GB | 2074892 | 11/1981 |
| JP | 62151752 | 7/1987 |
| JP | 62235207 | 10/1987 |
| JP | 5504095 | 7/1993 |
| JP | 6126635 | 5/1994 |
| JP | 9-508406 | 8/1997 |
| JP | 9327290 | 12/1997 |
| JP | 9327291 | 12/1997 |
| JP | 10316696 | 12/1998 |
| WO | WO 83/03363 | 10/1983 |
| WO | WO 83/03920 | 11/1983 |
| WO | WO 88/06632 | 9/1988 |
| WO | WO 90/15666 | 12/1990 |
| WO | WO 91/05606 | 5/1991 |
| WO | WO 91/12079 | 8/1991 |
| WO | WO 95/06652 | 3/1995 |
| WO | WO 95/21177 | 8/1995 |
| WO | WO 95/21179 | 8/1995 |
| WO | WO 96/16186 | 5/1996 |
| WO | WO 96/18731 | 6/1996 |
| WO | WO 96/31781 | 10/1996 |
| WO | WO 96/36706 | 11/1996 |
| WO | WO 96/41811 | 12/1996 |
| WO | WO 97/29825 | 8/1997 |
| WO | WO 97/30152 | 8/1997 |
| WO | WO 97/32893 | 9/1997 |
| WO | WO 98/31461 | 7/1998 |
| WO | WO 98/31840 | 7/1998 |
| WO | WO 98/51435 | 11/1998 |
| WO | WO 98/51693 | 11/1998 |
| WO | WO 99/36359 | 7/1999 |
| WO | WO 99/54340 | 10/1999 |
| WO | WO 00/29562 | 5/2000 |
| WO | WO 00/69872 | 11/2000 |
| WO | WO 00/70040 | 11/2000 |
| WO | WO 00/70041 | 11/2000 |
| WO | WO 02/09125 | 1/2002 |
| WO | WO 02/38758 | 5/2002 |
| WO | WO 02/087871 | 11/2002 |
| WO | WO 03/046146 | 6/2003 |
| WO | WO 03/082892 | 10/2003 |
| WO | WO 2004/096984 | 11/2004 |
| WO | WO 2004/108741 | 12/2004 |
| WO | WO 2004/108925 | 12/2004 |
| WO | WO 2005/052581 | 6/2005 |
| WO | WO 2007/005613 | 1/2007 |
| WO | WO 2007/070381 | 6/2007 |
| WO | WO 2007/103485 | 9/2007 |
| WO | WO 2008/112015 | 9/2008 |
| WO | WO 2008/127356 | 10/2008 |

OTHER PUBLICATIONS

Japanese Patent Office Action for Application No. 2008558391 dated Jun. 15, 2012 (Original and English Translation 5 pages).

Advertisement, Promega Corporation Nucleic Acid purification products, "Having trouble seeing how to optimize your nucleic acid purification process?" Nature Biotechnology, vol. 19, No. 5, May 2001.

Advertisement, Wizard® Nucleic Acid Purification Systems, Science, vol. 282, Dec. 4, 1998. (Wizard® PureFection Plasmid DNA Purification System and PolyATtract® mRNA Isolation Systems) 2 pages.

Advertisement, Wizard® PureFection Plasmid DNA Purification System, Science, vol. 282, Oct. 30, 1998.

Aida, Y. et al., "Removal of endotoxin from protein solutiosn by phase separation using Triton X-114," J. Immunol Methods (1990) 132:191-195.

(56) References Cited

OTHER PUBLICATIONS

Anspach, F.B. "High performance liquid affinity chromatography with phenylboronic acid, benzamidine, tri-L-alanine, and concanavalin A immobilized on 3-isothiocyanatopropytriethoxysilane-activated nonporous monodisperse silicas," Anal. Biochem. (1989) 1797:171-181.

Anspach, F.B. et al., "Removal of endotoxins by affinity sorbents," J. Chrom. A (1995) 711:81-92.

Biocontrol Network, "Perma-guard diatomaceous earth," http://www.biconet.com (1998) 5 pages.

Bischoff, R. et al., "Chemically synthesized hydrophobig anion-exchange high-performance liquid chromatography supports used for oligonucleotide resolution by mixed mode chromatography," J. Chromatog. (1983) 270:117-126.

Bischoff, R. et al., "Nucleic acid resolution by mixed-mode chromatography," J. Chromatog (1984) 296:329-337.

Bitner R. et al., "Automation of DNA extraction from food and plants using MagneSil™ paramagnetic particles," Proceedings of SPIE V. 4264 (2001). Submitted Jan. 2001, Genomics & Proteomics Technologies, pp. 9-16.

Bitner, R et al., "Use of MagneSil paramagnetic particles for plasmid purification, PCR cleanup and purification of dideoxy and big dye DNA sequencing reactions," Advances in Nucleic Acid and Protein Analyses, Manipulation and Sequencing, Proceedings of SPIE (2000) 3926:126-133.

Boom, R. et al., "Rapid and simple method for purification of nucleic acids," J. Clin. Microbiol. (1990) 28:495-503.

Brisco, P. et al., "Use of a 96 well format for small scale mRNA isolation and cDNA synthesis," *Promega Notes Magazine*, No. 52, pp. 8-13 (1995).

Brown et al., "Anion-cation separations on a mixed bed alumina-sillica column," J. Chromatog. (1989) 466(1):291-300.

Brummelkamp et al., "A system for stable expression of short interfering RNAs in mammalian cells," Science (2002) 296:550-553.

Burke, P., "PolyATtract® mRNA isolation systems," *Promega Notes Magazine*, No. 56, p. 27-29 (1996).

Caplen, N. et al., "Specific inhibition of gene expression by small double-stranded RNAs in invertebrate and vertebrate systems," Proc. Natl. Acad. Sci. USA (2001) 98(17):9742-9747.

Controlled Pore Glass Products, CPG, Inc., Online, http://www.cpg-biotech.com (2002).

Cotten, M. et al., "Lipopolysaccharide is a frequent contaminant of plasmid DNA preparations and can be toxic to primary human cells in the presence of adenovirus," Gene Therapy (1994) 1:239-246.

Creswell, D., et al., "Increasing yield with the Wizard® PureFection Plasmid DNA Purification System," *Promega Notes Magazine*, No. 73 pp. 17-19 (1999).

Crowther, J.B. et al., "High-performance liquid chromatographic separation of oligonucleotides and other nucleic acid costituents on multifunctional stationary phases," J. Chromatog (1983) 282:619-628.

Davis, H.L. et al., "Direct gene transfer into skeletal muscle in vivo: factors affecting efficiency of transfer and stability of expression," Human Gene Ther. (1993) 4:151-159.

Edwardson, P.A.D. et al, "Separation and purification of oligonucleotides using a new bonded-phase packing material," J. Chromatog. (1991) 545:79-89.

Elbashir, S.M. et al., "Duplexes of 21-nucleotide RNAs mediate RNA interference in cultured mammalian cells," Nature (2001) 411:494-498.

Elbashir, S.M. et al., "Functional anatomy of siRNAs for mediating efficient RNAi in *Drosophila melanogaster* embryo lysate," EMBO J. (2001) 20(23):6877-6888.

Elbashir, S.M. et al., "RNA interference is mediated by 21- and 22-nucleotide RNAs," Genes & Dev. (2001) 15:188-200.

Ennifar, E. et al., "A crystallographic study of the binding of 13 metal ions to two related RNA duplexes," Nucl. Acids Res. (2003) 31(10):2671-2682.

Figueroa, A. et al., "High-performance immobilized-metal affinity chromatography of proteins on iminodiacetic acid silica-based bonded phases," J. Chromatog. (1986) 371:335-352.

Floyd, T.R. et al., "Mixed-mode hydrophobic ion exchange for the separation of oligonucleotides and DNA fragments using HPLC," Analytical Biochemistry (1986) 154:570-577.

Ford, The University of Edinburgh, U.K., Welcome to the Biology Teaching Organisation, see glossary definition of "lysis," web published with last update of Nov. 19, 1997, originally published at http://www.icmb.edinburgh.ac.uk.bto/glossary (site is archived and is not presently active) 3 pages.

Gjerd, D.T. et al., Ion chromatography, Ch. 3, Dr. Alfred Hothig Verlag Heidelberg (1987) 2nd Edition, 3 pages.

Goldsborough, M.D. et al., "High purity plasmid DNA from anion exchange chromatography," Focus (1998) 20(3):68-69.

Harkins, W.D. et al., Proceedings of the National Academy of Sciences of the United States of America (1916) 2(10):599-600, http://www.jstor.org/stable/83481.

Hirabayashi, J., "Applied slalom chromatography improved DNA separation by the use of columsn developed for reversed-phase chromatography," J. Chrom. (1996) 722:135-142.

Holen, T. et al., "Positional effects of short interfering RNAs targeting the human coagulation trigger tissue factor," Nucl. Acids Res. (2002) 30(8):1757-1766.

Jost, W. et al., "Application of a weekly basic dimethylamino-modified silica ion exchanger to the separation of oligonucleotides," J. Chromatog. (1979) 185:403-412.

Karplus, T.E. et al., "A new method for reduction of endotoxin contamination from protein solutions," J. Immunol Met. (1987) 105:211-220.

Kephart, D., "Rapid isolation of RNA from small quantities of human whole blood for use in RT-PCR analysis," *Promega Notes Magazine*, No. 62 pp. 11-16 (1997).

Kieft, J.S. et al., "Solution structure of a metal-binding site in the major groove of RNA complexed with cobalt (III) hexammine," Structure (1997) 5(5):713-721.

Kirk-Othmer Encyclopedia of Chemical Technology, vol. 21, 4th Edition, Mary Howe-Grant, Ed., John Wiley & Sons (1997) p. 1020-1023.

Kirk-Othmer Encyclopedia of Chemical Technology, vol. 6, 4th ed., John Wiley & Sons (1993) pp. 773-775.

Kleiber, J. et al., Database CAS online AN 126:86772 9 pp. Abstract, 1 page.

Krizova, J. et al., "Magnetic hydrophilic methacrylate-based polymer microspheres for genomic DNA isolation," J. Chromatog. A (2005) 1064:247-253.

Lepinski, M., "Tips for working with RNA and troubleshooting downstream applications," *Promega Notes Magazine*, No. 63 pp. 17-20 (1997).

Levison, P.R. et al., "New approaches to the isolation of DNA by ion-exchange chromatography," J. Chromat. (1998) 827(2):337-344.

Little, E.L. et al., "Sequential multimodal elution for pseudomultidimensional liquid chromatography on a single column," Anal. Chem. (1991) 63:33-44.

Liu, S. et al., "Removal of endotoxin from recombinant protein preparations," Clin. Biochem. (1997) 30(6):455-463.

Livage, J. et al. "Encapsulation of biomolecules in silica gels," J. Phys.: Condens. Matter (2001) 13:R673-691.

Maa, Y.F. et al., "Rapid high-performance liquid chromatography of nucleic acids with polystyrene-based micropellicular anion exchangers," J. Chromatog. (1990) 508:61-73.

Macherey-Nagel, homepage on the Internet on Jun. 12, 1998 at http://www.machrey-nagel.com, 3 pages.

Manthorpe, M. et al., "Gene therapy by intramuscular injection of plasmid DNA: studies on firefly luciferase gene expression in mice," Human Gene Therapy (1993) 4:419-431.

Marko, M.A. et al., "A procedure for the large-scale isolation of highly purified plasmic DNA using alkalilne extraction and binding to glass powder," Anal. Biochem. (1982) 121:382-287.

Marvin, H.J.P. et al., "Release of outer membrane fragments from wild-type *Escherichia coli* and from several *E coli* lipopolysaccharide mutants by EDTA and heat shock treatments," J. Bacter. (1989) 171(10):5262-5267.

(56) References Cited

OTHER PUBLICATIONS

McElroy et al., "QSAR and classification of murine and human soluble epoxide hydrolase inhibition by urea-like compounds," J. Med. Chem. (2003) 46(6):1066-1080.
McLaughlin, L., "Mixed-mode chromatography of nucleic acids," Chem. Rev. (1989) 89:309-319.
Molvig, J. et al., "Removal of endotoxin from culture media by a polymyxin B sepharose column," Scand. J. Immunol (1987) 26:611-619.
Montbriand, P.M. et al., "Improved method for the removal of endotoxin from DNA," J. Biotech. (1996) 44:43-46.
Morrison, D.C. et al., "Endotoxin and disease mechanisms," Ann. Rev. Med. (1987) 38:417-432.
Murphy, J.C. et al., "RNA isolation and fractionation with compaction agents," Anal. Biochem. (2001) 295:143-148.
Neri, B.P., et al., "Transferring automation for large-scale development and production of invader SNP assays," Abstract, BIOS (2000) 2 pages.
Northrop, D.M. et al., "Preparation and evaluation of a bimodal size-exclusion chromatography column containing a mixture of two silicas of different pore diameter," Anal. Chem. (1991) 63:1350-1354.
Osorio, C.R. et al., "Characterization of the 23S and 5S rRNA genes and 23S-5S intergenic spacer region (ITS-2) of *Photobacterium damselae*," Dis. Squat. Org. (2004) 61:33-39.
PerSeptive Diagnostics Product Guide for BioMag® Mini-Prep DNA Purification Kit (Catalog No. 8-MB4008K) Feb. 27, 1995 (4 pages).
Promega Corporation—1994-95 Biologic Research Products Catalog, front cover, table of contents, pp. 155-157 (1994) PolyATtract® mRNA Isolation Systems, PolyATtract® System 1000 Magnetic Separation Stand & MagneSphere™ Technology Magnetic Separation Stand, 5 pages.
Promega Corporation—"Material Safety Data Sheet: Wizard SV96 Neutralization Solution" http://www.promega.com/msds/uk/ukmsds\A148.htm, (Jul. 3, 2002) *Box 2 (composition/data on components):guanidinium chloride*, 1-5 pages.
Promega Corporation—"Wizard SV96 Plasmid DNA Purification System" (1999) Retrieved from the Internet on Sep. 5, 2007 (http://www.promega.co.jp/jp/jp_tech/jp_manuals/wsv96.pdf) pp. 1-9.
Promega Corporation—"Frequently asked questions of Promega's Technical Services Department," *Promega Notes*, No. 71, pp. 24-26 (1999).
Promega Corporation—1990-91 Product Catalogue, front and back cover, pp. 121-122 (1990) (PolyATtract™ mRNA Isolation Systems) 4 pages.
Promega Corporation—1991-92 Product Catalogue, front cover, first page of table of contents, pp. 192 and 348 (1991) (PolyATtract™ mRNA Isolation Systems & MagneSphere™ Technology Magnetic Separation Stand) 4 pages.
Promega Corporation—1992-93 Biologic Research Products Catalogue, front and back cover, first page of table of contents, pp. 161-163 (1992) (PolyATtract® mRNA Isolation Systems, PolyATtract® System 1000 Magnetic Separation Stand & MagneSphere™ Technology Magnetic Separation Stand) 6 pages.
Promega Corporation—1993-94 Product Catalog, front and back cover, first page of table of contents, pp. 149-151 (1993) (PolyATtract® mRNA Isolation Systems, PolyATtract® System 1000 Magnetic Separation Stand & MagneSphere™ Technology Magnetic Separation Stand) 5 pages.
Promega Corporation—1996 Biologic Research Products Catalog, front cover, table of contents, pp. 158-161 (1995) (PolyATtract® mRNA Isolation Systems, PolyATtract® System 1000 Magnetic Separation Stan, PolyATtract® Series 9600™ Multi-Magnet & MagneSphere™ Technology Magnetic Separation Stand) 6 pages.
Promega Corporation—1997 Biologic Research Products Catalog, front cover, table of contents, pp. 187-188 (1996) (PolyATtract® mRNA Isolation Systems, PolyATtract® System 1000 Magnetic Separation Stand, PolyATtract® Series 9600™ Multi-Magnet & MagneSphere™ Technology Magnetic Separation Stand) 5 pages.
Promega Corporation—1998 Biologic Research Products Catalog, cover and pp. 182-183 and 199-200, 5 pages.
Promega Corporation—1998 Biologic Research Products Catalog, front cover, table of contents, pp. 196-200 (1997) (PolyATtract® mRNA Isolation Systems, PolyATtract® System 1000 Magnetic Separation Stand, PolyATtract® Series 9600™ Multi-Magnet & MagneSphere™ Technology Magnetic Separation Stand), 7 pages.
Promega Corporation—1999 Life Science Catalog, front cover, table of contents, pp. 9.4, 9.19-9.22 and 10.17 (1998) (Wizard® PureFection Plasmid DNA Purification System, PolyATtract® mRNA Isolation Systems, PolyATtract® System 1000 Magnetic Separation Stand, PolyATtract® Series 9600™ Multi-Magnet & MagneSphere™ Technology Magnetic Separation Stand), 8 pages.
Promega Corporation—2000 Life Science Catalog, front cover, table of contents, pp. 2.4 and 2.12-2.14 (1999) (Wizard PureFection Plasmid DNA Purification System, PolyATtract mRNA Isolation Systems, PolyATtract System 1000 Magnetic Separation Stand, PolyATtract Series 9600 Multi-Magnet and MagneSphere Technology Magnetic Separation Stand), 6 pages.
Promega Corporation—Higher Throughput Solutions Brochure, BR094, (Jun. 2000) 6 pages.
Promega Corporation—MagneSphere® Magnetic Separation Products Technical Bulletin, TB246 (Nov. 1996) 1-10.
Promega Corporation—MagneSphere® Magnetic Separation Products Technical Bulletin, TB246 (revised Mar. 2000) 1-12.
Promega Corporation—Nucleic Acid Purification Systems Brochure, BR081 (Feb. 1999) 11 pages.
Promega Corporation—PolyATtract® mRNA Isolation System Technical Manual, TM021 (Revised Feb. 2000) 1-12.
Promega Corporation—PolyATtract® mRNA Isolation System Technical Manual, TM021 (Revised Apr. 1995)1-11.
Promega Corporation—PolyATtract® mRNA Isolation System Technical Manual, TM021 (Revised May 2001) 1-12.
Promega Corporation—PolyATtract® mRNA Isolation System Technical Manual, TM021 (Revised Aug. 1998) 1-16.
Promega Corporation—PolyATtract® System 1000 Technical Manual, TM228 (Dec. 1992) 1-19.
Promega Corporation—PolyATtract® System 1000 Technical Manual, TM228 (Revised May 2001) 1-19.
Promega Corporation—PolyATtract® System 1000 Technical Manual, TM228 (Revised Dec. 1999) 1-24.
Promega Corporation—PolyATtract® System 1000 Technical Manual, TM228 (Revised Feb. 2000) 1-23.
Promega Corporation—PolyATtract® System 1000 Technical Manual, TM228 (Revised Feb. 1997) 1-19.
Promega Corporation—PolyATtract® System 1000 Technical Manual, TM228 (Revised Mar. 1995) 1-18.
Promega Corporation—PolyATtract® System 1000 Technical Manual, TM228 (Revised Apr. 1999) 1-23.
Promega Corporation—PolyATtract® System 1000 Technical Manual, TM228 (Revised Jun. 1997) 1-19.
Promega Corporation—PolyATtract® System 1000 Technical Manual, TM228 (Revised Jun. 1998) 1-23.
Promega Corporation—Technical Bulletin No. 202, "Wizard Plus Series 9600 DNA Purification System" (Sep. 1998) 18 pages.
Promega Corporation—Technical Bulletin No. 225, "Wizard Plus SV Minipreps DNA Purification System" (Sep. 1999) 14 pages.
Promega Corporation—Technical Bulletin No. 48, "SV Total RNA Isolation System" (1998), 28 pages.
Promega Corporation—Wizard® MagneSil™ Plasmid Purification System, TB286 (Nov. 2001) pp. 1-12.
Promega Corporation—Wizard MagneSil Tfx™ System, Technical Bulleting TB314, first printing (Oct. 2002) pp. 1-9.
Promega Corporation—Wizard® MagneSil™ Plasmid Purification System, Technical Bulletin TB286, First Printing (Feb. 2001) pp. 1-11.
Promega Corporation—Wizard® Magnetic DNA Purification System for Food Technical Bulletin, TB284 (Aug. 2000) (PolyATtract® System 1000 Magnetic Separation Stand, Cat. #Z5410), pp. 1-11.
Promega Corporation—Wizard® Magnetic DNA Purification System for Food Technical Bulletin, TB284 (Revised Mar. 2001) (PolyATtract® System 1000 Magnetic Separation Stand, Cat. #Z5410), pp. 1-13.

(56) References Cited

OTHER PUBLICATIONS

Promega Corporation—Wizard® Magnetic DNA Purification System for Food Technical Bulletin, TB284 (Revised May 2001) (PolyATtract® System 1000 Magnetic Separation Stand, Cat. #Z5410), pp. 1-14.
Promega Corporation—Wizard® PureFection Plasmid DNA Purification Brochure, BR076 (Feb. 1999), pp. 1-9.
Promega Corporation—Wizard® PureFection Plasmid DNA Purification System Technical Bulletin, TB259 (Oct. 1998) pp. 1-14.
Promega Corporation—Wizard® PureFection Plasmid DNA Purification System Technical Bulletin, TB259 (Feb. 1999) pp. 1-14.
Promega Corporation—Wizard® PureFection Plasmid DNA Purification System, Neural Notes, vol. 4, Issue 2 (1998) p. 14.
Promega Corporation—Wizard® Purification Systems Brochure, BR072 (Jul. 1998) pp. 1-7.
QIAGEN Plasmid Purification Handbook (Jan. 1997) 67 pages.
Quantiblot, Quantiblot Human DNA Quantitation System, PE Applied Biosystems, Feb. 5, 1996, p. 1-5 (http://www.pebio.com/fo/773503/773503.html).
Rassi, Z.E. et al., "Tandem columns and mixed-bed columns in high-performance liquid chromatography of proteins," J. Chrom. (1986) 359:255-264.
Sambrook, J. et al., Molecular Cloning A Laboratory Manual, 2nd Edition, Cold Spring Harbor Laboratory Press (1989) 1.21-1.52.
Sambrook, J. et al., Molecular Cloning A Laboratory Manual, 2nd edition, Cold Spring Harbor Laboratory Press (1989) p. 2.22 and filtration system reference.
Shiels, G, et al., MagneSil™ C'este Magnifique!, Promega Notes 79 (2001), 3 pages.
Sigma-Aldrich 1997 Catalog, cover and p. 448.
Smith, D. et al., "Automated purification of plasmid DNA using paramagnetic particles," JALA V.8(3) pp. 50-54 (Jun. 2003).
Tuschl, T. et al., "Small interfering RNAs: a revolutionary tool for the analysis of gene function and gene therapy," A Role for siRNAs in Genetic Therapy, Molecular Interventions (2002) 2(3):158-167.
Uematsu et al., Database CAS online AN 126:182277, Abstract (EP0757106A2) (Jan. 21, 1997).
Vogelstein et al., "Preparative and analytical purification of DNA from Agarose," PNAS (1979) 76(2):615-619.
Waterborg et al., "Efficient large-scale purification of restriction fragments by solute-displacement ion-exchange HPLC," Nucleic Acids Res. (1993) 21(12):2913-2915.
Weber et al., "Effects of lipopolysaccharide on transfection efficiency in eukaryotic cells," Biotechniques (1995) 19(6):930-940.
Wheatley, J.B., "Multiple ligand applications in high-performance immunoaffinity chromatography," J. Chromatogr. (1992) 603:273.
White, D., et al., "Automated purification of transfection-grade plasmid DNA using Wizard MagneSil Tfx System," JALA, v. 8(4), pp. 50-53 (2003).
White, D., et al., "Be a 'Wizard' at transfection," Promega Notes 83 (2003) pp. 18-20.
White, D., et al., "Cells to Gels: Automated purification of plasmid DNA directly from bacterial culture with normalization," Promega Notes, No. 85 (2003) pp. 28-30.
White, D., et al., MagneSil™ paramagnetic particles: Novel magnetics for DNA purification, Promega Notes, No. 69 (1998) pp. 12-15.
White, D., et al., Wizard® PureFection plasmid DNA purification system: The new standard in isolating transfection grade plasmid DNA, Promega Notes, No. 68 (1998) pp. 2-9.
Wicks et al., "Bacterial lipopolysaccharide copurifies with plasmid DNA: implications for animal models and human gene therapy," Human Gene Therapy (1995) 6:317-323.
Wolfe, K.A. et al., "Toward a microchip-based solid-phase extraction method for isolation of nucleic acids," Electrophoresis (2002) 23(5):727-733.
Australian Patent Office Action for Application No. 2002225942 dated Feb. 24, 2006 (3 pages).
Australian Patent Office Action for Application No. 2002225942 dated Mar. 27, 2007 (2 pages).
Australian Patent Office Action for Application No. 23981/00 dated Oct. 9, 2003 (2 pages).
Canadian Patent Office Action for Application No. 2372054 dated Nov. 5, 2007 (2 pages).
Canadian Patent Office Action for Application No. 2372054 dated Oct. 30, 2009 (2 pages).
Canadian Patent Office Action for Application No. 2,372,485 dated Nov. 14, 2006 (6 pages).
Canadian Patent Office Action for Application No. 2372485 dated Oct. 30, 2009 (3 pages).
Canadian Patent Office Action for Application No. 2372485 dated Dec. 16, 2010 (1 page).
Canadian Patent Office Action for Application No. 2329067 dated Nov. 8, 2002 (2 pages).
Canadian Patent Office Action for Application No. 2329067 dated Mar. 20, 2002 (2 pages).
Canadian Patent Office Action for Application No. 2428532 dated Aug. 9, 2006 (3 pages).
Canadian Patent Office Action for Application No. 2428532 dated Sep. 4, 2007 (2 pages).
European Patent Office Action for Application No. 01993684.8 dated Aug. 5, 2005 (3 pages).
European Patent Examination Report for Application No. 99918650.5 dated Feb. 12, 2008 (9 pages).
European Patent Supplementary Search Report for Application No. 99918650.5 dated Oct. 12, 2004 (3 pages).
European Patent Office Action for Application No. 99967755.2 dated Jan. 17, 2007 (4 pages).
European Patent Office Action for Application No. 99967755.2 dated Oct. 28, 2004 (3 pages).
European Patent Office Search Report for Application No. 05017048.9 dated Apr. 9, 2008 (2 pages).
European Patent Office Search Report for Application No. 05017048.9 dated Dec. 15, 2005 (9 pages).
European Patent Office Action for Application No. 99967755.2 dated May 27, 2010 (5 pages).
European Patent Extended Search Report for Application No. 06785973.6 dated Mar. 4, 2010 (8 pages).
European Patent Supplementary Search Report for Application No. 06845029.5 dated Nov. 3, 2009 (8 pages).
European Patent Office Action for Application No. 07752594.7 dated Feb. 3, 2010 (5 pages).
European Patent Office Action for Application No. 07752594.7 dated Apr. 26, 2010 (6 pages).
Japanese Patent Office Action for Application No. 2000618288 dated Apr. 20, 2009 (15 pages) with English translation.
Japanese Patent Office Action for Application No. 2000618446 dated Dec. 24, 2009 (5 pages) with English translation.
Japanese Patent Office Action for Application No. 2000618446 dated Jul. 25, 2007 (5 pages).
Japanese Patent Office Action for Application No. 2000618446 dated Sep. 10, 2008 (8 pages).
Japanese Patent Office Action for Application No. 2000544678 dated Nov. 5, 2009 (6 pages) with English translation.
Japanese Patent Office Action for Application No. 2000544678 dated Feb. 16, 2009 (10 pages) with English translation.
Japanese Patent Office Action for Application No. 2002542074 dated Sep. 20, 2007 (7 pages).
International Search Report for Application No. PCT/US99/031207 dated Sep. 9, 2000 (2 pages).
Written Opinion for Application No. PCT/US99/031207 dated Jun. 2, 2001 (11 pages).
International Search Report for Application No. PCT/US99/08491 dated Jun. 7, 1999 (3 pages).
Written Opinion for Application No. PCT/US99/08491 dated Mar. 30, 2000 (7 pages).
International Preliminary Examination Report for Application No. PCT/US99/08491 dated Aug. 22, 2000 (5 pages).
International Search Report for Application No. PCT/US00/12186 dated Nov. 30, 2000 (4 pages).
International Preliminary Examination Report for Application No. PCT/US00/12186 dated Aug. 17, 2001 (5 pages).

(56) References Cited

OTHER PUBLICATIONS

International Search Report for Application No. PCT/US01/046710 dated Mar. 21, 2002 (4 pages).
International Preliminary Examination Report for Application No. PCT/US01/046710 dated Oct. 17, 2003 (3 pages).
International Search Report for Application No. PCT/US2006/025592 dated Aug. 3, 2007 (1 page).
Written Opinion for Application No. PCT/US2006/025592 dated Aug. 3, 2007 (4 pages).
International Search Report and Written Opinion for Application No. PCT/US2006/046879 dated Feb. 21, 2008 (9 pages).
International Search Report and Written Opinion for Application No. PCT/US2007/005906 dated Nov. 30, 2007 (9 pages).
United States Patent Office Action for U.S. Appl. No. 09/475,958 dated Aug. 8, 2001 (7 pages).
United States Patent Office Action for U.S. Appl. No. 09/475,958 dated Apr. 5, 2002 (12 pages).
United States Patent Office Action for U.S. Appl. No. 09/475,958 dated Nov. 13, 2003 (14 pages).
United States Patent Office Action for U.S. Appl. No. 09/475,958 dated Aug. 11, 2004 (17 pages).
United States Patent Office Action for U.S. Appl. No. 09/645,133 dated Nov. 2, 2000 (5 pages).
United States Patent Office Action for U.S. Appl. No. 11/319,146 dated Aug. 9, 2007 (9 pages).
United States Patent Office Action for U.S. Appl. No. 11/319,146 dated Mar. 25, 2008 (8 pages).
United States Patent Office Action for U.S. Appl. No. 11/319,146 dated Sep. 5, 2008 (11 pages).
United States Patent Office Action for U.S. Appl. No. 11/319,146 dated May 1, 2009 (7 pages).
United States Patent Office Action for U.S. Appl. No. 09/312,172 dated Apr. 12, 2000 (6 pages).
United States Patent Office Action for U.S. Appl. No. 09/312,172 dated Nov. 21, 2000 (5 pages).
United States Patent Office Action for U.S. Appl. No. 09/064,449 dated Dec. 7, 1999 (11 pages).
United States Patent Office Action for U.S. Appl. No. 09/064,449 dated May 27, 1999 (6 pages).
United States Patent Office Action for U.S. Appl. No. 09/711,782 dated Jul. 8, 2002 (11 pages).
United States Patent Office Action for U.S. Appl. No. 09/711,782 dated Nov. 25, 2002 (7 pages).
United States Patent Office Action for U.S. Appl. No. 09/711,782 dated Apr. 1, 2003 (8 pages).
United States Patent Office Action for U.S. Appl. No. 11/477,491 dated Aug. 8, 2008 (19 pages).
United States Patent Office Action for U.S. Appl. No. 11/477,491 dated Feb. 26, 2009 (8 pages).
United States Patent Office Action for U.S. Appl. No. 11/477,491 dated Jun. 2, 2009 (3 pages).
United States Patent Office Action for U.S. Appl. No. 11/477,491 dated Sep. 18, 2009 (19 pages).
United States Patent Office Action for U.S. Appl. No. 11/477,691 dated Jun. 29, 2010 (20 pages).
United States Patent Office Action for U.S. Appl. No. 11/477,691 dated Oct. 7, 2010 (4 pages).
United States Patent Office Action for U.S. Appl. No. 11/636,174 dated Dec. 28, 2009 (12 pages).
United States Patent Office Action for U.S. Appl. No. 11/636,174 dated May 28, 2009 (13 pages).
United States Patent Office Action for U.S. Appl. No. 11/636,174 dated Sep. 15, 2010 (13 pages).
United States Patent Office Notice of Allowance for U.S. Appl. No. 11/636,174 dated May 31, 2011 (6 pages).
United States Patent Office Action for U.S. Appl. No. 11/715,761 dated Oct. 21, 2009 (13 pages).
United States Patent Office Action for U.S. Appl. No. 11/715,761 dated Jul. 14, 2010 (18 pages).
Bergemann, C., et al., "Magnetic ion-exchange nano- and microparticles for medical, biochemical and molecular biological applications" Journal of Magnetism and Magnetic Materials 194 (1999) 45-52.
Brockhaus ABC Naturwissenschaft und Technik, 13th Edition, 1980, pp. 945 to 947.
Litopoulou-Tzanetaki, E., et al., "Adsorption of bacteria to ion-exchange materials" Letters in Applied Microbiology 1989. 9, 219-222.
Munaf, E., et al., "Microcolumn ion chromatography of inorganic anions using bovine serum albumin stationary phase with indirect photometric detection", Chromatographia vol. 43. No. 5/6. Sep. 1996.
Nesterenko et al. "Selectivity of chemically boned zwitterion-exchange stationary phases in ion chromatography". Journal of Chromatography A, 706 (1995) 59-68.
ROMPP Lexikon Chemie, 10th Edition, 1997, pp. 3588 to 3593.
ROMPP Lexikon Chemie, 10th Edition, 1997, pp. 1965 to 1967.
Wikipedia, "Albumin" article accessed on Jan. 16, 2012.
Wood, J. M., "The interaction of micro-organisms with ion exchange resins", Microbial Adhesion to Surfaces, 1980, Chapter 8.
United States Patent Office Action for U.S. Appl. No. 13/550,743 dated Jan. 16, 2013 (17 pages).
European Patent Office Examination Report for Application No. 07752594.7 dated Apr. 11, 2013 (4 pages).
"Viruses." (Wikipedia.com, accessed Nov. 24, 2012).
"How many species of bacteria are there" (wisegeek.com; accessed Sep. 23, 2011).
"Fungi," (Wikipedia.com; accessed Jun. 3, 2013).
"Plant," (Wikipedia.com; accessed Mar. 8, 2013).
"Mammal," (Wikipedia.com; accessed Sep. 22, 2011 ).
"Murinae," (Wikipedia.com, accessed Mar. 18, 2013).
United States Patent Office Action for U.S. Appl. No. 11/319,146 dated Sep. 27, 2013 (22 pages).

* cited by examiner

FIGURE 1
1A.
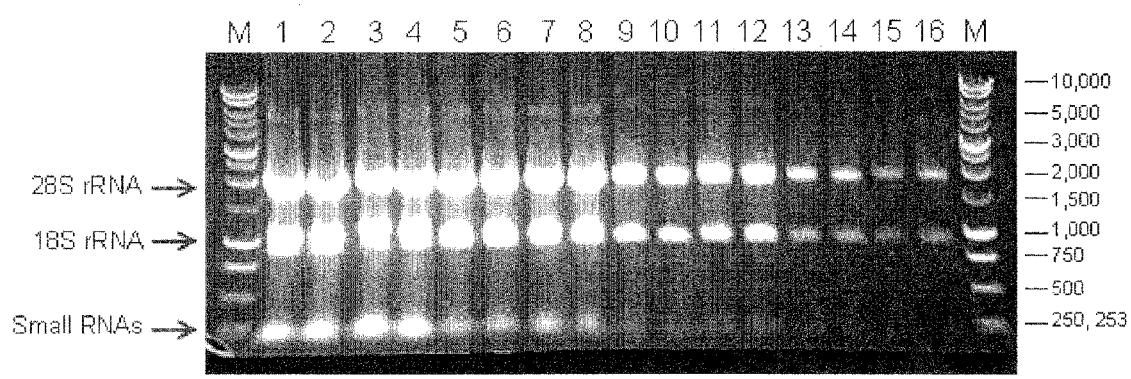
1B.
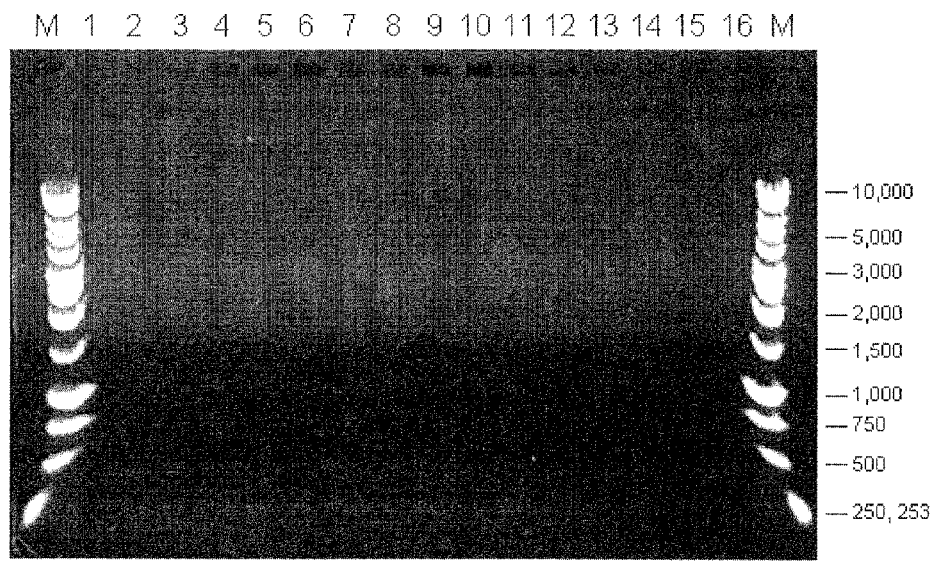

FIGURE 2
2A.
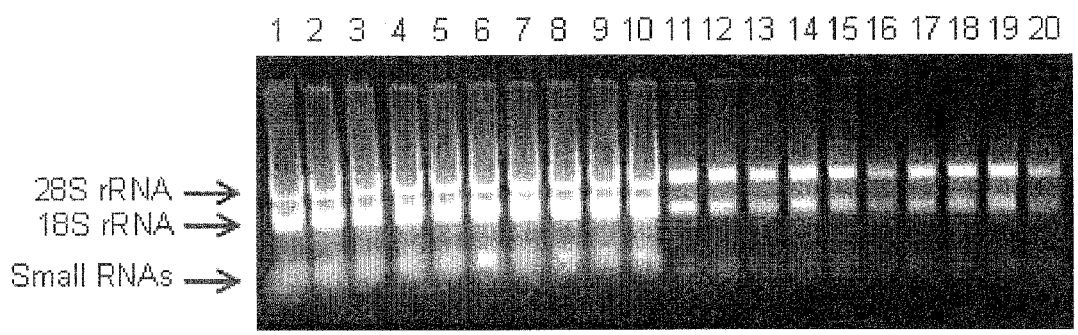
2B.
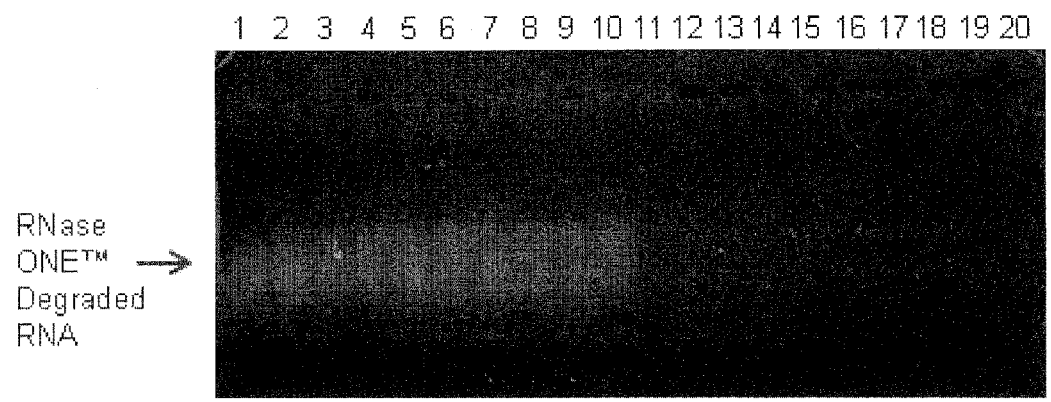

FIGURE 3
3A.
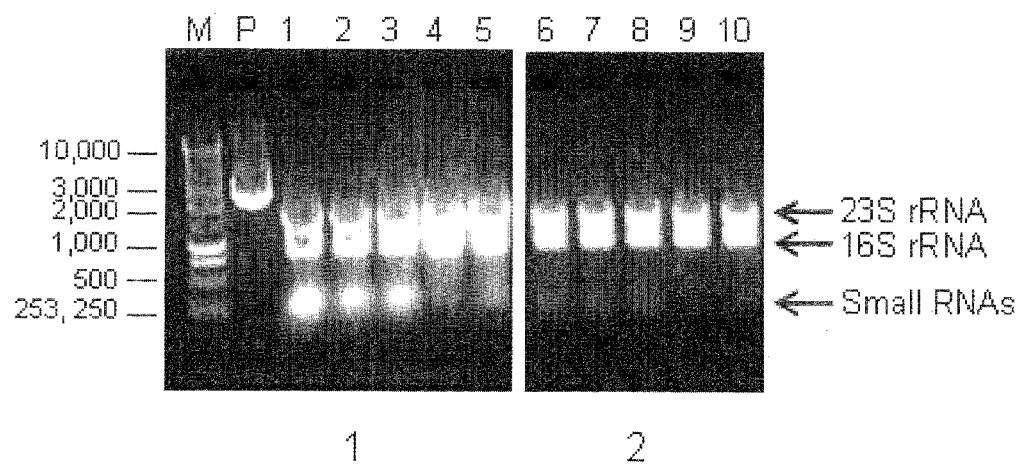
3B.
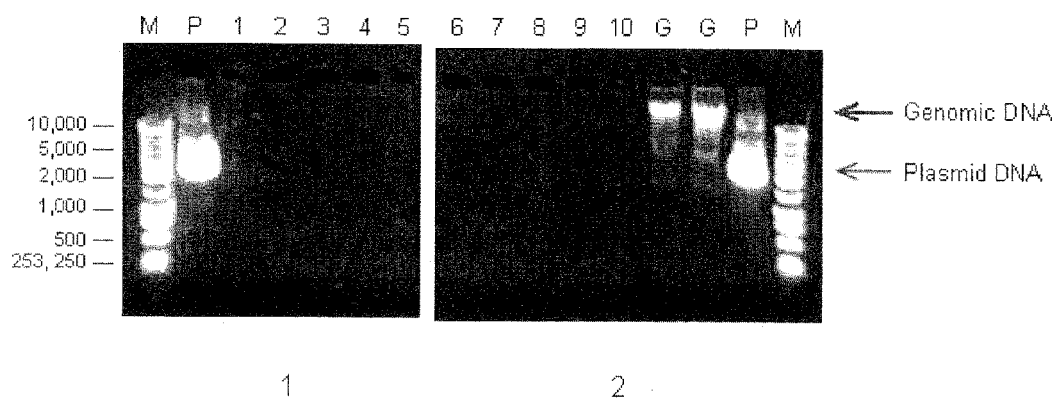

FIGURE 4
4A.
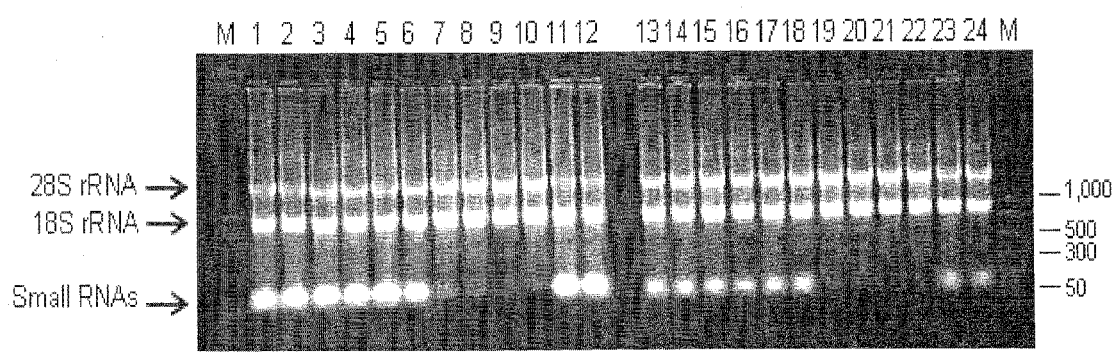
4B.
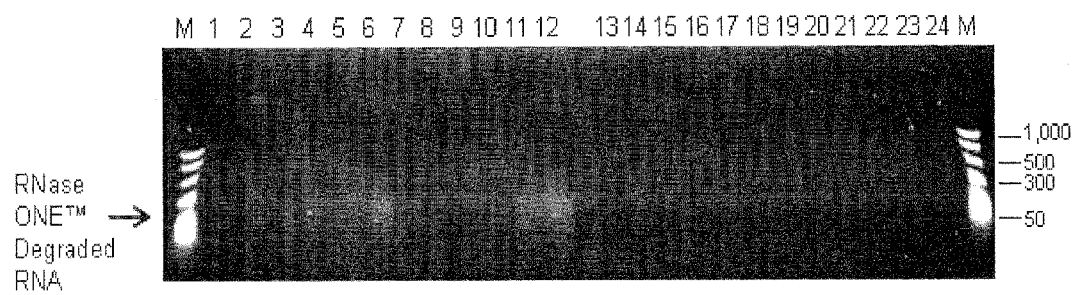

FIGURE 5
5A.
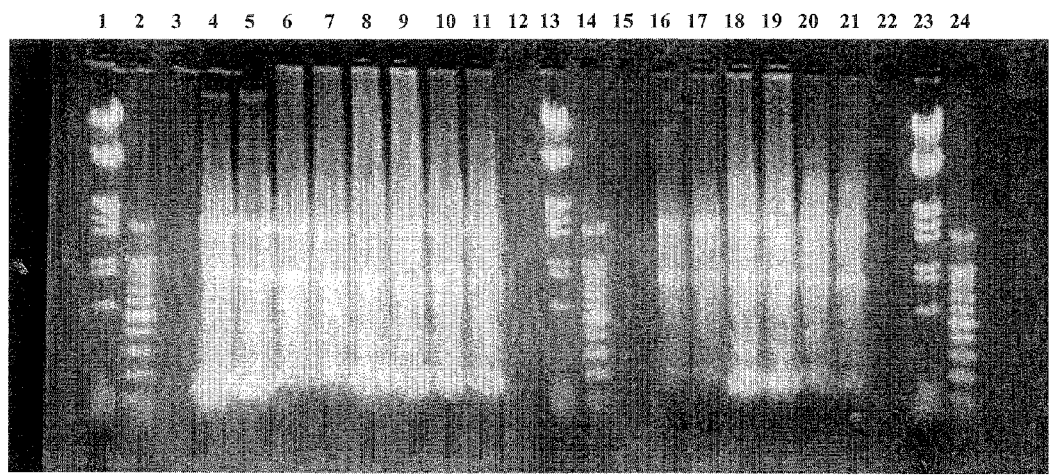
5B.
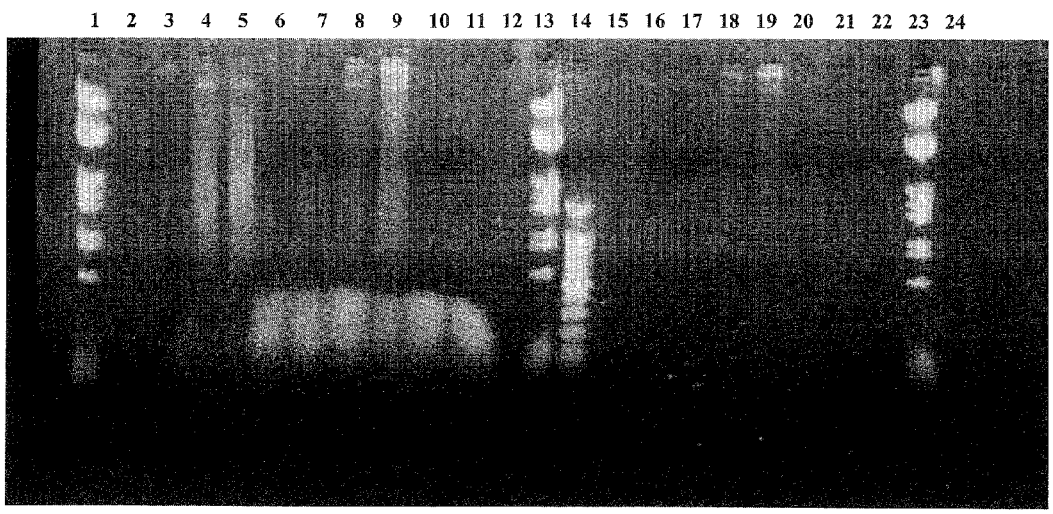

FIGURE 7
7A.
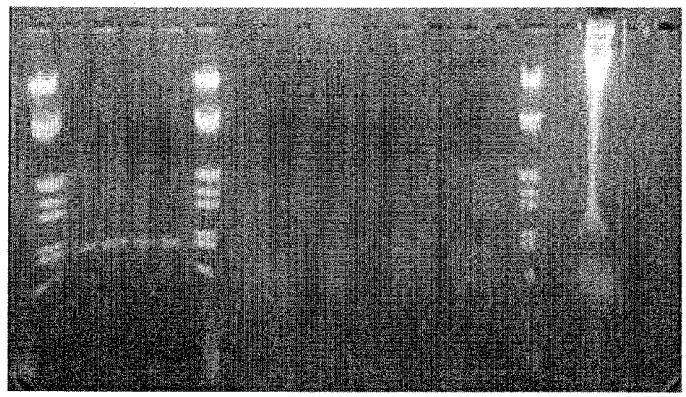
7B.
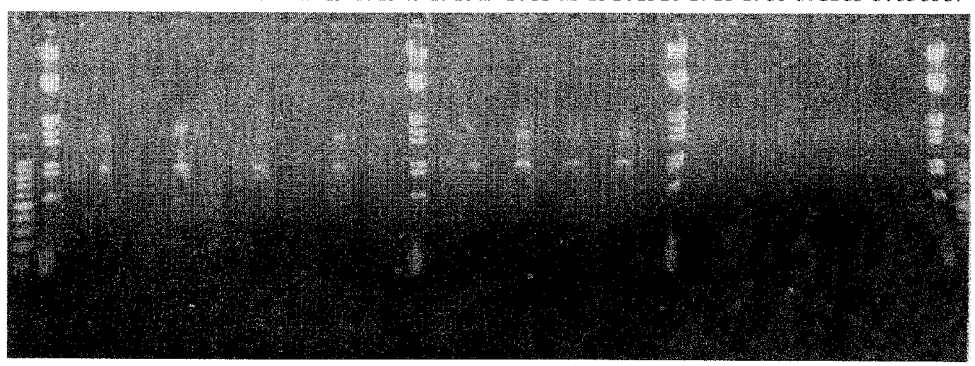
7C.

FIGURE 9
A.
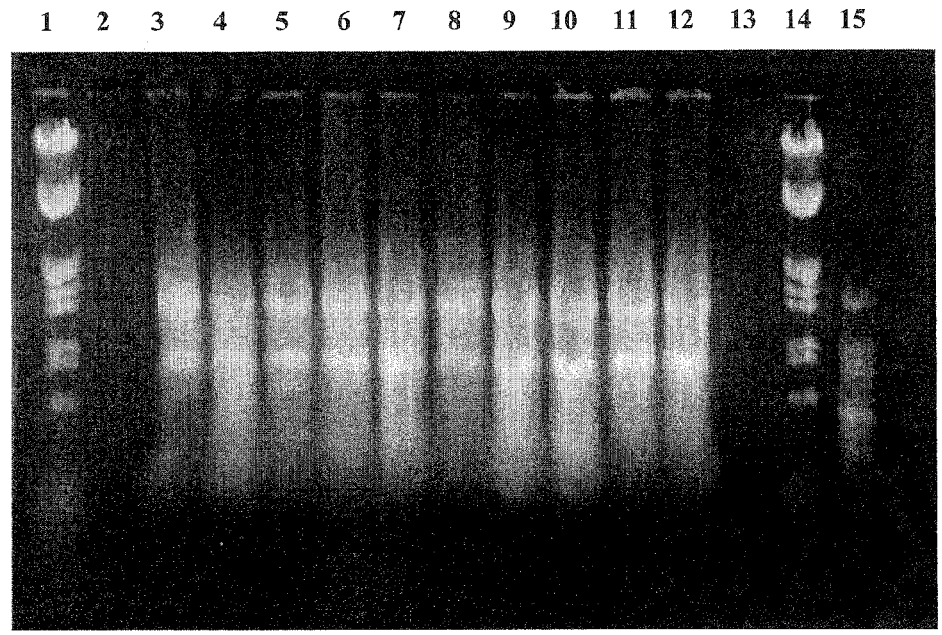
B.
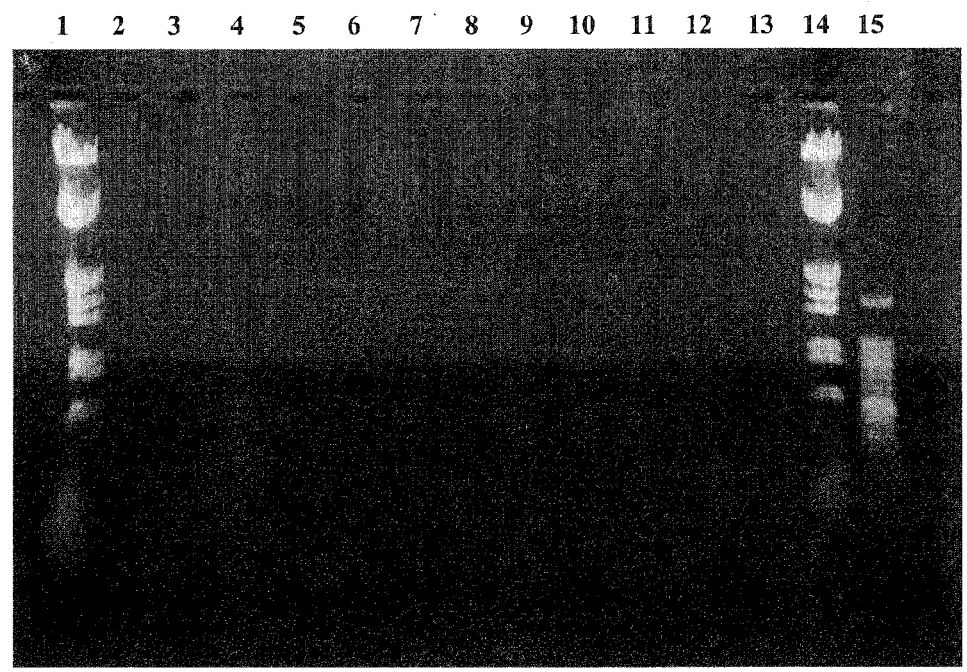

FIGURE 10
A.
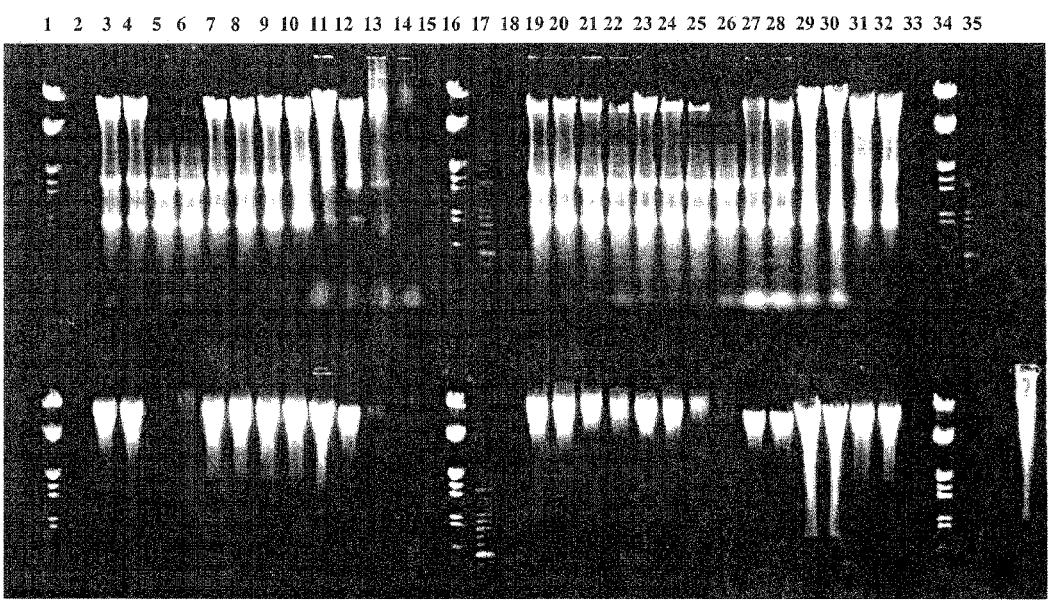
B.
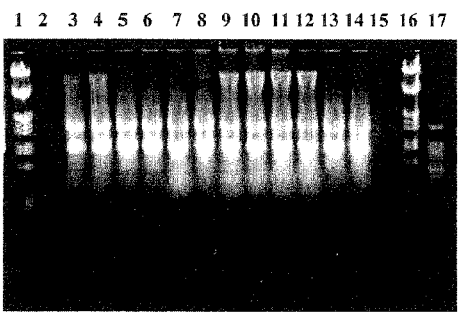
C.
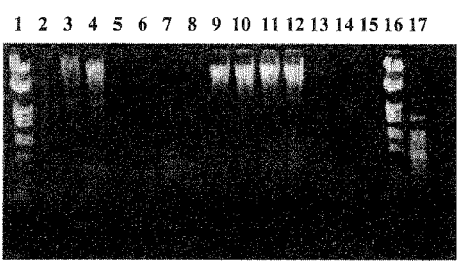

FIGURE 11
A.
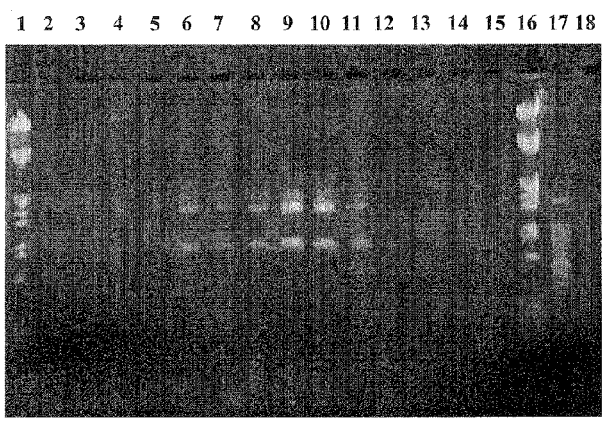
B.
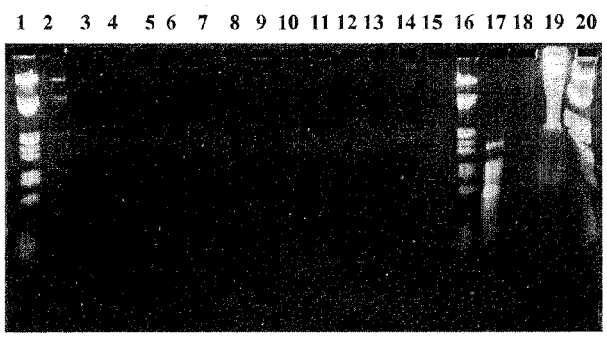
C.
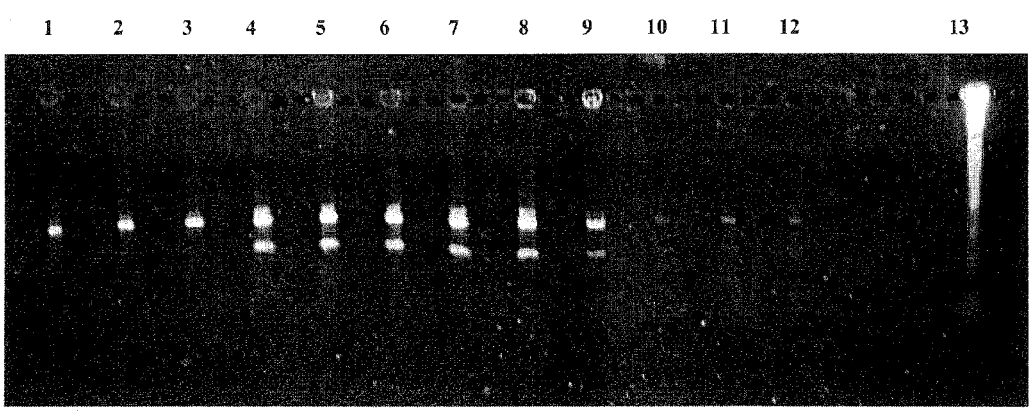

FIGURE 14
A.
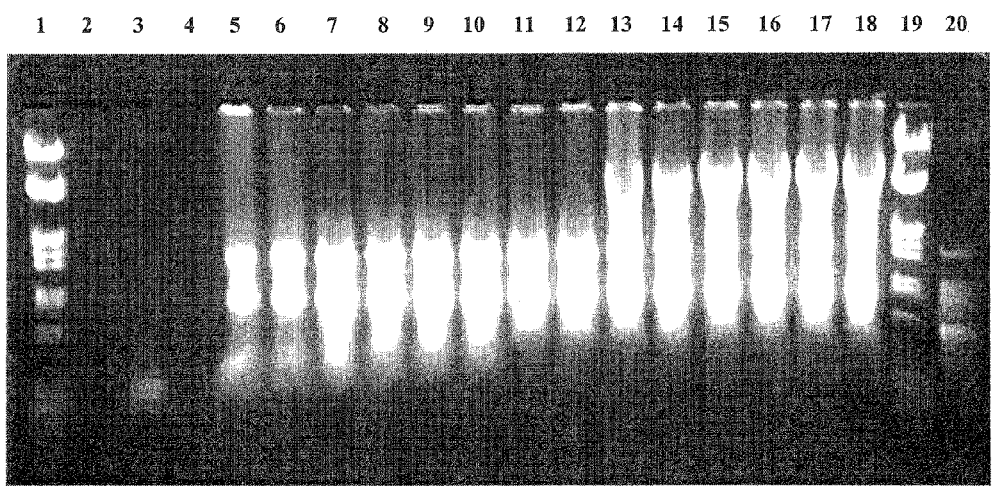
B.
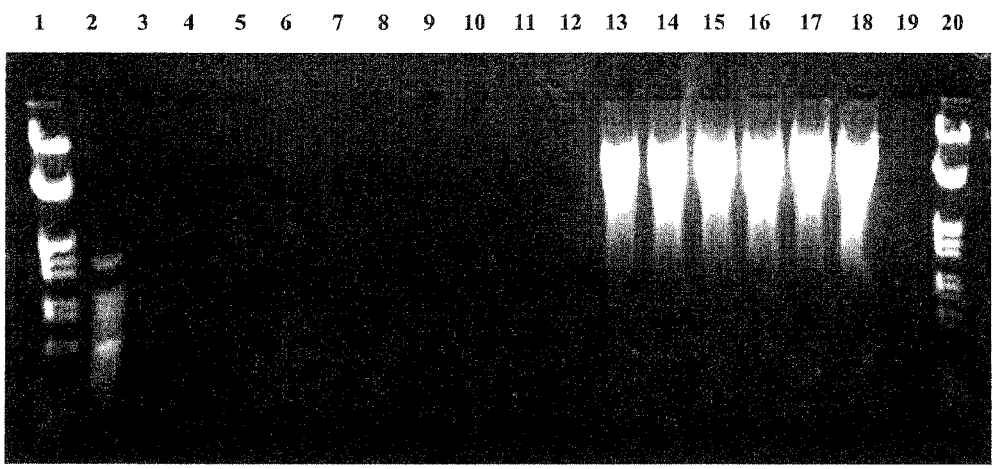

FIGURE 17
A.
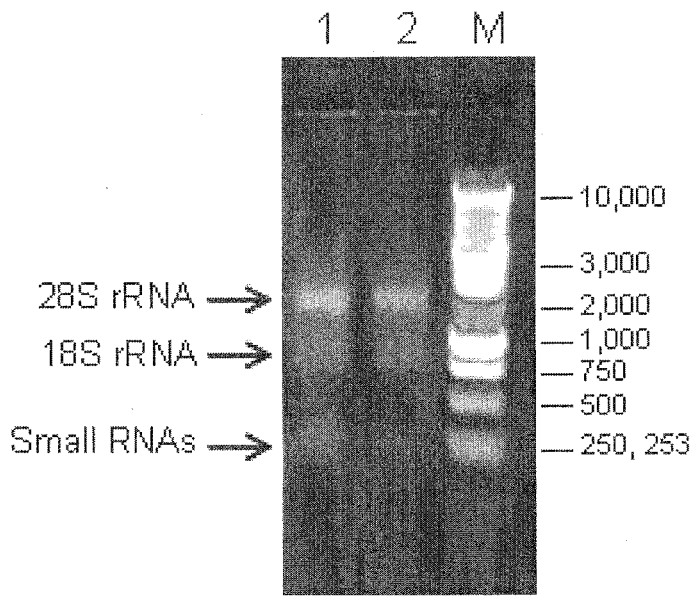
B.
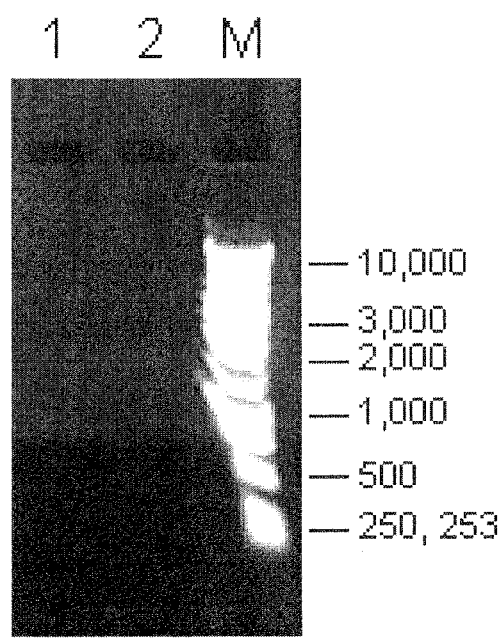

FIGURE 20A
21°C: Flowthrough and Wash

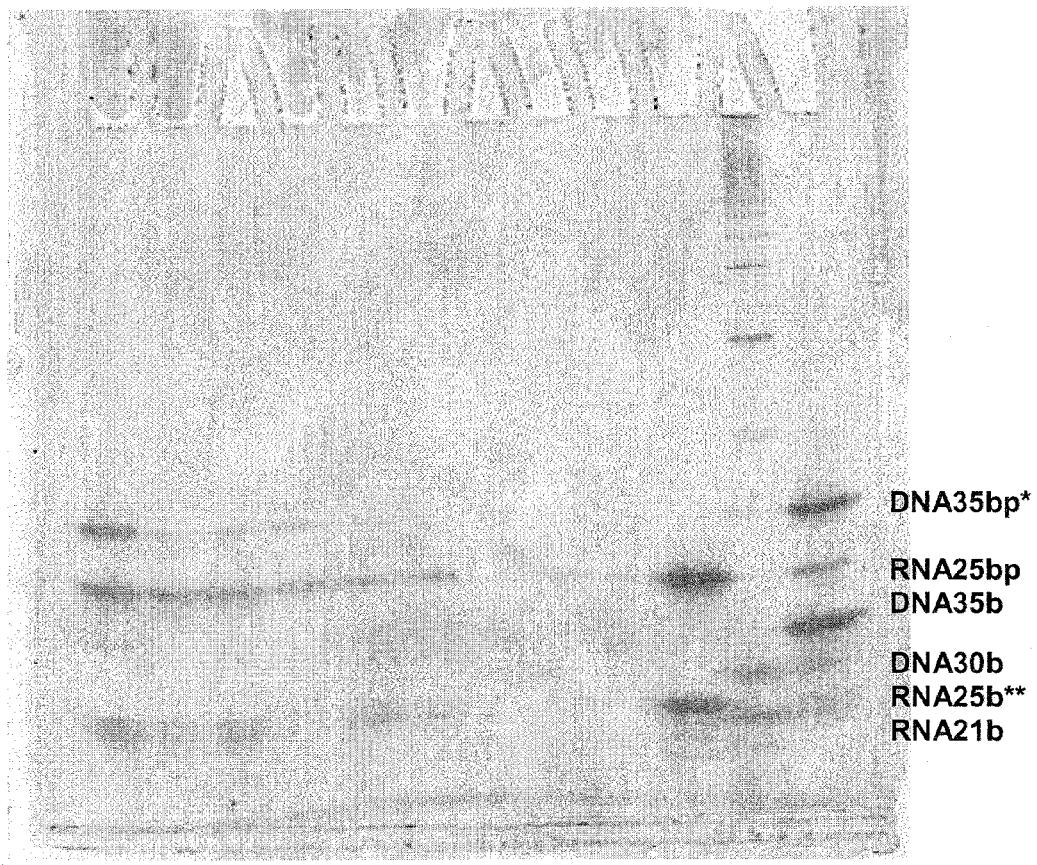

Lane  sample
1   No zeolite, flowthrough
2   + zeolite A, flowthrough
3   + zeolite B, flowthrough
4   wash, no zeolite
5   wash, +zeolite A
6   wash, +zeolite B 7,8,9 blank 10   $RNA_2RNA_{2'}$ 25bp and 25 bases 11   $RNA_1$ 21 bases, Promega 100bp ladder 12   $DNA_A DNA_A$ (35 bp and 35 bases)
      $RNA_2RNA_{2'}$ (25 bp and 25 bases)
      $DNA_B$ 30 bases, $RNA_1$ 21 bases \* "DNA35bp" denotes double stranded DNA, 35 base pairs (bp) in length.
\*\* "RNA25b" denotes single stranded RNA, 25 bases (b) in length.

FIGURE 20B
21°C Elutions

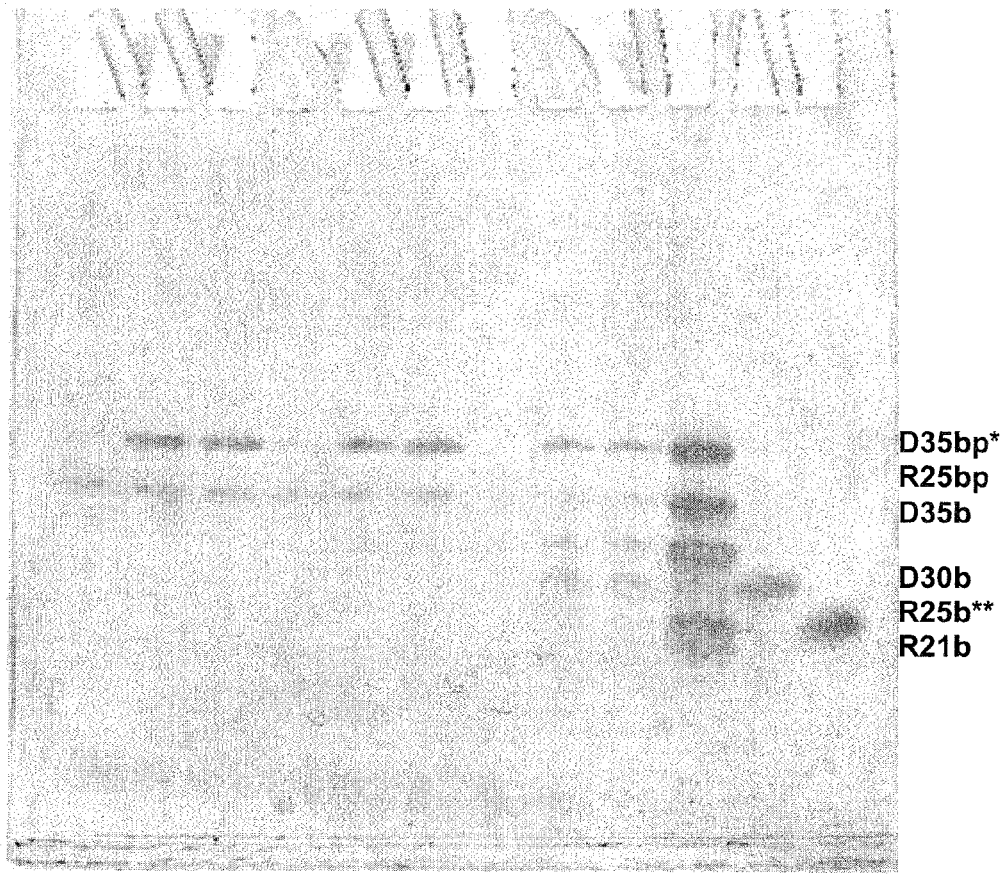

D35bp*
R25bp
D35b

D30b
R25b**
R21b

Lane    sample
1    Elution 1, no zeolite
2,3    Elution 1, + zeolite A
4    Elution 2, no zeolite
5,6    Elution 2, + zeolite A
7    Elution 3, no zeolite
8,9    Elution 3, + zeolite A: +particles 10    $DNA_A DNA_A$ (35 bp and 35 bases)
      $RNA_2 RNA_{2'}$ (25 bp and 25 bases)
      $DNA_B$ 30 bases, $RNA_1$ 21 bases 11    $DNA_B$ 30 bases
12    $RNA_2$ 25 bases \* "DNA35bp" denotes double stranded DNA, 35 base pairs (bp) in length.
\*\* "RNA25b" denotes single stranded RNA, 25 bases (b) in length.

FIGURE 20C
38°C: Flowthrough and Wash

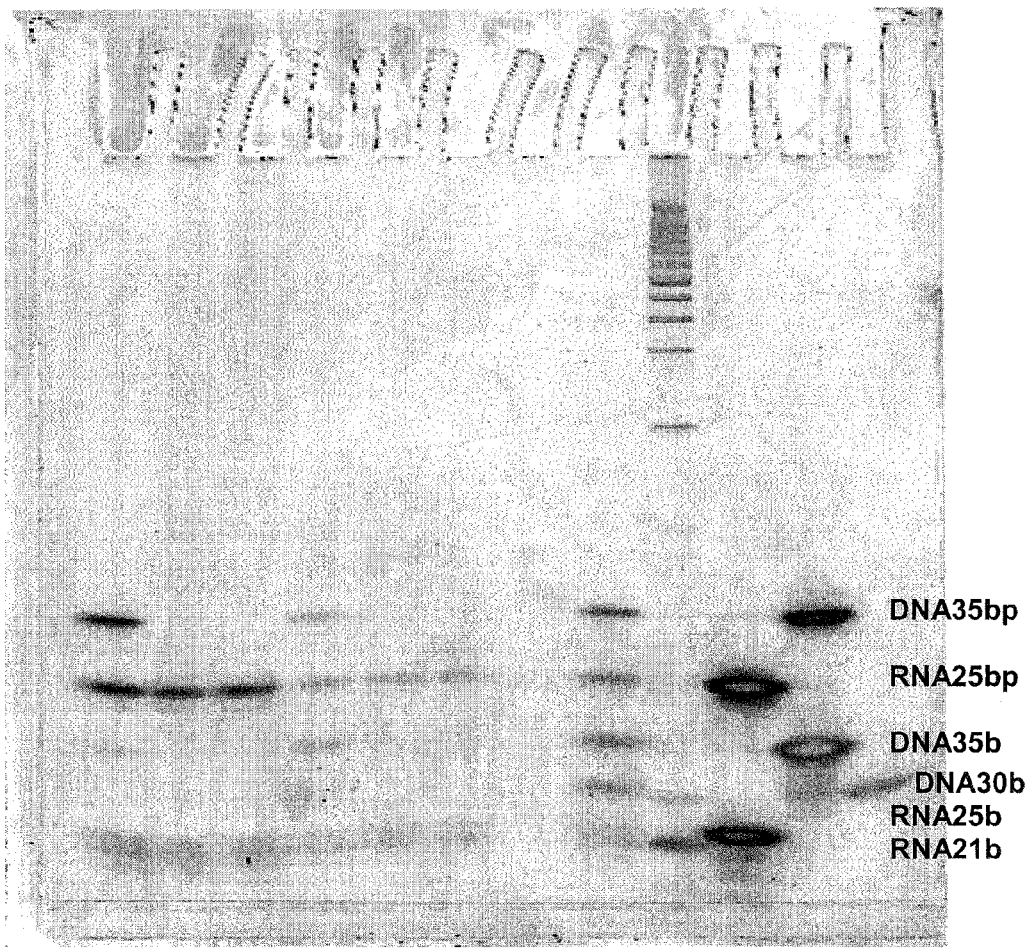

Lane sample
1 No zeolite, flowthrough
2 + zeolite A, flowthrough
3 + zeolite B, flowthrough
4 wash, no zeolite
5 wash, +zeolite A
6 wash, +zeolite B
7 blank
8 $DNA_A DNA_A$ (35 bp and 35 bases)
 $RNA_2 RNA_{2'}$ (25 bp and 25 bases)
 $DNA_B$ 30 bases, $RNA_1$ 21 bases 9 $RNA_1$ 21 bases
10 $RNA_2 RNA_{2'}$ 25bp and 25 bases
11 $DNA_B$, 30 bases
12 $DNA_A DNA_{A'}$ 35bp and 35 bases

* "DNA35bp" denotes double stranded DNA, 35 base pairs (bp) in length.
** "RNA25b" denotes single stranded RNA, 25 bases (b) in length.

FIGURE 20D
38°C: Elutions

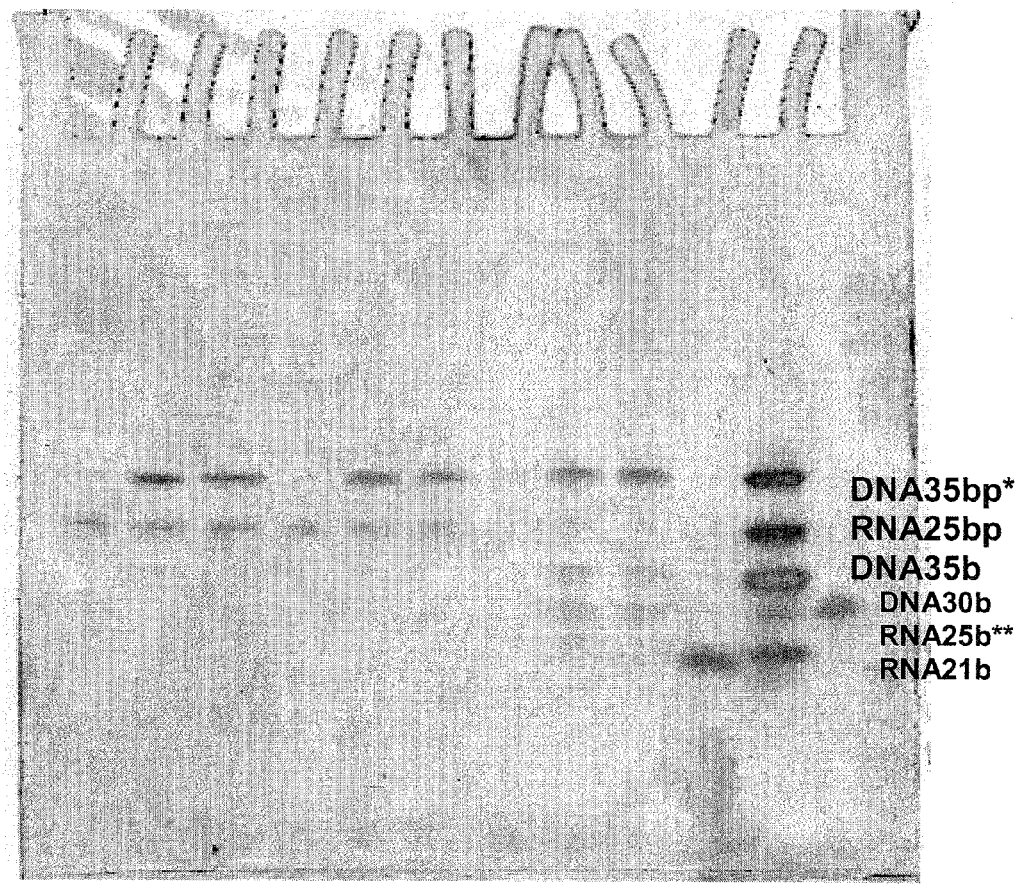

| Lane | sample |
|---|---|
| 1 | Elution 1, no zeolite |
| 2 | Elution 1, + zeolite A |
| 3 | Elution 1, + zeolite B |
| 4 | Elution 2, no zeolite |
| 5 | Elution 2, + zeolite A |
| 6 | Elution 2, + zeolite B |
| 7 | Elution 3, no zeolite |
| 8 | Elution 3, + zeolite A: +particles |
| 9 | Elution 3, + zeolite B: +particles |
| 10 | $RNA_2$ 25 bases |
| 11 | $DNA_A DNA_A$ (35 bp and 35 bases) $RNA_2 RNA_{2'}$ (25 bp and 25 bases) $DNA_B$ 30 bases, $RNA_1$ 21 bases |
| 12 | $DNA_B$ 30 bases |

\* "DNA35bp" denotes double stranded DNA, 35 base pairs (bp) in length.
\*\* "RNA25b" denotes single stranded RNA, 25 bases (b) in length.

FIGURE 21A
Binding to Zeolite 13X particles in Column:
Flow-Throughs

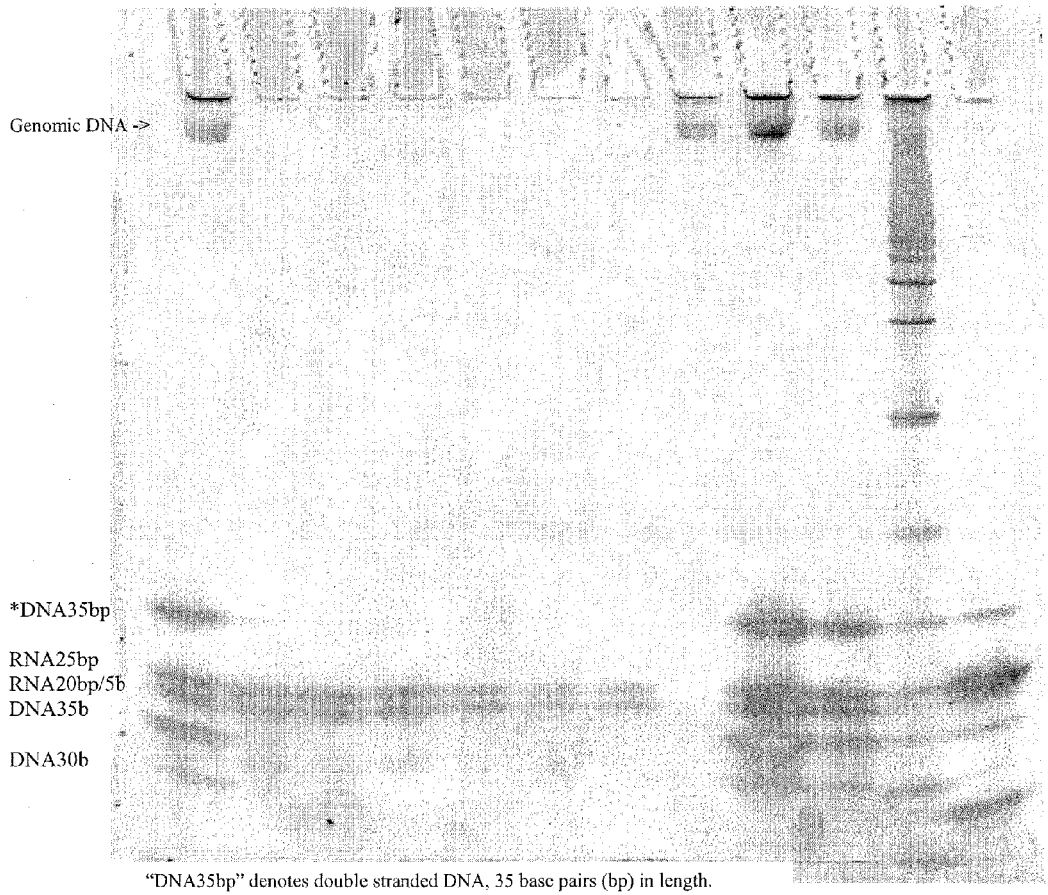

"DNA35bp" denotes double stranded DNA, 35 base pairs (bp) in length.
"RNA20bp/5b" denotes RNA, 20 bp double stranded / 5 bases single stranded.
"DNA30b" denotes single stranded DNA, 30 bases (b) in length.

| Lane | sample |
|---|---|
| 1 | Initial solution, pre-zeolite |
| 2,3,4 | After zeolite binding, spin |
| 5,6,7 | wash: Lysis+Dilution Buffer |
| 8 | human genomic DNA |
| 9 | genomic and oligo mixture |
| 10 | genomic and oligo mixture |
| 11 | Promega 100bp ladder |
| 12 | $DNA_2 DNA_{2'}$(35bp and 35 bases), $RNA_2 RNA_{2'}$ (25 bp and 25 bases) |

Binding to Zeolite 13X particles in Column: Elutions

\* "DS" double stranded
"SS" single stranded

| Lane | sample |
|---|---|
| 1,2,3 | first elution, water |
| 4,5,6 | $2^{nd}$ elution, water |
| 7,8,9* | $3^{rd}$ elution included zeolite |
| 10 | $DNA_B$ $DNA_{B'}$ 30bp, 30 bases |
| 11* | genomic + oligo ladder |
| 12 | genomic + $RNA_2 RNA_{2'}$ (25 bp and 25 bases) |

\* Note Carryover from lane 10

Binding to Zeolite 13X Particles, Pelleted: Supernatants

Lane  sample
1    Initial solution, pre-zeolite
2,3,4  After zeolite binding, spin
5,6,7  wash: Lysis+dilution buffer
8    genomic DNA + $R_1$(20 bases)
9    oligo ladder
10   oligo ladder + genomic
11   $DNA_B$ $DNA_{B'}$
12   $RNA_2 RNA_{2'}$

Binding to Zeolite 13X Particles, Pelleted:
Elutions

Lane  sample
1,2,3  first elution, water
4,5,6  $2^{nd}$ elution, water
7,8,9  $3^{rd}$ elution included zeolite
10     genomic + oligo ladder
11*    $DNA_B\ DNA_{B'}$ 30 bp, 30 bases
12    genomic + $R_2 R_{2'}$
        (25 bp, 25 bases)

* Note carryover from lane 12

Binding to Paramagnetic Zeolite 3A Particles:
Supernatants

Lane  sample
1     Initial solution, pre-zeolite
2,3,4  After zeolite binding, magnet
5,6,7  wash: Lysis+dilution buffer
8     oligo ladder
9     $DNA_B$ $DNA_{B'}$ (30bp, 30 bases)
10   oligo ladder + genomic DNA
11   $RNA_2 RNA_{2'}$ (25 bp, 25 bases)
12   $RNA_1$ (20 bases) + genomic

Binding to Paramagnetic Zeolite 3A Particles: Elutions

Lane sample
1,2,3 first elution, water
4,5,6 $2^{nd}$ elution, water
7,8,9* $3^{rd}$ elution including zeolite
10* genomic + oligo ladder
11 $DNA_B DNA_{B'}$ (30 bp, 30 bases) + $RNA_1$(20 bases)
12 genomic + $RNA_2 RNA_{2'}$ (25 bp and 25 bases)

* Note carryover from lane 12 to lane 11, and from lane 11 to lanes 9 and 10.

TPOX qPCR Standard Curve

TPOX qPCR Analysis of 1MIX and 2MIX Total RNA Samples

TPOX qPCR Analysis of SV +/- DNase Total RNA Samples

JOE-GAPDH qRT-PCR Standard Curve

JOE-GAPDH qRT-PCR Analysis of 1MIX and 2MIX Total RNA Samples

FAM-EDNRB qRT-PCR Standard Curve

FAM-EDNRB qRT-PCR Analysis of 1MIX and 2MIX Total RNA Samples

SEQUENCE LISTING

<160> NUMBER OF SEQ ID NOS: 13

<210> SEQ ID NO 1
<211> LENGTH: 21
<212> TYPE: RNA
<213> ORGANISM: Artificial
<220> FEATURE:
<223> OTHER INFORMATION: synthetic oligonucleotide

<400> SEQUENCE: 1
uauugcacuu gucccggccu g                                              21

<210> SEQ ID NO 2
<211> LENGTH: 25
<212> TYPE: RNA
<213> ORGANISM: Artificial
<220> FEATURE:
<223> OTHER INFORMATION: synthetic oligonucleotide

<400> SEQUENCE: 2
gagacccagu agccagaugu agcuu                                          25

<210> SEQ ID NO 3
<211> LENGTH: 25
<212> TYPE: RNA
<213> ORGANISM: Artificial
<220> FEATURE:
<223> OTHER INFORMATION: synthetic oligonucleotide

<400> SEQUENCE: 3
aagcuacauc uggcuacugg gucuc                                          25

<210> SEQ ID NO 4
<211> LENGTH: 35
<212> TYPE: DNA
<213> ORGANISM: Artificial
<220> FEATURE:
<223> OTHER INFORMATION: synthetic oligonucleotide

<400> SEQUENCE: 4
agctgtctag gtgacacgct agagtactcg agcta                               35

<210> SEQ ID NO 5
<211> LENGTH: 35
<212> TYPE: DNA
<213> ORGANISM: Artificial

```
<220> FEATURE:
<223> OTHER INFORMATION: synthetic oligonucleotide

<400> SEQUENCE: 5
tagctcgagt actctagcgt gtcacctaga cagct                              35

<210> SEQ ID NO 6
<211> LENGTH: 30
<212> TYPE: DNA
<213> ORGANISM: Artificial
<220> FEATURE:
<223> OTHER INFORMATION: synthetic oligonucleotide

<400> SEQUENCE: 6
gttacacatg cctacacgct ccatcatagg                                    30

<210> SEQ ID NO 7
<211> LENGTH: 20
<212> TYPE: RNA
<213> ORGANISM: Artificial
<220> FEATURE:
<223> OTHER INFORMATION: synthetic oligonucleotide

<400> SEQUENCE: 7
agacccagua gccagaugua                                               20

<210> SEQ ID NO 8
<211> LENGTH: 20
<212> TYPE: DNA
<213> ORGANISM: Artificial
<220> FEATURE:
<223> OTHER INFORMATION: synthetic oligonucleotide

<400> SEQUENCE: 8
gtccttgtca gcgtttattt                                               20

<210> SEQ ID NO 9
<211> LENGTH: 17
<212> TYPE: DNA
<213> ORGANISM: Artificial
<220> FEATURE:
<223> OTHER INFORMATION: synthetic oligonucleotide

<400> SEQUENCE: 9
cccagaaccg tcgactg                                                  17

<210> SEQ ID NO 10
<211> LENGTH: 15
<212> TYPE: DNA
<213> ORGANISM: Artificial
<220> FEATURE:
<223> OTHER INFORMATION: synthetic oligonucleotide

<400> SEQUENCE: 10
agccgagcca catcg                                                    15

<210> SEQ ID NO 11
<211> LENGTH: 17
<212> TYPE: DNA
<213> ORGANISM: Artificial
<220> FEATURE:
<223> OTHER INFORMATION: synthetic oligonucleotide

<400> SEQUENCE: 11
gaccaggcgc ccaatac                                                  17
```

```
<210> SEQ ID NO 12
<211> LENGTH: 23
<212> TYPE: DNA
<213> ORGANISM: Artificial
<220> FEATURE:
<223> OTHER INFORMATION: synthetic oligonucleotide

<400> SEQUENCE: 12
tcccaatatc ttgatcgcca gct                                      23

<210> SEQ ID NO 13
<211> LENGTH: 21
<212> TYPE: DNA
<213> ORGANISM: Artificial
<220> FEATURE:
<223> OTHER INFORMATION: synthetic oligonucleotide

<400> SEQUENCE: 13
tctcagctcc aaatggccag t                                        21
```

NUCLEIC ACID PURIFICATION WITH A BINDING MATRIX

CROSS-REFERENCE TO RELATED APPLICATIONS

This application is a continuation of U.S. application Ser. No. 11/636,174 filed Dec. 8, 2006, which claims priority to U.S. Provisional Application No. 60/748,825 filed Dec. 9, 2005. These applications are incorporated herein by reference in their entirety.

FIELD OF THE INVENTION

The present invention relates to methods, kits, and compositions for generating purified RNA samples and purified DNA samples. In particular, the present invention provides methods for generating a purified RNA or DNA sample from a sample containing both DNA and RNA molecules using a binding matrix that preferentially binds DNA or RNA in the presence of an acidic dilution buffer, or using a binding matrix that comprises acid zeolites, as well as compositions and kits for practicing such methods.

BACKGROUND OF THE INVENTION

Because of the structural similarity between DNA and RNA, previous RNA purification methods have often comprised isolating DNA and RNA together from biological sources. One commonly used method for isolating nucleic acids from cells and tissues was the "Sevag" procedure. This method comprises contacting a cell or tissue homogenate with phenol or a mixture of phenol and chloroform, thereby denaturing proteins and precipitating them while leaving nucleic acids in solution. This method, while still used, is hazardous, laborious and of limited utility for isolation of RNA from biological sources containing high amounts of ribonuclease (RNase), an extremely stable enzyme that degrades RNA.

An improved method for isolating intact RNA from ribonuclease-rich tissues was disclosed by Chirgwin et al., Biochemistry, 18: 5924-29 (1979). This method comprises exposing tissue homogenates to concentrated guanidinium thiocyanate and 2-mercaptoethanol, thereby eliminating nucleolytic degradation of RNA by denaturing all of the cellular proteins, including ribonuclease, at a rate which exceeded the rate of RNA hydrolysis by ribonuclease. Although RNA isolated in this manner was biologically active, it was not free of contamination by DNA, protein and other cellular materials. Subsequent, often extensive, manipulation was required to further purify the RNA from other cellular contaminants.

Silica based nucleic acid isolation techniques have been developed as alternatives to, or in addition to, the conventional isolation techniques described above for use in isolating total RNA from at least some types of biological materials. For example, an RNA isolation kit has been developed that uses a glass fiber filter in a spin filter basket and a hybrid lysis buffer/binding solution with a high concentration of guanidine hydrochloride and a chaotropic agent to isolate total RNA from simple biological materials, such as cultured cells, blood, yeast, and bacteria (See, e.g. High Pure RNA Isolation Kit from Roche Diagnostics). A system for isolating total RNA from bacterial cells and tissue using a spin basket with a silica gel-based membrane, and a lysis buffer/binding solution containing guanidinium isothiocyanate has also been developed (See, e.g. the RNeasy total RNA kit from QIAGEN Inc, Chatsworth, Calif.). Both systems described briefly above allow one to isolate total RNA, but the yield and purity of RNA isolated tends to be low, particularly when used to isolate RNA from complex biological materials, such as plant or animal tissue.

As such, what is needed are methods, compositions, and kits that allow for the purification of RNA from complex biological materials with high yield, while avoiding DNA contamination.

SUMMARY OF THE INVENTION

The present invention relates to methods, kits, and compositions for generating purified RNA samples and purified DNA samples. In particular, the present invention provides methods for generating a purified RNA or DNA sample from a sample containing both DNA and RNA molecules using a binding matrix that preferentially binds DNA or RNA in the presence of an acidic dilution buffer, or using a binding matrix that comprises acid zeolites, as well as compositions and kits for practicing such methods.

In some embodiments, the present invention provides methods of generating a purified RNA sample from an initial sample that comprises DNA and RNA molecules, the method comprising; a) contacting the initial sample with; i) a dilution buffer with an acidic pH, and ii) a binding matrix (e.g. a plurality of binding particles or composition coated with a plurality of binding particles) that preferentially binds DNA molecules in the presence of the dilution buffer, wherein the contacting generates a DNA-bound binding matrix; and b) separating the DNA-bound binding matrix from the initial sample thereby generating a purified RNA sample comprising a plurality of RNA molecules.

In certain embodiments, the present invention provides methods of generating a purified RNA sample, the method comprising; a) mixing an initial sample comprising a cell suspension with a lysis buffer under conditions such that a cell lysate is generated, b) contacting the cell lysate with; i) a dilution buffer with an acidic pH, and ii) a binding matrix that preferentially binds DNA molecules in the presence of the dilution buffer, wherein the contacting generates a DNA-bound binding matrix; and c) separating the DNA-bound binding matrix from the cell lysate thereby generating a purified RNA sample comprising a plurality of RNA molecules.

In certain embodiments, the binding matrix is configured to bind both double stranded and single stranded DNA molecules. In other embodiments, the binding matrix is configured to not bind double stranded or single stranded RNA molecules.

In some embodiments, the present invention provides methods of generating a purified RNA sample from an initial sample that comprises DNA and RNA molecules, the method comprising; a) contacting the initial sample with a binding matrix comprising acid zeolites such that a DNA-bound binding matrix is generated; and b) separating the DNA-bound binding matrix from the initial sample thereby generating a purified RNA sample comprising a plurality of RNA molecules.

In certain embodiments, the present invention provides methods of generating a purified sample from an initial sample that comprises DNA and target molecules comprising; a) contacting the initial sample with; i) a dilution buffer with an acidic pH, and ii) a nucleic acid binding matrix that preferentially binds DNA molecules in the presence of the dilution buffer, wherein the contacting generates a DNA-bound binding matrix; and b) separating the DNA-bound binding matrix from the initial sample thereby generating a purified sample. In some embodiments, at least a portion of the target molecules comprise proteins. In further embodiments, at least a portion of said target molecules comprise lipid molecules. In other embodiments, at least a portion of the target molecules comprise drug molecules. In some embodiments, the purified sample is substantially DNA-free.

In certain embodiments, the present invention provides methods of generating a purified sample from an initial sample that comprises DNA and target molecules comprising; a) contacting the initial sample with a nucleic acid binding matrix comprising acid zeolites, wherein the contacting generates a DNA-bound binding matrix; and b) separating the DNA-bound binding matrix from the initial sample thereby generating a purified sample.

In additional embodiments, the binding matrix, whether in an acidic buffer or not in an acidic buffer, comprises binding particles, a composition coated with binding particles, or a solid support. In particular embodiments, the binding matrix is magnetic and the separating step is performed with magnetic separation type techniques. In certain embodiments, the magnetic binding matrix comprises particles containing two or more magnetic cores bound to a zeolite matrix or acid zeolite matrix. In other embodiments, the particles comprising two or more magnetic cores are covered by a zeolite or acid zeolite coating. In certain preferred embodiments, the binding matrix comprises binding particles (e.g. zeolites, acid zeolites, a solid acid catalyst, etc.). In other embodiments, the binding matrix comprises a membrane (e.g. silicon membrane, zeolite or acid zeolite membrane, or combined silicon-zeolite or silicon-acid zeolite membrane). In certain embodiments, a zeolite membrane is formed on the surface of a silicon membrane, or completely surrounding the silicon membrane, to form a combined silicon-zeolite membrane.

In certain embodiments, the plurality of RNA molecules comprises total RNA from the lysed cells. In other embodiments, the plurality of RNA molecules includes small RNA molecules (e.g. less than about 150, 120, 100, 80, 70, 60, 50, or 40 bases in length). In some embodiments, the methods further comprise the step of exposing the purified RNA sample to a binding component (e.g. silicon membrane) such that an RNA-bound binding component is generated which comprises a plurality of bound RNA molecules. In particular embodiments, the methods further comprise the step of washing the RNA-bound binding component (e.g. to remove salts and impurities). In other embodiments, the methods further comprise the step of eluting at least a portion of the bound RNA molecules from the RNA-bound binding member with a wash solution such that a purified RNA preparation is generated, wherein the purified RNA preparation comprises a plurality of eluted RNA molecules.

In certain embodiments, the initial sample comprises a cell lysate, wherein the cell lysate comprises lysed cells, and wherein the plurality of eluted RNA molecules are present in the purified RNA preparation at a level of at least 5 µg of RNA per 1 million of the lysed cells originally present in the sample (e.g. at least 5, 6, 7, 8, 9, 10, or more µg of RNA per 1 million lysed cells). In particular embodiments, the amount of RNA present in the purified RNA sample and/or purified RNA preparation is at least 75% of the amount present in the original sample. In other words, the yield is at least 75%, preferably at least 85%, and more preferably at least 95%. In additional embodiments, the yield is between 80-100%, or between 95-100%.

In some embodiments, the purified RNA sample and/or purified RNA preparation are substantially DNA-free. In other embodiments, the purified RNA sample and/or purified RNA preparation are essentially DNA-free. In particular embodiments, the purified RNA sample and/or the purified RNA preparation do not contain detectable DNA when the sample is subjected to a DNA contamination assay employing conditions as described in Example 1. In other embodiments, the purified RNA sample or the purified RNA preparation contains less than 40 discreet DNA molecules (e.g. less than 39, 35, 30, 25, 15, 10, 5, or 0 discrete DNA molecules per 100 ng of RNA present in the purified RNA sample or purified RNA preparation, and which may be determined by real-time PCR). In some embodiments, the purified RNA sample or the purified RNA preparation contain less than 100 picograms of DNA, less than 75 picograms of DNA, less than 50 picograms of DNA, less than 25 picograms of DNA, or less than 10 picograms of DNA. In certain embodiments, the purified RNA sample and/or purified RNA preparation contains less than 5%, or less than 3% or less than 1%, less than 0.5%, less than 0.25%, less than 0.1%, or less than 0.05% of the mass of DNA (or number of molecules of DNA) present in the original sample.

In certain embodiments, the purified RNA sample or purified RNA preparation is enriched for RNA molecules compared to the initial sample. For example, RNA in a sample may be enriched (e.g., as measured by UV absorption) about or at least about 2-fold, 3.5-fold, 5-fold, 10-fold, 50-fold, 100-fold, 150-fold, 200-fold, 500-fold, 800-fold, 1000-fold, 2000-fold, and all ranges therein as determined by the concentration (e.g. ug/ml) or mass of RNA molecules relative to the concentration or mass of total RNA molecules prior to contacting the initial sample with the binding matrix in the acidic dilution buffer. Enrichment and/or purification may also be measured in terms of the number of RNA molecules relative to the number of total RNA molecules present in the original or initial sample. RNA molecules can be isolated such that a sample is enriched (e.g., as measured by UV absorption) about or at least about 2-fold, 3.5-fold, 5-fold, 10-fold, 50-fold, 100-fold, 150-fold, 200-fold, 500-fold, 800-fold, 1000-fold, 2000-fold, and all ranges therein in RNA molecules as determined by number of RNA molecules relative to total number of RNA molecules prior to contacting the initial sample with the binding matrix in the acidic dilution buffer. Enrichment and/or purification of RNAs may also be measured in terms of the increase of RNA molecules relative to the number of total RNA molecules. RNA molecules can be isolated such that the amount of RNA molecules is increased about or at least about 10%, 15%, 20%, 25%, 30%, 35%, 40%, 45%, 50%, 55%, 60%, 65%, 70%, 75%, 80%, 85%, 90%, 95% or more with respect to the total amount of RNA in the sample before and after isolation.

In particular embodiments, the purified RNA sample or the purified RNA preparation are DNase-free or substantially DNase free (e.g., using AMBION's DNaseAlert™ QC System High-throughput, Fluorometric DNase Detection Assay that sample is found to have less than 10 picograms of DNase enzymes). In other embodiments, the initial sample is selected from the following; a cell lysate, a previously purified RNA sample, an RNA control sample, a pharmaceutical drug; a protein preparation; a lipid preparation; a reaction mixture where the presence of DNA is undesirable (e.g. Promega's Taq products). In some embodiments, the contacting step is conducted under alcohol-free conditions.

In certain embodiments, the separating step comprises passing the initial sample through a clearing column. In other embodiments, the separating step comprises centrifuging the sample such that a pellet forms which contains the DNA-bound binding particles, and separating the pellet from the remainder of the sample.

In some embodiments, the sample is heated to a temperature of between 25 and 80 degrees Celsius prior to the separating step, although higher and lower temperature may be used. In certain embodiments, the sample is heated to a temperature of between 25 and 80 degrees Celsius after the dilution buffer and binding particles have been added to the sample. In other embodiments, the sample is heated to a temperature of between 25 and 80 degrees Celsius prior to the addition of the dilution buffer and/or binding particles to the sample. In additional embodiments, the sample is heated to a temperature of at least 50 degrees, or at least 75 degrees Celsius. In some embodiments, the heating is conducted for about 1-15 minutes (e.g. the sample is incubated at about 75 degrees Celsius for about 3 minutes, although longer and shorter incubation times may be used).

In particular embodiments, the dilution buffer comprises a citrate buffer or similar buffer. In other embodiments, the dilution buffer further comprises about 2-4 M NaCl (or other concentrations of NaCl). In other embodiments the dilution buffer further comprises a chaotrope (e.g. guanidinium at concentrations of 0.2M to 2M). In further embodiments, the sample comprises a cell lysate. In certain embodiments, the cell lysate comprises RNA molecules, DNA molecules, and non-nucleic acid cellular debris (e.g. cell walls, proteins, enzymes, or other non-nucleic acid contents of the lysed cells). In further embodiments, the DNA-bound binding matrix (e.g. DNA-bound binding particles) also serve to trap or bind to the non-nucleic acid cellular debris such that separating the DNA-bound binding particles serves to remove a substantial proportion of the non-nucleic acid cellular debris.

In some embodiments, the cell lysate is generated by contacting a cell suspension comprising a plurality of cells with a lysis buffer comprising a chaotropic agent. In certain embodiments, the plurality of cells are selected from: human cells, mouse cells, plant cells, bacteria cells, transformed cells, or other type of cell. In additional embodiments, the chaotropic agent is selected from the group consisting of sodium perchlorate, guanidinium hydrochloride, guanidinium isothiocyanate, guanidinium thiocyanate, sodium iodide, potassium iodide, and combinations thereof. In particular embodiments, the chaotropic agent is present in a concentration from about 0.1M to about 10.0M, or similar concentrations. In further embodiments, the lysis buffer further comprises a reducing agent (e.g. beta-mercaptoethanol).

In preferred embodiments, the binding matrix comprises binding particles. In certain embodiments, the binding particles include, but are not limited to, silica gel, sol gel, glass, powdered glass, quartz, alumina, zeolites, acid zeolites, $Fe_3O_4$-zeolite, Silica-$Fe_3O_4$-zeolite particles (e.g., Magne-Sil®-zeolite particles), titanium dioxide, and zirconium dioxide. In some embodiments, the binding particles comprise silicon. In particular embodiments, the binding particles comprise tectosilicates. In preferred embodiments, the binding particles comprise zeolite particles. In preferred embodiments, the binding particles are synthetic molecular sieve zeolites, preferably Type 13X, or acid zeolite derivatives of zeolite 13X. In other preferred embodiments, the binding particles are synthetic molecular sieve zeolites, preferably Type 3A, or acid zeolite derivatives of Type 3A. In other preferred embodiments, the binding particles are synthetic molecular sieve zeolites, preferably a mixture of Type 3A and Type 13X, or mixtures of their acid zeolite derivatives.

In particular embodiments, the particle size is from 0.1 μm to 100 μm, but is not limited to such sizes. In other embodiments, the binding particles are less than about 15 μm or less than 10 μm is size. In some embodiments, the binding particles have a pore size between 3-15 Å (e.g., 3, 5, 7, 8, 10, 12, or 14 Å). In preferred embodiments, the pore size is about 10 Å. However, the present invention is not limited to such sizes.

In some embodiments, the dilution buffer has a pH of 6.5 or less or 6.0 or less. In other embodiments, the dilution buffer has a pH between 3.0 and 5.5. In particular embodiments, the DNA molecules in the sample comprise genomic DNA molecules. In further embodiments, the clearing agent further comprises 1-2 M NaCl.

In certain embodiments, the present invention provides kits for generating a purified RNA sample comprising; a) a dilution buffer with an acidic pH; and b) a binding matrix, wherein the binding matrix is configured to preferentially bind DNA molecules in the presence of the dilution buffer. In certain embodiments, the binding matrix comprises binding particles (e.g. membrane coated with binding particles or a clearing agent solution comprising binding particles).

In particular embodiments, the present invention provides kits for generating a purified RNA sample comprising; a) a binding matrix configured to preferentially bind DNA molecules in the presence of a dilution buffer with an acidic pH; and b) a kit component selected from the following list: i) the dilution buffer; ii) an insert component, wherein the insert component comprises written instructions for using the binding matrix to remove DNA molecules from a sample containing both DNA and RNA molecules; iii) a lysis buffer, wherein the lysis buffer comprises a chaotropic agent; iv) a wash solution; v) a clearing column; and vi) a binding column. In certain embodiments, the kits further comprise a second, third, fourth, fifth, or sixth component selected from the list of kit components. In some embodiments, the kits comprise control samples (e.g. negative and/or positive controls). In particular embodiments, the binding matrix comprises binding particles.

In some embodiments, the present invention provides kits for generating a purified RNA sample comprising; a) a dilution buffer with an acidic pH; and b) an insert component, wherein the insert component comprises written instructions for using a binding matrix to remove DNA molecules from a sample containing the dilution buffer and both DNA and RNA molecules, wherein the binding matrix preferentially binds DNA molecules in the presence of the dilution buffer.

In certain embodiments, the present invention provides compositions comprising: i) an initial sample comprising DNA and RNA molecules, and ii) a binding matrix, wherein the binding matrix is bound to 10 times the number of DNA molecules as RNA molecules.

In particular embodiments, the present invention provides compositions comprising; a) a dilution buffer with an acidic pH; and b) a binding matrix that preferentially binds DNA molecules in the presence of the dilution buffer. In further embodiments, the compositions further comprise a sample comprising DNA and RNA molecules. In other embodiments, the compositions further comprise a lysis buffer, wherein the lysis buffer comprises a chaotropic agent.

In some embodiments, the present invention provides compositions comprising; a) zeolite particles present at a concentration of about 0.1-1.0 g/ml; and b) a NaCl solution present at a concentration of about 1-3M. In certain embodiments, the zeolite particles are present at a concentration of about 0.5 g/ml (e.g. 0.2-0.8 g/ml). In other embodiments, the NaCl solution is present at a concentration of about 2 M. In particular embodiments, the compositions further comprise a chelating agent. In additional embodiments, the chelating agent comprises ethylene diamine tetra-acetic acid (EDTA) present at a concentration of about 0.1 mM to 10 mM with a pH of about 8.0. In preferred embodiments, the zeolite particles are configured to preferentially bind DNA in the presence of a buffer with an acidic pH. In other embodiments, the zeolite particles comprise Type 13X molecular sieve zeolites, or acid zeolite derivatives of Type 13X. In other embodiments, the zeolite particles comprise Type 3A molecular sieve zeolites or acid zeolite derivatives of Type 3A zeolites. In other embodiments, the zeolite particles comprise a mixture of Type 3A and Type 13X molecular sieve zeolites, or mixtures of acid zeolite derivatives thereof.

In particular embodiments, the present invention provides composition comprising about 35-55% by weight (e.g., 35% . . . 40% . . . 47% . . . 55%) zeolites (e.g., 13X zeolites), 1.5-2.5 M NaCl (e.g., 2.0M NaCl), and 0.05 to 1.5 mM EDTA (e.g, 0.1 mM EDTA).

In certain embodiments, the RNA purification methods of the present invention are used prior to RT-PCR or quantitative RT-PCR, or other procedures where it is preferred that DNA not be present. In some embodiments, the RNA purification methods are used for research, diagnostics, preparation of therapeutics, quality control monitoring, or any other application known or later discovered where it is desired to collect, purify, analyze, detect, and/or characterize nucleic acid molecules (e.g. RNA molecules).

In other embodiments, the present invention provides methods of generating a purified DNA sample from an initial sample that comprises DNA and RNA molecules, the method comprising; a) contacting the initial sample with; i) a dilution buffer with an acidic pH, and ii) a binding matrix (e.g. a plurality of binding particles or composition coated with a plurality of binding particles) that preferentially binds RNA molecules in the presence of the dilution buffer, wherein the contacting generates a RNA-bound binding matrix; and b) separating the RNA-bound binding matrix from the initial sample thereby generating a purified DNA sample comprising a plurality of DNA molecules. In preferred embodiments, the binding matrix that preferentially binds RNA molecules in the presence of the dilution buffer comprises titanium oxide.

In further embodiments, the present invention provides methods of generating a purified DNA sample, the method comprising; a) mixing an initial sample comprising a cell suspension with a lysis buffer under conditions such that a cell lysate is generated, b) contacting the cell lysate with; i) a dilution buffer with an acidic pH, and ii) a binding matrix that preferentially binds RNA molecules in the presence of the dilution buffer, wherein the contacting generates a RNA-bound binding matrix; and c) separating the RNA-bound binding matrix from the cell lysate thereby generating a purified DNA sample comprising a plurality of DNA molecules.

In some embodiments, the methods further comprise the step of exposing the purified DNA sample to a binding component such that a DNA-bound binding component is generated which comprises a plurality of bound DNA molecules. In particular embodiments, the methods further comprise the step of washing the DNA-bound binding component (e.g. to remove salts and impurities). In other embodiments, the methods further comprise the step of eluting at least a portion of the bound DNA molecules from the DNA-bound binding member with a wash solution such that a purified DNA preparation is generated, wherein the purified DNA preparation comprises a plurality of eluted DNA molecules.

In certain embodiments, the sample comprises a cell lysate, wherein the cell lysate comprises lysed cells, and wherein the plurality of eluted DNA molecules are present in the purified DNA preparation at a level of at least 5 µg of DNA per 1 million of the lysed cells originally present in the sample (e.g. at least 5, 6, 7, 8, 9, 10, or more µg of DNA per 1 million lysed cells). In particular embodiments, the amount of DNA present in the purified DNA sample and/or purified DNA preparation is at least 75% of the amount present in the original sample. In other words, the yield is at least 75%, preferably at least 85%, and more preferably at least 95%. In additional embodiments, the yield is between 80-100%, or between 95-100%.

In some embodiments, the purified DNA sample and/or purified DNA preparation are substantially RNA-free. In other embodiments, the purified DNA sample and/or purified DNA preparation are essentially RNA-free. In particular embodiments, the purified DNA sample and/or the purified DNA preparation do not contain detectable RNA when the sample is subjected to a RNA contamination assay employing conditions as described in Example 9. In other embodiments, the purified DNA sample or the purified DNA preparation contains less than 40 discreet RNA molecules (e.g. less than 39, 35, 30, 25, 15, 10, 5, or 0 discrete DNA molecules per 10 ug of DNA as determined by real-time PCR). In some embodiments, the purified DNA sample or the purified DNA preparation contain less than 100 picograms of RNA, less than 75 picograms of RNA, less than 50 picograms of RNA, less than 25 picograms of RNA, or less than 10 picograms of RNA. In certain embodiments, the purified DNA sample and/or purified DNA preparation contains less than 5%, or less than 3% or less than 1%, less than 0.5%, less than 0.1%, or less than 0.05% of the mass of RNA present in the original sample.

In particular embodiments, the present invention provides kits for generating a purified DNA sample comprising; a) a binding matrix configured to preferentially bind RNA molecules (e.g. titanium oxide) in the presence of a dilution buffer with an acidic pH; and b) a kit component selected from the following list: i) the dilution buffer; ii) an insert component, wherein the insert component comprises written instructions for using the binding matrix to remove RNA molecules from a sample containing both DNA and RNA molecules; iii) a lysis buffer, wherein the lysis buffer comprises a chaotropic agent; iv) a wash solution; v) a clearing column; and vi) a binding column. In certain embodiments, the kits further comprise a second, third, fourth, fifth, or sixth component selected from the list of kit components. In some embodiments, the kits comprise control samples (e.g. negative and/or positive controls). In particular embodiments, the binding matrix comprises binding particles.

In some embodiments, the present invention provides kits for generating a purified RNA sample comprising; a) a binding matrix comprising acid zeolites configured to preferentially bind DNA molecules; and b) at least one kit component selected from the following list: i) a dilution buffer; ii) an insert component, wherein the insert component comprises written instructions for using the binding matrix to remove DNA molecules from an initial sample containing both DNA and RNA molecules; iii) a lysis buffer, wherein the lysis buffer comprises a chaotropic agent; iv) a wash solution; v) a clearing column; and vi) a binding column.

In particular embodiments, the present invention provides an article comprising a membrane, wherein the membrane comprises a binding matrix (e.g. titanium oxide, zeolite particles, acid zeolites, etc.) configured to preferentially bind DNA or RNA in an acidic buffer. In some embodiments, the present invention provides an article comprising a membrane, wherein the membrane comprises zeolites, or acid zeolites. In some embodiments, the present invention provides an article comprising a membrane, wherein the membrane comprises a silica membrane coated with zeolite, or acid zeolite derivatives thereof (e.g., a standard silicon membrane coated on all surfaces with zeolites). In some embodiments, the present invention provides an article comprising a membrane, wherein the membrane comprises zeolite particles. In certain embodiments, the membrane is configured to be inserted into a binding column (e.g, a binding column, or 96 well plate, generally used to purify RNA or DNA samples with the aid of a centrifuge and/or vacuum system to pull liquid through the membrane). In other embodiments, the membrane further comprises silica (e.g. the membrane material is made of silica and/or silica that is bound to zeolite particles). In further embodiments, the membrane is approximately circular in shape. In certain embodiments, the membrane is less than about 4, or 3 or 2 centimeters in length or diameter, or wherein said membrane has a diameter between about 7 and about 11 millimeters or between 8 and 10 millimeters. In some embodiments, the membrane is between about 5 millimeters and 30 millimeters (e.g. 5 mm, 7 mm, 9 mm, 9.1 mm, 9.5 mm, 10 mm, 14 mm, 14.4 mm, 25 mm, 26 mm, 26.7 mm, 26.9 mm or 30 mm). In some embodiments, the membrane is less than about 3, or 2 or 1 millimeters in thickness. In particular embodiments, the membrane is composed entirely or nearly entirely of zeolites (e.g. at least 95%, 98%, or 99% of the membrane is composed of zeolites).

In particular embodiments, the present invention provides DNA-binding membranes comprising zeolites or acid zeolites. In certain embodiments, the membranes are configured to be inserted into a binding column. In some embodiments, the DNA-binding membrane further comprises silica. In other embodiments, the membrane is approximately circular in shape (e.g. elliptical, circular, etc.). In further embodiments, the membrane is less than about 4, or less than about 3, or less than about 2 centimeters in diameter, or wherein said membrane has a diameter between about 5 and about 35 millimeters or between 8 and 10 millimeters. In some embodiments, the membrane is between about 5 millimeters and 30 millimeters (e.g. 5 mm, 7 mm, 9 mm, 9.1 mm, 9.5 mm, 10 mm, 14 mm, 14.4 mm, 25 mm, 26 mm, 26.7 mm, 26.9 mm or 30 mm). In certain embodiments, the membrane is less than about 3 millimeters in thickness (e.g., less than about 2 millimeter or less than 1 millimeter, or between about 2.9 and 1.2 millimeters in thickness). In particular embodiments, the membrane is composed entirely or nearly entirely of acid zeolites (e.g. at least 90%, 95% or 98% of the membrane is composed of acid zeolites).

In some embodiments, the present invention provides a DNA-binding membrane comprising: i) a silicon membrane comprising a top surface and a bottom surface, and ii) zeolites, wherein the zeolites are disposed on the top surface, on the bottom surface, or on both the top and bottom surfaces. In certain embodiments, at least 75%, 80%, 90%, or 99% of the top surface is covered with the zeolites. In other embodiments, at least 75%, 90%, 90%, or 99% of the bottom surface is covered with the zeolites. In particular embodiments, the membrane is between about 5-30 millimeters in diameter. In other embodiments, the membrane is between about 8-10 millimeters in diameter. In further embodiments, the membrane is approximately circular in shape (e.g. circular, elliptical, nearly circular, etc.). In some embodiments, the membrane is between about 5 millimeters and 30 millimeters (e.g. 5 mm, 7 mm, 9 mm, 9.1 mm, 9.5 mm, 10 mm, 14 mm, 14.4 mm, 25 mm, 26 mm, 26.7 mm, 26.9 mm or 30 mm). In other embodiments, the membrane is between less than about 4 centimeters in diameter. In further embodiments, the membrane is approximately circular in shape.

Membranes according to the present invention could be used with commercially available sample preparation devices such as single-column centrifuge tubes and multi-well plates. Commercially available tubes from companies such as Eppendorf, Corning and Becton Dickinson's Falcon(r) brand include 0.5 mL, 0.65 mL, 1.0 mL, 1.2 mL, 1.5 mL, 1.7 mL, 2.0 mL, 2.1 mL, 2.2 mL, 5 mL, 8 mL, 10 mL, 13 mL, 15 mL, 20 mL, 50 mL, 175 mL and 225 mL capacity centrifuge tubes. The diameters of these tubes vary depending on design but are typically in the range of about 3.0 mm to about 61 mm. For example a BD Falcon™ Conical Centrifuge tube, 15 mL capacity has an approximate outer diameter ("O.D.") of 17 mm, the 50 mL capacity tube has an O.D. of 30 mm, and the 175 mL and 225 mL tubes have an O.D. of 61 mm. Molecular Research Center Inc. provides polypropylene centrifuge tubes with a 5 mL capacity (13 mm O.D.), 8 mL capacity (13 mm O.D.), 13 mL capacity (17 mm O.D.) and 20 mL capacity (21 mm O.D.). CryoStor™ Vials sold by Denville Scientific Inc. (Metuchen, N.J.) with a volume capacity of 0.65 mL, 1.7 mL and 2.0 mL all have an O.D. of 10 mm. Sample preparation devices are typically made from plastics such as clear polypropylene (PP) or polyethylene terephthalate (PET) but can be constructed with any material that would not substantially interfere with the sample. The internal diameter of a tube depends on the tube configuration, construction materials and manufacturing tolerances. For example, centrifuge tubes: 1) from Corning (Corning, N.Y.) include a 50 mL capacity tube which has a diameter of 26.9 mm; a 15 mL capacity with a diameter of 14.4 mm; and a 2.0 mL capacity tube with a diameter of 9.5 mm; 2) from Fisher Scientific (Hampton, N.H.) include a 50 mL capacity tube with a diameter of 26.7 mm; and 3) from Eppendorf, include a 1.5 mL capacity tube with a diameter of 9.0 mm-9.1 mm, and a 2.0 mL capacity tube with a diameter of 9.0 mm.

The membranes could also be used in conjunction with well-plates for simultaneous preparation of, for example, 6, 8, 10, 12, 24, 48, 96, 384 and 1586 samples. Wells in commercially available plates are typically squared or rounded in shape and are typically in a uniform pattern across the plate. Many manufacturers of well plates use a standard dimensions calculated from center to center of the wells in allow the plates to be utilized on different robotic instruments. 96 well plates, for example, typically measure 9 mm from center to center of the wells. The internal dimensions will also depend on the configuration of the wells, construction materials and manufacturing tolerances. The selection of membrane size is dependent on the internal dimensions/configuration of these preparation devices, construction materials and manufacturing tolerances that vary from manufacturer to manufacturer.

DESCRIPTION OF THE FIGURES

FIG. 1A shows an ethidium bromide stained gel of human cell lysate samples purified as described in Example 1. FIG. 1B shows the results of a DNA contamination assay as described in Example 1 were exposed to RNase digestion prior to loading on the gel.

FIG. 2A shows an ethidium bromide stained gel of the cow spleen cell lysate samples purified as described in Example 2. FIG. 2B shows the results of a DNA contamination assay where the samples described in Example 2 were exposed to RNase digestion prior to loading on the gel.

FIG. 3A shows an ethidium bromide stained gel of the transformed *E. coli* cell lysate samples purified as described in Example 3. FIG. 3B shows the results of a DNA contamination assay where the samples described in Example 3 were exposed to RNase digestion prior to loading on the gel.

FIG. 4A shows an ethidium bromide stained gel of the rat liver cell lysate samples purified as described in Example 4. FIG. 4B shows the results of a DNA contamination assay where the samples described in Example 4 were exposed to RNase digestion prior to loading on the gel.

FIG. 5A shows an ethidium bromide stained gel of the bovine liver cell lysate samples purified as described in Example 6. FIG. 5B shows the results of a DNA contamination assay where the samples described in Example 6 were exposed to RNase digestion prior to loading on the gel.

FIG. 7A shows an ethidium bromide stained gel of the cow spleen cell lysate samples purified as described in Example 8. FIG. 7B shows the results of an assay used to determine if DNA and/or RNA is present in various samples as described in Example 8. FIG. 7C shows the results of a DNA contamination assay described in Example 8.

FIGS. 9A and 9B show the results of Example 11 which describes the use of zeolite membranes, silica-zeolite composite membranes, and silica-zeolite composite in solution to remove DNA from RNA in tissue sample purifications.

FIGS. 10A, 10B, and 10C show the results of Example 12, which describes methods used to screen various zeolites to determine their nucleic acid purification properties.

FIGS. 11A, 11B, and 11C show the results of Example 14, which describes the use of $Fe_3O_4$ particles coated with zeolite and MagneSil® particles coated with zeolite to purify RNA from lysate.

FIGS. 14A and 14B show the results of Example 17, which describes various pH ranges for citrate buffer that are effective for purifying RNA with zeolites.

FIG. 17 shows the results of Example 20, which describes the use of zeolites and acetate buffer for generating purified RNA samples.

FIG. 20 shows the results of Example 23, which describes the binding of zeolite 13X to a mixture of double stranded 35 bp DNA, single stranded 35 base DNA, single stranded 30 base DNA, 25 bp double stranded RNA, 25 base single stranded RNA and 21 base single stranded RNA, and elutions of the bound oligonucleotides.

DEFINITIONS

Figure 6:
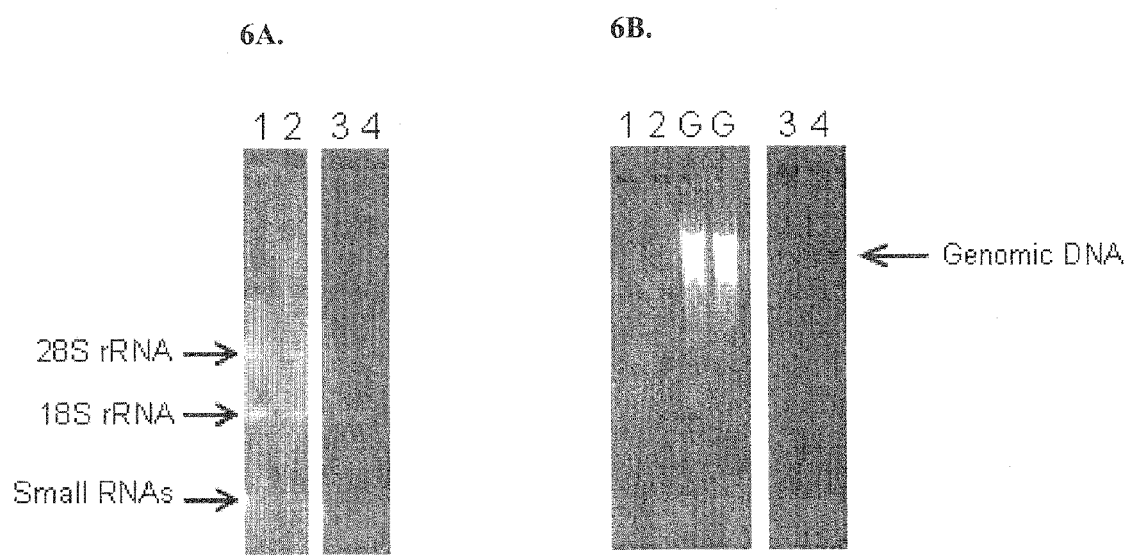
FIG. 6A shows an ethidium bromide stained gel of the human blood cell lysate samples purified as described in Example 7.
FIG. 6B shows the results of a DNA contamination assay where the samples described in Example 7 were exposed to RNase digestion prior to loading on the gel.

To facilitate an understanding of the invention, a number of terms are defined below.

As used herein, the phrase "a sample that comprises DNA and RNA molecules" is used to refer to any type of sample, such as biological or environmental samples, that includes a detectable quantity of both DNA and RNA molecules. Examples of such samples include, but are not limited to, a cell lysate, a previously purified RNA sample that still contains detectable quantities of DNA molecules, a RNA control sample, products of an in vitro transcription/translation reaction, or products of an in vitro translation reaction.

As used herein, the phrase "a sample that comprises DNA and a target molecule" is used to refer to any type of sample, such as a biological or environmental sample, that includes a detectable quantity of DNA and the target molecule. Examples of such target molecules in a sample include, but are not limited to a pharmaceutical drug preparation, a protein preparation, a lipid preparation, any reaction mixture where the presence of DNA is undesirable.

As used herein, a dilution buffer is said to have "an acidic pH" when the pH of the dilution buffer is less than 7.0. In preferred embodiments, the pH is less than 6.0, and more preferably is between about 3.0 and 5.3, or between about 4.0 and 5.0, although lower pH values are contemplated.

As used herein, the phrase "binding matrix that preferentially binds DNA molecules," refers to any type of substrate, whether porous or non-porous, that, in the presence of a buffer with an acidic pH and a sample containing both DNA and RNA molecules, binds readily to the DNA molecules present in the sample, but that has limited or no binding to the RNA molecules present in the sample. In certain embodiments, such binding matrices bind DNA molecules 10 times as readily as they binding RNA molecules (e.g. a 10/1 DNA to RNA ratio), while in other embodiments, the binding matrices bind DNA molecules 20 times, 50 times, or 100 times as readily as they bind RNA molecules (e.g. 20/1, 50/1, or 100/1 DNA to RNA ratio). Examples of such binding matrices include, but are not limited to, zeolite membranes, acid zeolite membranes, binding particles, a composition coated with binding particles (e.g. silica membrane coated with binding particles, magnetic particles coated with binding particles, silica membrane coated with zeolite, magnetic particles coated with zeolite, glass bubbles, zirconia, or alumina coated with binding particles, glass bubbles, zirconia, or alumina coated with zeolite), and a solid support.

As used herein, the phrase "binding particles that preferentially bind DNA molecules" refers to any type of small particles (e.g. micrometer range) that are porous or non-porous and that have the ability to serve as a binding matrix that preferentially binds DNA molecules. Examples of such binding particles include, but are not limited to, silica gel, sol gel, glass, powdered glass, quartz, alumina, zeolite particles, zirconium dioxide, and tectosilicates. In preferred embodiments, the binding particles comprise synthetic molecular sieve zeolites, preferably Type 13X or Type 3A.

As used herein, the phrase "binding matrix that preferentially binds RNA molecules," refers to any type of substrate, whether porous or non-porous, that, in the presence of a buffer with an acidic pH and a sample containing both DNA and RNA molecules, binds readily to the RNA molecules present in the sample, but that has limited or no binding to the DNA molecules present in the sample. In certain embodiments, such binding matrices bind RNA molecules 10 times as readily as they binding DNA molecules (e.g. a 10/1 RNA to DNA ratio), while in other embodiments, the binding matrices bind RNA molecules 20 times, 50 times, or 100 times as readily as they bind DNA molecules (e.g. 20/1, 50/1, or 100/1 RNA to DNA ratio). Examples of such binding matrices include, but are not limited to, titanium oxide particles.

As used herein, the phrase "binding particles that preferentially bind RNA molecules" refers to any type of small particles (e.g. micrometer range) that are porous or non-porous and that have the ability to serve as a binding matrix that preferentially binds RNA molecules.

As used herein, a purified RNA sample or purified RNA preparation is considered "substantially DNA-free" when, of all the nucleic acid present in the sample, less than 1.0% of the total mass of nucleic acid is DNA (i.e. at least 99.1% of the total mass of the nucleic acid present is RNA). The mass of nucleic acid present may be determined by mass spectrometry or other methods used to determine mass.

As used, herein, a purified RNA sample or purified RNA preparation is considered "essentially DNA-free" when, of all the nucleic acid present in the sample, less than 0.25% of the total mass of nucleic acid is DNA (i.e. at least 99.76% of the total mass of the nucleic acid present is RNA). The mass of nucleic acid present may be determined by mass spectrometry or other methods used to determine mass.

As used herein, a purified DNA sample or purified DNA preparation is considered "substantially RNA-free" when, of all the nucleic acid present in the sample, less than 1.0% of the total mass of nucleic acid is RNA (i.e. at least 99.1% of the total mass of the nucleic acid present is DNA). The mass of nucleic acid present may be determined by mass spectrometry, UV absorption methods, or other methods used to quantitate nucleic acid molecules.

As used, herein, a purified DNA sample or purified DNA preparation is considered "essentially RNA-free" when, of all the nucleic acid present in the sample, less than 0.25% of the total mass of nucleic acid is RNA (i.e. at least 99.76% of the total mass of the nucleic acid present is DNA). The mass of nucleic acid present may be determined by mass spectrometry, UV absorption methods, or other methods used to quantitate nucleic acid molecules.

DESCRIPTION OF THE INVENTION

The present invention relates to methods, kits, and compositions for generating purified RNA samples and purified DNA samples. In particular, the present invention provides methods for generating a purified RNA or DNA sample from a sample containing both DNA and RNA molecules using a binding matrix that preferentially binds DNA or RNA in the presence of an acidic dilution buffer, or using a binding matrix that comprises acid zeolites, as well as compositions and kits for practicing such methods.

I. Nucleic Acid Purification with a Binding Matrix

The compositions and methods of the present invention allow purified RNA and DNA samples to be prepared that contain very low levels of DNA or RNA contamination, yet provide a high yield of RNA or DNA to be purified from the original sample. For example, as shown in Example 6 below, the present invention provides a level of RNA purity superior than can be achieved with standard TRIzol reagent purification. This surprising level of purification, without the need for time consuming and extensive processing of samples satisfies the need in the art for highly purified RNA samples. For example, procedures in the art such as RT-PCR or quantitative RT-PCR, or other procedures that benefit from highly purified RNA, should greatly benefit from the present invention.

RNA or DNA may be isolated and purified according to the present invention from any type of nucleic acid preparation, biological sample, cell lysate, tissue culture, tissue homogenate, or any other type of sample that contains both DNA and RNA molecules. Exemplary samples include, but are not limited to, blood, urine, endocrine fluid, tissues, cells, and lysates of tissues or cells. In certain preferred embodiments, the sample comprises a cell lysate.

Cell lysates may be prepared, for example, by methods known in the art. Generally, a cell suspension, tissue, organ, plant leaves, or other source of cells is mixed with a lysis buffer comprising a chaotropic salt in order to rupture the cells. The mixture is rapidly homogenized, using, for example, a hand held homogenizer or an automatic homogenizer, such as a Waring blender, a Polytron tissue homogenizer, or the like.

The present invention is not limited to any specific type of lysis buffer. Preferably, the lysis buffer contains a chaotropic salt, present in about a 1-5 M concentration. Chaotropic salts are salts of chaotropic ions. Such salts are highly soluble in aqueous solutions. The chaotropic ions provided by such salts, at sufficiently high concentration in aqueous solutions of proteins or nucleic acids, cause proteins to unfold, nucleic acids to lose secondary structure or, in the case of double-stranded nucleic acids, to melt. Chaotropic ions include, for example, guanidinium, iodide, perchlorate and trichloroacetate. In preferred embodiments, the chaotropic ion is the guanidinium ion. Examples of chaotropic salts include, for example, guanidine hydrochloride, guanidine thiocyanate (which is sometimes referred to as guanidine isothiocyanate), sodium iodide, sodium perchlorate, and sodium trichloroacetate. Preferred are the guanidinium salts, more preferably guanidine hydrochloride or guanidine thiocyanate, but most preferably guanidine thiocyanate (GTC).

In certain embodiments that employ an acidic dilution buffer, after the cells are lysed (if the original sample contains cells) the sample containing both DNA and RNA molecules is contacted with a dilution buffer with an acidic pH, as well as with a binding matrix (e.g. binding particles) that preferentially binds DNA. The binding matrix is added to the sample at a level such that substantially all of the DNA (or all of the RNA) present in the sample can be bound by the binding particles to create a DNA-bound binding matrix (e.g. DNA-bound binding particles), or to create a RNA-bound binding matrix. In certain embodiments where binding particles are employed, the binding particles are provided at about 0.01-1.0 grams per milliliter of sample. Additional details regarding binding matrices are provided in part II below.

With regard to the dilution buffer, this solution may be used to dilute the original sample. The dilution buffer preferably contains water, salt, and a buffer and, in certain embodiments, has a pH of less than 7.0 (e.g. 6.9 or less). While the present invention is not limited to any particular acidic dilution buffer, the dilution buffer preferably comprises a citrate buffer composed of sodium citrate, sodium chloride, and water, at an acidic pH. The pH may be adjusted below 7.0 by using a concentrated acid such as HCl.

In certain embodiments, a heating step is employed. In such embodiments, the original sample containing DNA and RNA molecules (e.g. cell lysate) is heated to a temperature between 30-80 degrees Celsius (e.g. in a hybridization oven) prior to, or after, the addition of the dilution buffer and binding matrix.

The sample (now containing a binding matrix, and in certain embodiments, an acidic dilution buffer) is then subjected to a process that removes the DNA-bound binding matrix (or RNA-bound binding matrix), as well as any cellular debris that may also be present in the sample. Any type of method may be used, including methods known in the art for separating cellular debris. For example, the sample may be subjected to centrifugation such that a pellet forms that can then be removed. The DNA-bound binding matrix (or RNA-bound binding matrix), such as binding particles, and cellular debris (if present) can also be removed by filtering. In other embodiments, the DNA-bound binding matrix (or RNA-bound binding matrix), such as magnetic binding particles, and cellular debris (if present) can also be removed by magnetic separation (see, e.g., U.S. Pat. Nos. 6,673,631 and 6,194,562, both of which are herein incorporated by reference). For example, a clearing column containing a membrane (e.g, paper or silica membrane) may be used. Also for example, if the binding matrix is a membrane coated with binding particles, the membrane can simply be removed from the sample. The result of this filtration, centrifugation, magnetic separation or other removal techniques is a purified RNA sample (or purified DNA sample).

In certain embodiments, such as those relating to RNA purification, the purified RNA sample is further processed to further purify the RNA molecules away from any remaining contaminants. In certain preferred embodiments, the purified RNA sample is mixed with an alcohol (e.g., isopropanol) and then exposed to an RNA binding component (e.g. silica membrane, poly-T coated surface, etc.) such that RNA binds to the RNA binding component. In certain preferred embodiments, a binding column is employed (e.g. with a silica membrane). A description of such binding columns is provided in U.S. Pat. No. 6,218,531, herein incorporated by reference in its entirety. In certain embodiments, the RNA binding component is washed with a wash solution to remove salts and other debris. The RNA can be eluted from the RNA binding component using standard methods. For example, nuclease free water may be employed to elute the bound RNA molecules such that a purified RNA preparation is generated.

II. Binding Matrices

The present invention is not limited by the type of binding matrices that are employed. Instead, any type of binding matrices that preferentially binds DNA molecules (e.g. zeolites, acid zeolites, etc.), or that preferentially binds RNA molecules (e.g. titanium oxide) in the presence of an acidic dilution buffer may be employed. In preferred embodiments, the binding matrix comprises binding particles. Preferably the binding particles are micrometer is size (e.g. between 0.1 and 1000 µm in size). In preferred embodiments, the binding particles are less than about 20 µm in size and in particularly preferred embodiments, the binding particles are less than 10 µm in size (e.g. less than 10 µm in any planar dimension).

The binding matrices of the present invention may be porous or non-porous. Preferably the binding matrices contain pores that are between about 1 and 20 Å in size. In particularly preferred embodiments, the pores are about 9-11 Å in size (e.g. about 10 Å).

The binding matrices may be composed of any type of material. Examples of such materials include, but are not limited to, silica gel, sol gel, glass, powdered glass, quartz, alumina, zeolite particles, titanium dioxide, zirconium dioxide, and tectosilicates. Additional binding particles are described in U.S. Pat. No. 5,155,018 to Gillespie et al. and U.S. Pat. No. 6,180,778 to Bastian et al., both of which are herein incorporated by reference in their entireties for all purposes. In certain preferred embodiments, the binding matrices are zeolite particles (e.g. zeolite particles with pores).

The zeolites are framework silicates and are generally composed of interlocking tetrahedrons of $SiO_4$ and $AlO_4$. In general, the ratio of (Si+Al)/O in a zeolite equals approximately 1/2. The alumino-silicate structure is negatively charged and attracts the positive cations that reside within. Unlike most other tectosilicates, zeolites have large vacant spaces or cages in their structures that allow space for large cations such as sodium, potassium, barium and calcium and even relatively large molecules and cation groups such as water, ammonia, carbonate ions, nitrate ions, and other molecules. In certain zeolites, the spaces are interconnected and form long wide channels of varying sizes depending on the mineral. These channels allow the easy movement of the resident ions and molecules into and out of the structure. Zeolites are characterized by their ability to lose and absorb water without damage to their crystal structures.

There are currently about 45 natural minerals that are recognized members of the zeolite group. Industrially speaking, the term zeolite includes natural silicate zeolites, synthetic materials and phosphate minerals that have a zeolite like structure. The complexity of this combined group is extensive with over 120 structural variations. Exemplary members of the zeolite group include the following: The Analcime Family: Analcime, Pollucite, Wairakite, Bellbergite, Bikitaite, Boggsite, and Brewsterite; The Chabazite Family: Chabazite, Willhendersonite, Cowlesite, Dachiardite, Edingtonite, Epistilbite, Erionite, Faujasite, and Ferrierite; The Gismondine Family: Amicite, Garronite, Gismondine, Gobbinsite, Gmelinite, Gonnardite, and Goosecreekite; The Harmotome Family: Harmotome, Phillipsite, and Wellsite; The Heulandite Family: Clinoptilolite, Heulandite, Laumontite, Levyne, Mazzite, Merlinoite, Montesommaite, and Mordenite; The Natrolite Family: Mesolite, Natrolite, Scolecite, Offretite, Paranatrolite, Paulingite, and Perlialite; The Stilbite Family: Barrerite, Stilbite, Stellerite, Thomsonite, Tschernichite, and Yugawaralite.

There are also many different synthetic zeolites. One type of synthetic zeolite is the molecular sieve zeolites. Examples of these zeolites include Type 3A (3 Å pore size), Type 4A (4 Å pore size), Type 5A (5 Å pore size) and Type 13X (10 Å pore size). In preferred embodiments, the binding particles of the present invention comprise Type 13X zeolites. In other preferred embodiments, the binding particles of the present invention comprise Type 3A zeolites.

In certain embodiments, the binding matrix comprises acid zeolites. Under certain acidic conditions, the cation in a zeolite may be replaced by a proton, producing an "acid zeolite" (Armengol, Corma Garcia and Primo, (1995) Applied Catalysis A General, 126, p. 391-399; see also Climent et al., Applied Catalysts A: General 130, 5-12, 1995, both of which are herein incorporated by reference.) Acid zeolites are generally considered crystalline alumino-silicates with a high internal surface area (approx. 1000 $m^2/g$), containing acidic hydroxyl (O—H) groups located in nanometer micropores (See, e.g., J. M. Thomas, Scient. Am. 266(IV)(1992)82, pgs. 112-118, herein incorporated by reference). The degree of acidity of the acid zeolite and the reaction conditions has been shown to affect Freidel-Crafts alkylation of benzene and toluene with cinnamyl alcohol (Armengol et al (1995) above). In certain embodiments, the acid zeolite is ZSM-5 or similar acid zeolite.

Acid zeolites can be generated from zeolites by high temperature reactions. For example, a zeolite sample can be calcined to remove the organic cation. Zeolites can be placed inside a tube furnace on top of a frit in the middle of the tube, and spread out to maximize the surface area. One can then fit a ground glass elbow at each end, one attached to a nitrogen cylinder and the other immersed in a beaker of water, to regulate the flow of nitrogen gas. The zeolite can be slowly heated in the tube to 500° C. in increments of 50 to 100° C., with water vapor being released, then in increments of 100 to 500° C. This heating can be conducted for two hours after reaching temperature, where the tetrapropylammonium bromide will decompose to tripropylamine, propylene, and water. Any sodium ions remaining in the zeolite will now be ion exchanged for protons to fully convert the zeolite to the acid form.

The zeolites thus may be converted to their acid zeolite matrices through the use of an acidic buffer and method of treatment, as determined using screening methodology, such as that described in Example 12 below. The treatment may include the use of guanidine as an additive to the acidic buffer, or a heat treatment step, in the method of obtaining an acid zeolite particle, membrane, or magnetic acid zeolite particle. After the treatment, the acidic buffer is removed, leaving the acid zeolite matrix. The acid zeolite matrix is then used to purify RNA from a mixture of RNA and DNA in a liquid solution, thereby removing substantially all of the DNA. The liquid solution does not need to be at an acidic pH for the acid zeolite matrix to preferentially remove DNA from the sample. The sample may also be a mixture of protein and DNA, as described in Example 19, or may be a mixture of DNA and a pharmaceutical drug.

Zeolites have many minerals that have similar cage-like framework structures or have similar properties and/or are associated with zeolites, but that are not specifically classified as zeolites. Examples of these include the phosphates: kehoeite, pahasapaite and tiptopite; and the silicates: hsianghualite, lovdarite, viseite, partheite, prehnite, roggianite, apophyllite, gyrolite, maricopaite, okenite, tacharanite and tobermorite.

Under certain acidic conditions, the cation may be replaced by a proton, producing an "acid zeolite" (Armengol, Corma Garcia and Primo, (1995) Applied Catalysis A General, 126, p. 391-399.). The degree of acidity of the acid zeolite and the reaction conditions has been shown to affect Freidel-Crafts alkylation of benzene and toluene with cinnamyl alcohol (Armengol et al (1995) above).

Another class of mineral that the binding particles of the present invention may be composed of are the tectosilicates. This subclass is often called the "Framework Silicates" because its structure is composed of interconnected tetrahedrons going outward in all directions forming an intricate framework analogous to the framework of large building. In this subclass all the oxygens are shared with other tetrahedrons giving a silicon to oxygen ratio of approximately 1:2.

In order to determine if a certain type of matrix may serve as a useful binding matrix in the methods of the present invention, one can screen the candidate matrices in methods similar to Example 12 or Examples 1-7 below or as described in the following exemplary protocol. First a cell lysate is prepared by homogenizing a tissue or cell sample in Lysis Buffer (e.g., 4M guanidine thiocyanate, 10 mM Tris, pH 7.5, with beta-mercaptoethanol) with a rotor/stator homogenizer. The lysate is placed in two separate tubes, with one of the tubes being left as a lysate (control) and one of the tubes further processed as follows.

An acidic dilution buffer (e.g., 3M NaCl, 0.3M $Na_3$ citrate.$2H_2O$, 0.2% SDS, 0.0009% Blue dye (FD&C Blue #1), adjusted to a final pH of 4.0 with concentrated hydrochloric acid (HCl)) is then added to the one tube containing the lysate to be further processed at a ratio of 2:1 (v/v). The sample in the tube is then mixed by inversion until homogeneous. The tube is incubated at about 50-70° C. in a hybridization oven for about 3 minutes and then placed at ambient temperature. The candidate binding matrix, which may be binding particles, are then weighed and added to the tube at a ratio of about 0.25 g per ml of lysate volume. This mixture is then shaken vigorously and poured into a clearing column (e.g. Promega PureYield™ Clearing Column), nested in a 50 ml collection tube. The column is then centrifuged at 2,000× g, at 23° C. for about 10 minutes. If the candidate binding matrix is able to serve as a successful binding matrix according to the present invention, the lysate should contain RNA and will be captured in the 50 ml collection tube, while the sample debris, and DNA bound binding matrix will be captured by the clearing column membrane and can be discarded with the clearing column.

The lysate is further processed as follows prior to performing the assays to determine if the candidate binding matrix was in fact successful at preferentially binding the DNA. Isopropanol is added to the cleared lysate at a volume equal to the added dilution buffer volume. The sample is mixed and then immediately applied to a binding column (e.g. Promega PureYield™ Binding Column), attached to a vacuum manifold with a vacuum of approximately 15 in. Hg which will cause the sample to pass through the column leaving RNA present in the sample bound to the binding column membrane. The membrane is then washed twice with 10 ml and then 20 ml of Wash Solution (e.g., 60 mM potassium acetate, 10 mM Tris, pH 7.5, 60% ethanol) to remove impurities and salts. The membrane is then vacuum dried for 3 minutes on a vacuum manifold. The binding column is then transferred to 50 ml collection tubes for elution with nuclease-free water. The column assembly is then centrifuged (e.g, using a swinging bucket rotor) at 2,000×g for 2 minutes to collect RNA that may be bound to the membrane. The elution steps are then repeated, with an additional 1 ml of nuclease-free water.

The purified sample, as well as the unprocessed original lysate sample, are then analyzed for both RNA and DNA content. In particular, these samples are analyzed by gel electrophoresis on a native, 1% agarose, 1×TBE gel, stained with ethidium bromide (e.g. as described in the Examples below). This gel indicates the total amount of nucleic acid in each sample. A second gel is then run to determine what percent, if any, of the nucleic acid visualized in the first gel is DNA contamination instead of the desired RNA. Samples are digested with RNase (e.g. Promega's RNase ONE™ Ribonuclease, Cat. #M4265). The digestions are incubated at 37° C. for 1 hour and then held at 4° C. The digests are then analyzed by electrophoresis on a native, 1% agarose, 1×TBE gel, stained with ethidium bromide. The results of this second gel indicate the amount of DNA that is present in the samples.

The success of the candidate binding matrix can be determined by reviewing each of these gels. Preferably, the second gel contains less than about 1% DNA compared to the total amount of RNA present as visualized in the first gel. Particularly preferred binding matrices are identified when there is no easily visualized DNA present in the treated sample lane in the second gel, yet there is a substantial amount of nucleic acid in the first gel compared to the untreated lysate.

The above exemplary screening procedure may also be employed to screen candidate acidic dilution buffers. For example, one could use a binding agent known to preferentially bind DNA in the protocol described above, but substitute in a candidate acidic dilution buffer (e.g. to test different buffers as well as different pH's). In this regard, the two gels that result could be analyzed to determine if a given candidate dilution buffer is suitable for use with the methods of the present invention.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); Xg (time gravity); and C (degrees Centigrade).

Example 1

Isolation of Total RNA from Human Cells

This example describes the purification of total RNA from human HEK293T cells. Human HEK293T cells were cultured in monolayers under standard conditions in flasks. The cells were trypsinized, washed and harvested by centrifugation. Cell pellets were flash frozen in a dry ice/ethanol bath. The cell pellets were stored at −70° C. until use.

A tube containing a pellet of ~6×10$^8$ cells was placed on dry ice. Twelve ml of 4° C. Lysis Buffer (4M guanidine thiocyanate, 10 mM Tris, pH 7.5, with beta-mercaptoethanol added separately to a final concentration of 0.974% (v/v)) was immediately added to the tube, after it was transferred to ice. The cell pellet was disrupted and the cells were lysed by homogenization with a Tissue-Tearor™ rotor/stator homogenizer (Biospec Products, Inc., Bartlesville, Okla.). The sample was homogenized 2-3 times until the pellet was no longer visible. In this Example, 5 ml of a previously prepared lysate was combined with the freshly prepared lysate, to increase the amount of lysate available. The added lysate was prepared using the same procedure, stored at −70° C. and then thawed at 4° C. before use. The combined lysate was divided into four 2 ml and four 1 ml aliquots to isolate RNA from ~1×10$^8$ and ~5×10$^7$ cells per prep, respectively. An additional 1 ml of Lysis Buffer was added to the 1 ml samples. Plastic, 15 ml, screw capped tubes were used. The samples were divided into two sets, designated "1MIX" and "2MIX", to test a variation on mixing in this Example.

The 1 MIX samples were processed as follows. Four ml of Dilution Buffer (3M NaCl, 0.36M Na$_3$ citrate.2H$_2$O, 0.0009% Blue dye (FD&C Blue #1), adjusted to a final pH of 4.0 with concentrated hydrochloric acid (HCl)) was added to each quadruplicate sample of 2 ml of lysate, without mixing. One ml of Clearing Agent (2M NaCl, 0.1 mM EDTA (pH 8.0), 0.45 g/ml Molecular Sieves, type 13X (zeolite) binding particles) was added to each sample. The samples were then mixed by inversion and vortexing, until homogeneous. These four samples were designated "1MIX".

The 2MIX samples were processed as follows. Four ml of Dilution Buffer (3M NaCl, 0.36M Na$_3$ citrate.2H$_2$O, 0.0009% Blue dye (FD&C Blue #1), adjusted to a final pH of 4.0 with concentrated hydrochloric acid (HCl)) was added to each quadruplicate 2 ml of lysate and mixed by inversion and vortexing, until homogeneous. One ml of Clearing Agent (2M NaCl, 0.1 mM EDTA (pH 8.0), 0.45 g/ml Molecular Sieves, type 13X (zeolite)) was added to each sample and mixed by inversion and vortexing, until homogeneous. These four samples were designated "2MIX" for "2 Mixes".

The "1MIX" and "2MIX" samples were incubated at 70° C. in a hybridization oven for 5 minutes and then placed at ambient temperature (23° C.). The remaining steps were performed at ambient temperature (23° C.). Each mixture was applied to a Promega clearing column (Promega PureYield™ Clearing Column; which has a cellulose membrane) in a 50 ml collection tube and centrifuged at 2,000×g for 10 minutes in a swinging bucket rotor to clear the lysates. The cleared lysates, containing RNA, were captured in the collection tubes. The sample debris, binding particles and DNA were captured by the clearing column membrane and were discarded with the clearing columns.

Four ml of isopropanol was added to each cleared lysate and mixed by swirling the tube. Each mixture was applied to a Promega binding column (Promega PureYield™ Binding Column; which has a silica membrane), attached to a vacuum manifold. A vacuum of approximately 15 in. Hg was applied to the columns. Each sample passed through the column, leaving the RNA bound to the binding column membrane. The membranes were washed twice with 20 ml and then 10 ml of Wash Solution (60 mM potassium acetate, 10 mM Tris, pH 7.5, 60% ethanol) to remove impurities and salts. The membranes were vacuum dried for 3 minutes on the vacuum manifold. The binding columns were transferred to 50 ml collection tubes for elution. One ml of nuclease-free water was applied to each membrane and incubated for 2 minutes at 23° C. The column assemblies were centrifuged, using a swinging bucket rotor, at 2,000×g for 2 minutes to collect the purified total RNA. The elution steps were repeated, with an additional 1 ml of nuclease-free water. The second eluates were collected in fresh 50 ml tubes. The purified total RNA samples were analyzed by spectrophotometry and agarose gel analysis. Total RNA yields were determined by absorbance at 260 nm. The results are shown in Table 1 and FIGS. 1A and 1B.

TABLE 1

Total RNA Yield from Tissue Culture Cells

| Sample ID | Total RNA Yield Elution 1 (μg) | Total RNA Yield Elution 2 (μg) | Total RNA Yield Elution 1 + 2 (μg) |
|---|---|---|---|
| 1E8 1MIX 1 | 808.9 | 198.0 | 1006.9 |
| 1E8 1MIX 2 | 909.2 | 155.3 | 1064.5 |
| 1E8 2MIX 1 | 899.9 | 188.7 | 1088.6 |
| 1E8 2MIX 2 | 929.5 | 199.7 | 1129.2 |
| 5E7 1MIX 1 | 473.5 | 76.1 | 549.6 |
| 5E7 1MIX 2 | 445.2 | 60.8 | 506.0 |
| 5E7 2MIX 1 | 444.0 | 42.4 | 486.4 |
| 5E7 2MIX 2 | 450.6 | 43.5 | 494.1 |

FIG. 1A show the RNA samples analyzed by electrophoresis on a native, 1% agarose, 1×TBE gel, stained with ethidium bromide. Ten μl of each sample was loaded per lane. The image in FIG. 1A was collected using an Alpha Innotech FluorChem™ Imaging System. Lanes 1-8 show the Elution 1 results and Lanes 9-16 show the Elution 2 results. Lanes 1 and 9 contain 1E8 1MIX 1; Lanes 2 and 10 contain 1E8 1MIX 2; Lanes 3 and 11 contain 1E8 2MIX 1; Lanes 4 and 12 contain 1E8 2MIX 2; Lanes 5 and 13 contain 5E7 1MIX 1; Lanes 6 and 14 contain 5E7 1MIX 2; Lanes 7 and 15 contain 5E7 2MIX 1; Lanes 8 and 16 contain 5E7 2MIX 2; Lane M contains Promega's 1 kb DNA Ladder (Cat. #G5711), 10,000 bp, 8,000 bp, 6,000 bp, 5,000 bp, 4,000 bp, 3,000 bp, 2,500 bp, 2,000 bp, 1,500 bp, 1,000 bp, 750 bp, 500 bp, 253 bp and 250 bp. Representative size markers are indicated in this figure. The undenatured 28S ribosomal RNA, 18S ribosomal RNA and small RNAs are indicated by arrows in this figure.

FIG. 1B depicts the results of a DNA Contamination Assay. The purified total RNA samples were digested with Promega's RNase ONE™ Ribonuclease (Cat. #M4265). A 15 μl digestion mix, consisting of 3 μl of 10× Reaction Buffer, 9 μl of Nuclease-Free Water and 3 μl of RNase ONE™ Ribonuclease (5-10 u/μl) was mixed with 15 μl of each total RNA sample. The digestions were incubated at 37° C. for 1 hour and then held at 4° C. until analyzed. The digests were analyzed by electrophoresis on a native, 1% agarose, 1×TBE gel, stained with ethidium bromide. Ten μl of each reaction was loaded per lane. The image in FIG. 1B was collected using an Alpha Innotech FluorChem™ Imaging System. The lanes are the same as indicated for FIG. 1A. Representative size markers are indicated. Note that the size markers were affected by diffusion of salt from the digests.

Example 2

Isolation of Total RNA from Cow Spleen Cells

This example describes the isolation of total RNA from cow spleen cells. A cow spleen lysate was prepared by homogenizing frozen tissue in 4° C. Lysis Buffer (4M guanidine thiocyanate, 10 mM Tris, pH 7.5, with beta-mercaptoethanol added separately to a final concentration of 0.974% (v/v)) with a PRO 200 rotor/stator homogenizer (PRO Scientific, Inc., Oxford, Conn.). The lysate was prepared at a concentration of 150 mg/ml (wet weight) and was stored in 10 ml aliquots at −70° C., until use. The frozen lysate was thawed at 4° C. and pooled. Two 2 ml aliquots were dispensed into two plastic, 50 ml, screw capped tubes. These two samples were designated "DB4-" to indicate that the lysate was not further processed. The remainder of the cow spleen lysate was rehomogenized to eliminate the particulates that were observed. This rehomogenized lysate was dispensed into eight 2 ml aliquots. Two of the samples were designated "DB4 R" for "rehomogenized lysate" (2 ml). Additional 4° C. Lysis Buffer was added to select samples, such that the final lysate volumes were increased in duplicate to 3 ml, 4 ml and 5 ml per tube. Each tube contained 300 mg of cow spleen, regardless of the final lysate concentration. Dilution Buffer (3M NaCl, 0.3M $Na_3$ citrate.$2H_2O$, 0.2% SDS, 0.0009% Blue dye (FD&C Blue #1), adjusted to a final pH of 4.0 with concentrated hydrochloric acid (HCl)) was added to each lysate at a ratio of 2:1 (v/v) (i.e. 4 ml, 6 ml, 8 ml or 10 ml). The samples were mixed by inversion 3-4 times, until homogeneous. Each tube was incubated at 70° C. in a hybridization oven for 3 minutes and then placed at ambient temperature (23° C.). Molecular Sieves, Type 13X, <10 μm powder (zeolite) (binding particles) was weighed and added to each tube at a ratio of 0.25 g per ml of lysate volume (i.e. 0.5 g, 0.75 g, 1.0 g or 1.25 g). Each mixture was shaken vigorously and poured into a Promega clearing column (Promega PureYield™ Clearing Column), nested in a 50 ml collection tube. The columns were centrifuged in a swinging bucket rotor at 2,000×g, 23° C. for 10 minutes. The cleared lysates, containing RNA, were captured in 50 ml collection tubes. The sample debris, binding particles and DNA were captured by the clearing column membrane and were discarded with the clearing columns.

The following steps were performed at ambient temperature (23° C.). Isopropanol was added to each cleared lysate at a volume equal to the added Dilution Buffer volume (4 ml, 6 ml, 8 ml or 10 ml). Each sample was mixed and immediately applied to a Promega binding column (Promega PureYield™ Binding Column), attached to a vacuum manifold. A vacuum of approximately 15 in. Hg was applied to the columns. Each sample passed through the column, leaving the RNA bound to the binding column membrane. The membranes were washed twice with 10 ml and then 20 ml of Wash Solution (60 mM potassium acetate, 10 mM Tris, pH 7.5, 60% ethanol) to remove impurities and salts. The membranes were vacuum dried for 3 minutes on the vacuum manifold. The binding columns were transferred to 50 ml collection tubes for elution. One ml of nuclease-free water was applied to each membrane and incubated for 1 minute at 23° C. The column assemblies were centrifuged, using a swinging bucket rotor, at 2,000×g for 2 minutes to collect the purified total RNA. The elution steps were repeated, with an additional 1 ml of nuclease-free water. The second eluates were collected in fresh 50 ml tubes. The purified total RNA samples were analyzed by spectrophotometry and agarose gel analysis. Total RNA yields were determined by absorbance at 260 nm. The results are shown in Table 2 and FIGS. 2A and 2B.

TABLE 2

Total RNA Yield from 300 mg Cow Spleen

| Sample ID | Total RNA Yield Elution 1 (μg) | Total RNA Yield Elution 2 (μg) | Total RNA Yield Elution 1 + 2 (μg) |
|---|---|---|---|
| DB4 - 1 (2 ml Lysate) | 329.6 | 101.7 | 431.3 |
| DB4 - 2 (2 ml Lysate) | 343.9 | 97.3 | 441.2 |
| DB4 R 1 (2 ml Lysate) | 340.9 | 79.8 | 420.7 |
| DB4 R 2 (2 ml Lysate) | 332.1 | 100.4 | 432.5 |
| 3 ml 1 | 341.4 | 75.8 | 417.2 |
| 3 ml 2 | 371.9 | 53.1 | 425.0 |
| 4 ml 1 | 350.4 | 72.5 | 422.9 |
| 4 ml 2 | 334.6 | 86.5 | 421.1 |
| 5 ml 1 | 348.8 | 94.3 | 443.1 |
| 5 ml 2 | 376.2 | 66.9 | 443.1 |

FIG. 2A shows a gel analysis of purified total RNA from cow spleen. RNA samples were analyzed by electrophoresis on a native, 1% agarose, 1×TBE gel, stained with ethidium bromide. Ten μl of each sample was loaded per lane. The image was collected using an Alpha Innotech FluorChem™ Imaging System. Lanes 1-10 show the Elution 1 results and Lanes 11-20 show the Elution 2 results. Lanes 1, 11: DB4—1 (2 ml Lysate); Lanes 2, 12: DB4—2 (2 ml Lysate); Lanes 3, 13: DB4 R 1; Lanes 4, 14: DB4 R 2; Lanes 5, 15: 3 ml Lysate 1; Lanes 6, 16: 3 ml Lysate 2; Lanes 7, 17: 4 ml Lysate 1; Lanes 8, 18: 4 ml Lysate 2; Lanes 9, 19: 5 ml Lysate 1; Lanes 10, 20: 5 ml Lysate 2. The undenatured 28S ribosomal RNA, 18S ribosomal RNA and small RNAs are indicated by arrows.

FIG. 2B shows the results of a DNA contamination assay. Purified total RNA samples were digested with Promega's RNase ONE™ Ribonuclease (Cat. #M4265). A 20 μl digestion mix, consisting of 4 μl of 10× Reaction Buffer, 14 μl of Nuclease-Free Water and 2 μl of RNase ONE™ Ribonuclease (5-10 u/μl) was mixed with 20 μl of each total RNA sample. The digestions were incubated at 37° C. for 1 hour and then held at 4° C., until analyzed. The digests were analyzed by electrophoresis on a native, 1% agarose, 1×TBE gel, stained with ethidium bromide. Ten μl of each reaction was loaded per lane. The image was collected using an Alpha Innotech FluorChem™ Imaging System. Lanes 1-10 show the Elution 1 results and Lanes 11-20 show the Elution 2 results. Lanes 1, 11: DB4—1 (2 ml Lysate); Lanes 2, 12: DB4—2 (2 ml Lysate); Lanes 3, 13: DB4 R 1; Lanes 4, 14: DB4 R 2; Lanes 5, 15: 3 ml Lysate 1; Lanes 6, 16: 3 ml Lysate 2; Lanes 7, 17: 4 ml Lysate 1; Lanes 8, 18: 4 ml Lysate 2; Lanes 9, 19: 5 ml Lysate 1; Lanes 10, 20: 5 ml Lysate 2. Partially degraded total RNA from the RNase ONE™ Ribonuclease digestion is indicated in lanes 1-10 by an arrow.

Example 3

Isolation of Total RNA from Transformed *E. coli*

This example describes the isolation of total RNA from transformed *E. coli* cells. *E. coli* strain JM109, transformed with the high copy vector pGEM®-3Zf(+), was grown at 37° C. in Luria Bertani (LB) culture medium with 100 μg/ml ampicillin. An overnight culture was used to inoculate fresh medium and the cells were grown to an optical density of 0.69 at 600 nm, corresponding to approximately $1.7 \times 10^8$ cells/ml. The cells were harvested by centrifugation in tubes containing 40 ml aliquots of culture. The cell pellets were drained of medium and flash frozen in individual tubes in a dry ice/ethanol bath. The cell pellets, containing approximately $6.8 \times 10^9$ E. coli cells each, were stored at −70° C. until use.

Tubes containing the frozen cell pellets were thawed on ice. The pellets were gently resuspended by mixing. A freshly prepared lysozyme solution (10 mM Tris, 1 mM EDTA, (pH 7.5), 0.4 mg/ml lysozyme) was added at an amount of 0.7 ml per tube. This mixture was incubated at ambient temperature (23° C.) for 5 minutes to digest away the bacterial cell wall.

Two experiments were performed, isolating total RNA from ~$6.8 \times 10^9$ and ~$1 \times 10^{10}$ cells. In the first experiment, three tubes of cells (~$6.8 \times 10^9$ cells per tube) were thawed on ice for approximately 20 minutes and digested with lysozyme as described above. A total of 4 ml of 4° C. Lysis Buffer (4M guanidine thiocyanate, 10 mM Tris, pH 7.5, with beta-mercaptoethanol added separately to a final concentration of 0.974% (v/v)) was added to these three tubes of treated cells and combined. The treated cells were lysed by vigorously vortexing the tubes. The prepared lysate was dispensed into three 2 ml samples of ~$6.8 \times 10^9$ cells per isolation. Plastic 15 ml, screw capped tubes were used. One ml of Clearing Agent (2M NaCl, 0.1 mM EDTA (pH 8.0), 0.45 g/ml Molecular Sieves, type 13X (zeolite) type binding particles) was added to each tube containing 2 ml of lysate and mixed by vortexing. Four ml of Dilution Buffer (3M NaCl, 0.36M Na$_3$ citrate.2H$_2$O, 0.0009% Blue dye (FD&C Blue #1), adjusted to a final pH of 4.0 with concentrated hydrochloric acid (HCl)) was added to each tube. The mixture was shaken and vortexed to homogeneity. The tubes were incubated at 70° C. in a hybridization oven for 5 minutes and then cooled at ambient temperature (23° C.).

In the second experiment, three tubes of cells (~$6.8 \times 10^9$ cells per tube) were thawed on ice for approximately 10 minutes and digested with lysozyme as described above. A total of 2 ml of 4° C. Lysis Buffer (4M guanidine thiocyanate, 10 mM Tris, pH 7.5, with beta-mercaptoethanol added separately to 1%) was added to three tubes of treated cells and combined. The treated cells were lysed by vigorously vortexing the tubes. The prepared lysate was dispensed into two 2 ml samples of ~$1 \times 10^{10}$ cells each for RNA isolation. Plastic, 15 ml, screw capped tubes were used. Four ml of Dilution Buffer (3M NaCl, 0.36M Na$_3$ citrate.2H$_2$O, 0.0009% Blue dye (FD&C Blue #1), adjusted to a final pH of 4.0 with concentrated hydrochloric acid (HCl)) was added to each tube containing 2 ml of lysate and mixed by inversion and vortexing, until homogeneous. One ml of Clearing Agent (2M NaCl, 0.1 mM EDTA (pH 8.0), 0.45 g/ml Molecular Sieves, type 13X (zeolite) type binding particles) was added to each tube and mixed by inversion and vortexing, until homogeneous. The tubes were incubated at 70° C. in a hybridization oven for 5 minutes and then cooled at ambient temperature (23° C.).

The following steps were performed at ambient temperature (23° C.) for both experiments. The mixtures were applied to Promega clearing columns (Promega PureYield™ Clearing Column) in 50 ml collection tubes and centrifuged in a swinging bucket rotor at 2,000×g for 10 minutes to clear the lysates. The clearing agent, cellular debris and DNA were captured by the clearing column membrane and were discarded. The cleared lysate, containing RNA, was captured in the collection tube. Four ml of isopropanol was added to each tube of cleared lysate and mixed by swirling the tube. Each mixture was applied to a Promega binding column (Promega PureYield™ Binding Column), attached to a vacuum manifold. A vacuum of approximately 15 in. Hg was applied to the columns. Each sample passed through the column, leaving the RNA bound to the binding column membrane. The membranes were washed twice with 20 ml and then 10 ml of Wash Solution (60 mM potassium acetate, 10 mM Tris, pH 7.5, 60% ethanol) to remove impurities and salts. The membranes were vacuum dried for 3 minutes on the vacuum manifold. The binding columns were transferred to 50 ml collection tubes for elution. One ml of nuclease-free water was applied to each membrane and incubated for 1-2 minutes at 23° C. The column assemblies were centrifuged, using a swinging bucket rotor, at 2,000×g for 2 minutes to collect the purified total RNA. The elution steps were repeated, with an additional 1 ml of nuclease-free water. The second eluates were collected in fresh 50 ml tubes. The purified total RNA samples were analyzed by spectrophotometry and agarose gel analysis. Total RNA yields were determined by absorbance at 260 nm. The results are shown in Table 3 and FIGS. 3A and 3B.

TABLE 3

Total RNA Yield from Transformed E. coli Cells

| Sample ID | Total RNA Yield Elution 1 (μg) | Total RNA Yield Elution 2 (μg) | Total RNA Yield Elution 1 + 2 (μg) |
|---|---|---|---|
| EC 1 $6.8 \times 10^9$ cells | 640.8 | 156.6 | 797.4 |
| EC 1 $6.8 \times 10^9$ cells | 639.8 | 164.1 | 803.9 |
| EC 3 $6.8 \times 10^9$ cells | 587.1 | 158.0 | 745.1 |
| 1 $1 \times 10^{10}$ cells | 743.4 | 204.0 | 947.4 |
| 2 $1 \times 10^{10}$ cells | 822.0 | 189.6 | 1011.6 |

FIG. 3A shows a gel analysis of purified total RNA from transformed E. coli cells. RNA samples were analyzed by electrophoresis on a native, 1% agarose, 1×TBE gel, stained with ethidium bromide. Ten μl of each sample was loaded per lane. The image was collected using an Alpha Innotech Fluor Chem™ Imaging System. Panel 1 shows the Elution 1 results and Panel 2 shows the Elution 2 results. Lanes 1, 6: EC 1 $6.8 \times 10^9$ cells; Lanes 2, 7: EC 1 $6.8 \times 10^9$ cells; Lanes 3, 8: EC 3 $6.8 \times 10^9$ cells; Lanes 4, 9: 1 $1 \times 10^{10}$ cells; Lanes 5, 10: 2 $1 \times 10^{10}$ cells. Lane P: Promega's pGEM®-3Zf (+) Vector (circular) (Cat. #P2271), 2 μg. Lane M: Promega's 1 kb DNA Ladder (Cat. #G5711), 10,000 bp, 8,000 bp, 6,000 bp, 5,000 bp, 4,000 bp, 3,000 bp, 2,500 bp, 2,000 bp, 1,500 bp, 1,000 bp, 750 bp, 500 bp, 253 bp and 250 bp. Representative size markers are indicated. The undenatured 23S ribosomal RNA, 16S ribosomal RNA and small RNAs are indicated by arrows.

FIG. 3B shows a DNA Contamination Assay of Total RNA Purified from E. coli. Purified total RNA samples were digested with Promega's RNase ONE™ Ribonuclease (Cat. #M4265). A 15 μl digestion mix, consisting of 3 μl of 10× Reaction Buffer, 9 μl of Nuclease-Free Water and 3 μl of RNase ONE™ Ribonuclease (5-10 u/μl) was mixed with 15 μl of each total RNA sample. The digestions were incubated at 37° C. for 1 hour and then held at 4° C., until analyzed. The digests were analyzed by electrophoresis on a native, 1% agarose, 1×TBE gel, stained with ethidium bromide. Ten μl of each reaction was loaded per lane. The image was collected using an Alpha Innotech FluorChem™ Imaging System. Panel 1 shows the Elution 1 results and Panel 2 shows the Elution 2 results. Lanes 1, 6: EC 1 6.8×10$^9$ cells; Lanes 2, 7: EC 1 6.8×10$^9$ cells; Lanes 3, 8: EC 3 6.8×10$^9$ cells; Lanes 4, 9: 1 1×10$^{10}$ cells; Lanes 5, 10: 2 1×10$^{10}$ cells. Lane P: Promega's pGEM®-3Zf (+) Vector (circular) (Cat. #P2271), 2 μg. Lane G: Control samples containing genomic DNA. Lane M: Promega's 1 kb DNA Ladder (Cat. #G5711), 10,000 bp, 8,000 bp, 6,000 bp, 5,000 bp, 4,000 bp, 3,000 bp, 2,500 bp, 2,000 bp, 1,500 bp, 1,000 bp, 750 bp, 500 bp, 253 bp and 250 bp. Representative size markers are indicated.

Example 4

Isolation of Total RNA from Rat Liver

This example describes the isolation of total RNA from rat liver. A rat liver lysate was prepared by homogenizing frozen tissue in 4° C. Lysis Buffer (4M guanidine thiocyanate, 10 mM Tris, pH 7.5, with beta-mercaptoethanol added separately to a final concentration of 0.974% (v/v)) with a PRO 200 rotor/stator homogenizer (PRO Scientific, Inc., Oxford, Conn.). The lysate was prepared at a concentration of 150 mg/ml (wet weight) and was stored in 10 ml aliquots at −70° C., until use.

The frozen lysate was thawed at 4° C., pooled and dispensed into 2 ml aliquots. Plastic, 15 ml, screw capped tubes were used. Four ml of Dilution Buffer (3M NaCl, 0.3M Na$_3$ citrate.2H$_2$O, 0.2% SDS, 0.0009% Blue dye (FD&C Blue #1), adjusted to a final pH of 4.0 with concentrated hydrochloric acid (HCl)) was added to each sample and mixed by inversion 3-4 times, until homogeneous. The tubes were incubated at 70° C. in a hybridization oven for 3 minutes and then placed at ambient temperature (23° C.).

Molecular Sieves, Type 13X, powder (<10 μm) (zeolite) (binding agent) was weighed and added to each tube. Duplicate samples were isolated for each sample set: the amount of zeolite was varied from 0.25 g, 0.5 g, 0.75 g, 1.0 g, and 1.5 g per tube. Each mixture was shaken vigorously and immediately poured into a Promega clearing column (Promega PureYield™ Clearing Column), nested in a 50 ml collection tube. The columns were centrifuged in a swinging bucket rotor at 2,000×g, 23° C. for 10 minutes. The cleared lysates, containing RNA, were captured in 50 ml collection tubes. The cellular debris, binding particles and DNA were captured by the clearing column membrane and were discarded with the clearing columns. Two additional 0.5 g samples were cleared by high speed centrifugation, instead of using clearing columns. For these two samples (designated with an "S"), each mixture was vigorously shaken and poured into a 50 ml, polypropylene, Sepcor® centrifuge tube with cap (Labcor Products, Inc., Frederick, Md.). The lysates were cleared by centrifugation in a fixed angle rotor at 33,000×g, 20° C. for 10 minutes. The cleared lysates, containing RNA, were transferred to fresh tubes. The pellets, containing sample debris, DNA and binding particles, were discarded.

The following steps were performed at ambient temperature (23° C.). Four ml of isopropanol was added to each duplicate set of cleared lysates and mixed by inversion. Each mixture was applied to a Promega binding column (Promega PureYield™ Binding Column), attached to a vacuum manifold. A vacuum of approximately 15 in. Hg was applied to the columns. Each sample passed through the column, leaving the RNA bound to the binding column membrane. The membranes were washed twice with 10 ml and then 20 ml of Wash Solution (60 mM potassium acetate, 10 mM Tris, pH 7.5, 60% ethanol) to remove impurities and salts. The membranes were vacuum dried for 3 minutes on the vacuum manifold. The binding columns were transferred to 50 ml collection tubes for elution. One ml of nuclease-free water was applied to each membrane and incubated for 1 minute at 23° C. The column assemblies were centrifuged, using a swinging bucket rotor, at 2,000×g for 2 minutes to collect the purified total RNA. The elution steps were repeated, with an additional 1 ml of nuclease-free water. The second eluates were collected in fresh 50 ml tubes. The purified total RNA samples were analyzed by spectrophotometry and agarose gel analysis. Total RNA yields were determined by absorbance at 260 nm. The results are shown in Table 4 and FIGS. 4A and 4B.

TABLE 4

Total RNA Yield from 300 mg Rat Liver

| Sample ID | Total RNA Yield Elution 1 (μg) | Total RNA Yield Elution 2 (μg) | Total RNA Yield Elution 1 + 2 (μg) |
|---|---|---|---|
| 0.25 g Z3-1 | 1054.7 | 699.7 | 1754.4 |
| 0.25 g Z3-2 | 1141.2 | 652.9 | 1794.1 |
| 0.5 g Z3-1 | 1017.2 | 626.9 | 1644.1 |
| 0.5 g Z3-2 | 987.7 | 551.5 | 1539.2 |
| 0.75 g Z3-1 | 997.7 | 632.0 | 1629.7 |
| 0.75 g Z3-2 | 853.7 | 606.2 | 1459.9 |
| 1.0 g Z3-1 | 700.2 | 533.8 | 1233.8 |
| 1.0 g Z3-2 | 724.9 | 549.6 | 1274.5 |
| 1.5 g Z3-1 | 486.2 | 498.8 | 985.0 |
| 1.5 g Z3-2 | 728.5 | 469.0 | 1197.5 |
| 0.5 g Z3-1 S | 1040.9 | 617.7 | 1658.6 |
| 0.5 g Z3-2 S | 1028.6 | 564.2 | 1592.8 |

FIG. 4A shows a gel analysis of purified total RNA from rat liver. RNA samples were analyzed by electrophoresis on a native, 1% agarose, 1×TBE gel, stained with ethidium bromide. Ten μl of each sample was loaded per lane. The image was collected using an Alpha Innotech FluorChem™ Imaging System. Lanes 1-12 show the Elution 1 results and Lanes 13-24 show the Elution 2 results. Lanes 1, 13: 0.25 g Z3-1; Lanes 2, 14: 0.25 g Z3-2; Lanes 3, 15: 0.5 g Z3-1; Lanes 4, 16: 0.5 g Z3-2; Lanes 5, 17: 0.75 g Z3-1; Lanes 6, 18: 0.75 g Z3-2; Lanes 7, 19: 1.0 g Z3-1; Lanes 8, 20: 1.0 g Z3-2: Lanes 9, 21: 1.5 g Z3-1; Lanes 10, 22: 1.5 g Z3-2; Lanes 11, 23: 0.5 g Z3-1 S; Lanes 12, 24: 0.5 g Z3-2 S. Lane M: Promega's PCR Markers (Cat. #G3161), 1,000 bp, 750 bp, 500 bp, 300 bp, 150 bp and 50 bp. Representative size markers are indicated. The undenatured 28S ribosomal RNA, 18S ribosomal RNA and small RNAs are indicated by arrows.

FIG. 4B show the results of a DNA contamination assay. Purified total RNA samples were digested with Promega's RNase ONE™ Ribonuclease (Cat. #M4265). A 20 μl digestion mix, consisting of 4 μl of 10× Reaction Buffer, 14 μl of Nuclease-Free Water and 2 μl of RNase ONE™ Ribonuclease (5-10 u/μl) was mixed with 20 μl of each total RNA sample. The digestions were incubated at 37° C. for 1 hour and then held at 4° C., until analyzed. The digests were analyzed by electrophoresis on a native, 1% agarose, 1×TBE gel, stained with ethidium bromide. Ten μl of each reaction was loaded per lane. The image was collected using an Alpha Innotech FluorChem™ Imaging System. Lanes 1-12 show the Elution 1 results and Lanes 13-24 show the Elution 2 results. Lanes 1, 13: 0.25 g Z3-1; Lanes 2, 14: 0.25 g Z3-2; Lanes 3, 15: 0.5 g Z3-1; Lanes 4, 16: 0.5 g Z3-2; Lanes 5, 17: 0.75 g Z3-1; Lanes 6, 18: 0.75 g Z3-2; Lanes 7, 19: 1.0 g Z3-1; Lanes 8, 20: 1.0 g Z3-2: Lanes 9, 21: 1.5 g Z3-1; Lanes 10, 22: 1.5 g Z3-2; Lanes 11, 23: 0.5 g Z3-1 S; Lanes 12, 24: 0.5 g Z3-2 S. Lane M: Promega's PCR Markers (Cat. #G3161), 1,000 bp, 750 bp, 500 bp, 300 bp, 150 bp and 50 bp. Representative size markers are indicated. Partially degraded total RNA from the RNase ONE™ Ribonuclease digestion is indicated in lanes 1-12 by an arrow.

Example 5

Isolation of Total RNA from Plant Cells

This example describes the isolation of total RNA from plant cells. 0.73 g and 0.59 g canola leaves were flash frozen in liquid nitrogen and ground to a fine powder with mortar and pestle, and then stored in 15 ml tubes at −80° C. Two 15 ml tubes containing frozen ground canola leaves were removed from the −80° C. freezer. 4 ml SV RNA Lysis Buffer (a guanidine thiocyanate (GTC) and β-mercaptoethanol (BME)-based solution; Promega cat #Z3051) including 80 ul of 48.7% beta mercaptoethanol was added to one tube containing ground canola leaves and the contents were transferred into the second tube. An additional 4 ml of SV RNA Lysis Buffer with BME was added to tube 1 and after mixing was transferred to the second tube. Tube 1 was then discarded. The tube containing ~1.3 g tissue and 8 ml SV RNA Lysis buffer with BME was incubated at 22° C. for 20 minutes to lyse the tissue.

2 ml aliquots of the lysed canola tissue were dispensed into four 15 ml tubes labeled P1, P2, P3 and P4. 4 ml DB4/zeolite mix was added to each of the four tubes and they were inverted 3-4 times to mix the samples. DB4/zeolite mix was made by adding zeolite particles (Molecular Sieves type 13x, Sigma cat #M3010) to a Dilution Buffer at a concentration of 125 mg/ml, where the dilution buffer was composed of 3M NaCl, 0.3M $Na_3$ $citrate.2H_2O$, 0.2% SDS, and 0.0009% Blue dye (FD&C Blue #1), with the final pH adjusted to pH 4.0 with concentrated hydrochloric acid. Tubes P1-P4 were incubated in a water bath at 70° C. for 3 minutes. The tubes were returned to a rack at room temperature. An additional 500 mg zeolite powder was added to each of tubes P1 and P2 which were then inverted and shaken to mix.

For each sample a Promega PureYield™ Clearing Column was inserted in 50 ml polypropylene catch tube (caps discarded) labeled P1-P4. One at a time, the 15 ml tubes P1-P4 were inverted and shaken to mix and then immediately poured into the PureYield™ Clearing Column in the corresponding labeled tube. These clearing columns in catch tubes were centrifuged at 2000×g for 10 minutes at 24° C. All the liquid passed through the columns. The Clearing Columns were discarded. 4 ml isopropyl alcohol was added to the flow through in each tube and inverted 2-4 times to mix. This mixture was poured into a Promega PureYield™ Binding Column in a 50 ml tube and spun in a centrifuge at 2000×g at 24° C.

The binding columns were connected to a vacuum manifold (Promega cat #A7231). The columns were washed with 10 ml and then 20 ml SV RNA Wash Solution (Promega cat #Z3091) applying a vacuum. After all wash solution had flowed through, the vacuum was applied for an additional 3 minutes to dry the column membrane. The binding columns were transferred to clean 50 ml tubes.

To elute the RNA, 1 ml of nuclease-free water was applied to the binding membrane and incubated at 22° C. for 1 minute. The columns were spun in a centrifuge at 2000×g for 2 minutes (elution 1). The column was transferred to a fresh 50 ml tube and the elution with 1 ml nuclease-free water was repeated (elution 2).

To evaluate the eluates the samples were loaded on gels and on the Agilent 2100 Bioanalyzer. For the gel, 10 ul of each first elution (E1) was incubated at 37° C. for approximately one hour with 1.0 ul RNase ONE™ ribonuclease enzyme (Promega part #M426C) and 1.2 ul 10× RNase ONE™ buffer (Promega part #M217A) to digest the RNA. Approximately 3 ul of Blue/Orange 6× loading dye (Promega cat. #G1881) was added to the RNase ONE™-treated samples. 2 ul of Blue/Orange 6× loading dye was added to 10 ul of untreated E1. Each lambda marker lane has 2 ul of lambda DNA EcoRI/HindIII marker (Promega Cat. #G173A) mixed with 8 ul water and 2 ul Blue/Orange Loading Dye, 6×. Each 100 bp ladder lane has 3 ul 100 bp DNA ladder (Promega cat. #G210A) mixed with 7 ul water and 2 ul Blue/Orange Loading Dye, 6×. All samples with loading dye were loaded on a 1×TBE 1% agarose gel containing ethidium bromide. The gel shows the presence of RNA for all four replicates and the ribonuclease-treated samples indicate that there is no visible DNA contamination.

The samples were also analyzed using the RNA 6000 Nano LabChip kit (Agilent Technologies, Palo Alto, Calif., USA, part #5065-4476) with the RNA 6000 Ladder (Ambion, Austin, Tex., USA, Cat #7152) on the Agilent 2100 Bioanalyzer. 1.0 ul of sample was loaded as recommended in the Reagent Kit Guide RNA 6000 Nano Assay (Agilent Technologies, Edition November 2003). The Bioanalyzer electropherograms show sharp peaks that indicate the RNA is intact and not degraded. They also show a return to baseline between the two largest rRNA peaks (running at 39 and 44 seconds), which is important as the inter-region between the two largest peaks is typically where DNA contamination is seen if it is present.

Example 6

Removal of DNA Contamination from RNA Samples Isolated using TRIzol®

This example describes the removal of DNA contamination from RNA samples originally isolated using TRIzol® reagent (Invitrogen Life Technologies, Carlsbad, Calif., cat #15596-026). Frozen bovine liver tissue was homogenized in TRIzol reagent in two tubes (A and B) with a rotor stator homogenizer. Tube A had 1.21 g bovine liver and 12.1 ml TRIzol reagent while tube B had 1.15 g bovine liver and 11.5 ml TRIzol reagent. The homogenates in tubes A and B were combined, and inverted and shaken to mix. 3 ml of homogenate were dispensed into each of 6 Corex tubes. The 6 tubes of homogenate were incubated at 22° C. for 5 minutes. 0.6 ml chloroform was added to each of the four tubes and then shaken vigorously by hand to mix for 15 seconds. The tubes were incubated at 22° C. for 2-3 minutes then centrifuged at 10,700×g for 15 minutes at 2-8° C. The colorless upper aqueous phase containing the RNA was transferred to fresh 15 ml screw-cap polypropylene tubes.

The RNA was precipitated out of the aqueous solution by addition of 1.5 ml isopropyl alcohol per tube and mixed. Immediately after isopropyl alcohol was added, tubes 3 and 4 were each poured into Promega PureYield™ Binding Columns in 50 ml tubes and the samples were prepared following the Aqueous Control Protocol, see below. The remaining four tubes were incubated at 22° C. for 40 minutes and then centrifuged at 2600×g for 15 minutes at 2-8° C. The supernatant was removed. Tubes 5 and 6 were prepared following the Pellet Hybrid Protocol, see below. Tubes 1 and 2 followed the TRIzol protocol (Invitrogen Form No. 18057N) with the pellets each being washed with 3 ml of 75% ethanol. Tubes 1 and 2 were stored overnight at 4° C. in 75% ethanol.

Tubes 1 and 2 were mixed by vortex and then centrifuged at 2600×g for 5 minutes at 2-8° C. The supernatants were removed and the RNA pellets air dried for 10 minutes at 22° C. Each of the RNA pellets was dissolved in 1 ml nuclease-free water by pipetting up and down several times and incubating at 55-60° C. for 10 minutes. 50 ul of RNA solution was removed (called TRIzol RNA 1 and TRIzol RNA 2) for analysis before proceeding. 1 ml of SV RNA Lysis Buffer (a guanidine thiocyanate (GTC) and β-mercaptoethanol (BME)-based solution; Promega cat. #Z3051) with 20 ul of 48.7% beta-mercaptoethanol was added to the remaining RNA (~950 ul) purified with TRIzol reagent. This ~2 ml RNA/lysis buffer mixture was used in place of the 2 ml lysate in the Promega PureYield™ RNA Midi protocol, see below.

PureYield™ RNA Midi Protocol 4 ml DB4.36 (DB4.36 is 3M NaCl, 0.36M Na$_3$ citrate.2H$_2$O, 0.01 mM EDTA (pH 8.0) and 0.0009% Blue dye (FD&C Blue #1) adjusted to a final pH of 4.0 with concentrated hydrochloric acid) and 1 ml ZM1 (ZM1 is 2M NaCl, 0.1 mM EDTA (pH 8.0) with zeolite added at a concentration of 0.45 g/ml) were added to each of tubes 1 and 2, which were then inverted 3-4 times while shaking to mix. The tubes were incubated in a water bath at 70° C. for 3 minutes and then returned to a rack at 22° C. For each sample a Promega PureYield™ Clearing Column was inserted in a 50 ml polypropylene catch tube (caps discarded). One at a time, the 15 ml tubes were inverted and shaken to mix and then immediately poured into the PureYield™ Clearing Column in the corresponding labeled tube. These clearing columns in catch tubes were centrifuged at 2000×g for 10 minutes at 24° C. The Clearing Columns were discarded. 4 ml isopropyl alcohol was added to the flow through in each tube and inverted 2-4 times to mix. This mixture was poured into a Promega PureYield™ Binding Column in a 50 ml tube and centrifuged at 2000×g at 24° C. The Binding Column flow through was discarded.

15 ml SV RNA Wash Solution (Promega cat #Z3091) was applied to the Binding Column and removed by centrifugation at 2,000×g for 5 minutes at 24° C. The flow through was discarded. Another 15 ml SV RNA Wash Solution was applied to the binding column and removed by centrifugation at 2,000×g for 10 minutes at 24° C. The Binding Columns were transferred into fresh 50 ml tubes.

To elute the RNA, 1 ml of nuclease-free water was applied to the binding membrane and incubated at 22° C. for 1 minute. The columns were centrifuged at 2000×g for 2 minutes at 24° C. These samples are called TRIzol/PureYield™ 1 E1 and TRIzol/PureYield™ 2 E 1. The elution of RNA was repeated with an additional 1 ml of nuclease-free water applied to the binding membrane and the samples were called TRIzol/PureYield™ 1 E2 and TRIzol/PureYield™ 2 E2.

Aqueous Control Protocol (No Guanidine and No Zeolite)

This Aqueous Control protocol starts with the contents of tubes 3 and 4 having been poured onto binding columns above, each containing an aqueous solution with RNA precipitating. The samples were centrifuged at 2000×g for 10 minutes at 24° C. The binding column flow through was discarded.

20 ml SV RNA Wash Solution (Promega cat #Z3091) was applied to the Binding Column and removed by centrifugation at 2,000×g for 10 minutes at 24° C. The flow through was discarded. Another 20 ml SV RNA Wash Solution was applied to the binding column and removed by centrifugation at 2,000×g for 10 minutes at 24° C. The Binding Columns were transferred into fresh 50 ml tubes. The binding columns were stored at −20° C. The binding columns were warmed at 4° C. and then at 22° C. The binding columns were centrifuged at 2000×g for 5 minutes at 24° C. Then the binding columns were transferred to a fresh 50 ml tube.

To elute the RNA, 1 ml of nuclease-free water was applied to the binding membrane and incubated at 22° C. for 1 minute. The columns were centrifuged at 2000×g for 2 minutes at 24° C. These samples are called 3 Aqueous Control E1 and 4 Aqueous Control E1. The elution of RNA was repeated with an additional 1 ml of nuclease-free water applied to the binding membrane and the samples were called 3 Aqueous Control E2 and 4 Aqueous Control E2.

Pellet Hybrid Protocol

This variation on the protocol starts with tubes 5 and 6 from above, each containing a TRIzol RNA pellet with the supernatant removed. The pellets were dissolved by adding 2 ml SV RNA Lysis Buffer, containing 40 ul 48.7% BME and stored overnight at 4° C.

Tubes 5 and 6 were returned to 22° C. and the buffer was pipetted up and down to dissolve the RNA pellet. 4 ml DB4.36 and 1 ml ZM1 were added to each tube, which were then inverted 3-4 times while shaking to mix. The tubes were incubated in a water bath at 70° C. for 3 minutes and then returned to a rack at 22° C. For each sample a Promega PureYield™ Clearing Column was inserted in a 50 ml polypropylene catch tube (caps discarded). One at a time, the 15 ml tubes were inverted and shaken to mix and then immediately poured into the PureYield™ Clearing Column in the corresponding labeled tube. These clearing columns in catch tubes were centrifuged at 2000×g for 10 minutes at 24° C. The Clearing Columns were discarded. 4 ml isopropyl alcohol was added to the flow through in each tube and inverted 2-4 times to mix. This mixture was poured into a PureYield™ Binding Column in a 50 ml tube and centrifuged at 2000×g at 24° C. The Binding Column flow through was discarded.

15 ml SV RNA Wash Solution (Promega cat #Z3091) was applied to the Binding Column and removed by centrifugation at 2,000×g for 5 minutes at 24° C. The flow through was discarded. Another 15 ml SV RNA Wash Solution was applied to the binding column and removed by centrifugation at 2,000×g for 10 minutes at 24° C. The Binding Columns were transferred into fresh 50 ml tubes.

To elute the RNA, 1 ml of nuclease-free water was applied to the binding membrane and incubated at 24° C. for 1 minute. The columns were centrifuged at 2000×g for 2 minutes. These samples were called 5 Pellet Hybrid E1 and 6 Pellet Hybrid E1. The elution of RNA was repeated with an additional 1 ml of nuclease-free water applied to the binding membrane and the samples were called 5 Pellet Hybrid E2 and 6 Pellet Hybrid E2.

Analysis

After dilution in nuclease-free water, the nucleic acid yields were determined by absorbance at 260 nm (A260).

TABLE 5

Total RNA Yield from Bovine Liver Cells

| Sample | Dilution | A230 | A260 | A280 | A260/280 | Vol (ul) | A260 total (ug) | Avr. of 2 |
|---|---|---|---|---|---|---|---|---|
| TRIzol RNA 1 | 20 | 0.52638 | 1.11480 | 0.65915 | 1.69 | 900 | 802.7 | |
| TRIzol RNA 2 | 40 | 0.26912 | 0.60010 | 0.37276 | 1.61 | 900 | 864.1 | 833.4 |

TABLE 5-continued

Total RNA Yield from Bovine Liver Cells

| Sample | Dilution | A230 | A260 | A280 | A260/280 | Vol (ul) | A260 total (ug) | Avr. of 2 |
|---|---|---|---|---|---|---|---|---|
| TRIzol/PureYield ™ 1 E1 | 20 | 0.28187 | 0.59267 | 0.29414 | 2.01 | 900 | 426.7 | |
| TRIzol/PureYield ™ 2 E1 | 20 | 0.31320 | 0.64764 | 0.31411 | 2.06 | 900 | 466.3 | 446.5 |
| 3 Aqueous Control E1 | 20 | 0.40800 | 0.87175 | 0.42798 | 2.04 | 900 | 627.7 | |
| 4 Aqueous Control E1 | 20 | 0.37554 | 0.80448 | 0.39449 | 2.04 | 900 | 579.2 | 603.4 |
| 5 Pellet Hybrid E1 | 20 | 0.28248 | 0.57867 | 0.28290 | 2.05 | 900 | 462.9 | |
| 6 Pellet Hybrid E1 | 20 | 0.25663 | 0.49269 | 0.24119 | 2.04 | 900 | 394.2 | 385.7 |
| TRIzol/PureYield ™ 1 E2 | 10 | 0.08574 | 0.13813 | 0.08249 | 1.67 | 900 | 49.7 | |
| TRIzol/PureYield ™ 2 E2 | 10 | 0.09423 | 0.17587 | 0.09780 | 1.80 | 900 | 63.3 | 56.5 |
| 3 Aqueous Control E2 | 10 | 0.29494 | 0.59332 | 0.31480 | 1.88 | 900 | 213.6 | |
| 4 Aqueous Control E2 | 10 | 0.30789 | 0.62119 | 0.32465 | 1.91 | 900 | 223.6 | 218.6 |
| 5 Pellet Hybrid E2 | 10 | 0.13116 | 0.25267 | 0.13164 | 1.92 | 900 | 91.0 | |
| 6 Pellet Hybrid E2 | 10 | 0.13131 | 0.19240 | 0.10171 | 1.89 | 900 | 69.3 | 80.1 |

RNase ONE™ Ribonuclease Treatment

For each of the samples listed above, 10 ul of sample was added to 1.2 ul of RNase ONE 10× Buffer (Promega Part #217A) in a PCR strip tube and then 1.0 ul of RNase ONE Ribonuclease enzyme (Promega part #M4261) was added. The strip tube was capped and incubated at 37° C. for about an hour.

Agarose Gel 2.5 ul of Blue/Orange Loading Dye, 6× (Promega cat. #G1881) was added to each ribonuclease-treated sample. On a piece of parafilm, 10 ul of untreated sample was added to 2 ul of Blue/Orange Loading Dye, 6×. Each lambda marker lane has 2 ul of lambda DNA EcoRI/HindIII marker (Promega cat. #G173A) mixed with 8 ul water and 2 ul Blue/Orange Loading Dye, 6×. Each 100 bp ladder lane has 3 ul 100 bp DNA ladder (Promega cat. #G6951) mixed with 7 ul water and 2 ul Blue/Orange Loading Dye, 6×.

The samples were electrophoresed on a 1% agarose 1×TBE gel with ethidium bromide added. The results are shown in FIG. 5. FIG. 5A shows the untreated samples and FIG. 5B shows the samples treated with RNase ONE™ Ribonuclease. Both FIGS. 5A and 5B have samples loaded in the same order, with the following lane designations: lane 1—Lambda DNA EcoRI/HindIII marker; lane 2—100 bp DNA ladder (FIG. 5A only); lane 3—blank; lane 4—TRIzol RNA 1 E1; lane 5—TRIzol RNA 2 E1; lane 6—TRIzol/PureYield™ 1 E1; lane 7—TRIzol/PureYield™ 2 E1; lane 8—3 Aqueous Control E1; lane 9—4 Aqueous Control E1; lane 10—5 Pellet Hybrid E1; lane 11—6 Pellet Hybrid E1; lane 12—blank; lane 13—Lambda DNA EcoRI/HindIII marker; lane 14—100 bp DNA Ladder; lane 15—blank; lane 16—TRIzol/PureYield™ E2; lane 17—TRIzol/PureYield™ 2 E2; lane 18—3 Aqueous Control E2; lane 19—4 Aqueous Control E2; lane 20—5 Pellet Hybrid E2; lane 21—6 Pellet Hybrid E2; lane 22—blank; lane 23—Lambda DNA EcoRI/HindIII marker; lane 24—100 bp DNA Ladder (FIG. 5A only).

The results presented in FIG. 5, particularly FIG. 5B, show that the protocols using only TRIzol reagent had detectable DNA contamination while the protocols which added DB4 and zeolite to the TRIzol reagent protocols resulted in no detectable DNA contamination. In FIG. 5B, lanes 4, and 5 (from the first elution) and lanes 18 and 19 (from the second elution) show the result of the DNA contamination assay where only TRIzol reagent is used to purify the RNA, while lanes 8 and 9 show the results of the DNA contamination assay where TRIzol reagent was used followed by washes on a PureYield™ binding column. As seen in this figure, all of these lanes display visible DNA contamination. Lanes 6, 7, 10, and 11 (from the first elution) and lanes 16, 17, 20 and 21 (from the second elution) show the result of the DNA contamination assay where DB4 (dilution buffer at pH 4) and zeolite particles are used to remove DNA. As seen in this figure, not detectable DNA contamination is present in these lanes. Together, these results indicate that a protocol employing DB4 and zeolite particles is able to purify RNA away from DNA at a level that is superior to the level achieved with a protocol employing only TRIzol reagent.

Example 7

Isolation of Total RNA from Human Blood

This example describes the isolation of total RNA from human blood. Blood drawn from two individuals was designated "(H)" for "High" and "(L)" for "Low" to indicate the relative white blood cell (leukocyte) count. The blood was collected by venipuncture in sterile 6 ml $K_2$EDTA BD Vacutainer® Plus Plastic Blood Collection Tubes (Becton Dickinson, Franklin Lakes, N.J.). The blood was stored at 4° C. for 4 days and then transferred to ice for processing. Four tubes of blood (estimated to contain approximately 5 ml each) from each individual were pooled and dispensed into 1.5 ml aliquots in 2 ml microcentrifuge tubes with sealed caps. The (H) samples were centrifuged at 12,000×g for 15 minutes at 4° C. and the (L) samples were centrifuged at 9,000×g for approximately 10 minutes at 4° C. to fractionate the blood. The upper, yellow, clear serum layer was carefully removed with a pipet. The white buffy coat, containing leukocytes, was carefully withdrawn from the interface with a pipet. The buffy coat was pooled for each individual. The pooled buffy coat samples were contaminated with some red blood cells from the lower red blood cell fraction. Two ml of Lysis Buffer (4M guanidine thiocyanate, 10 mM Tris, pH 7.5, with beta-mercaptoethanol added separately to a final concentration of 0.974% (v/v)) was added to each of the samples, (H) and (L). The mixtures were vortexed vigorously to lyse the leukocytes. The dark red lysates were stored at −70° C., until use.

The frozen lysates were thawed at 4° C. Four ml of Dilution Buffer (3M NaCl, 0.3M $Na_3$ citrate.$2H_2O$, 0.2% SDS, 0.0009% Blue dye (FD&C Blue #1), adjusted to a final pH of 4.0 with concentrated hydrochloric acid (HCl)) was added to each sample and mixed by inversion. The mixtures congealed, forming insoluble, stringy clumps. The tubes were incubated at 70° C. in a hybridization oven for 3 minutes and then placed at ambient temperature (23° C.). Molecular Sieves, Type 13X, powder (<10 μm) (zeolite) was weighed and 0.5 g was added to each tube. Each mixture was shaken vigorously and immediately poured into a Promega PureYield™ clearing column, nested in a 50 ml collection tube. The columns were centrifuged in a swinging bucket rotor at approximately 2,000×g, 23° C. for 10 minutes. The cleared lysates, containing RNA, were captured in 50 ml collection tubes.

The following steps were performed at ambient temperature (23° C.). Four ml of isopropanol was added to each of the cleared lysates and mixed by inversion. Each mixture was applied to a Promega PureYield™ binding column, attached to a vacuum manifold. A vacuum of approximately 15 in. Hg was applied to the columns. Each sample passed through the column, leaving the RNA bound to the binding column membrane. The membranes were washed twice with 10 ml and then 20 ml of Wash Solution (60 mM potassium acetate, 10 mM Tris, pH 7.5, 60% ethanol) to remove impurities and salts. The membranes were vacuum dried for 3 minutes on the vacuum manifold. The binding columns were transferred to 50 ml collection tubes for elution.

0.5 ml of nuclease-free water was applied to each membrane and incubated for 1 minute at 23° C. The column assemblies were centrifuged, using a swinging bucket rotor, at 2,000×g for 2 minutes to collect the purified total RNA. The elution steps were repeated, with an additional 0.5 ml of nuclease-free water. The second eluates were collected in fresh 50 ml tubes. Approximately 200 μl and 500 μl of eluate was recovered from the first and second elutions, respectively. The reduced eluate volume was caused by absorption of water by the dried binding membrane. The purified total RNA samples were analyzed by spectrophotometry and agarose gel analysis. Total RNA yields were determined by absorbance at 260 nm. The results are shown in Table 6 and FIGS. 6A and 6B.

TABLE 6

Total RNA Yield from Human Blood

| Sample ID | Total RNA Yield Elution 1 (μg) | Total RNA Yield Elution 2 (μg) | Total RNA Yield Elution 1 + 2 (μg) |
|---|---|---|---|
| Hu (H) | 12.1 | 29.2 | 41.3 |
| Hu (L) | 9.1 | 8.2 | 17.3 |

FIG. 6A shows a gel analysis of purified total RNA from human blood. RNA samples were analyzed by electrophoresis on a native, 1% agarose, 1×TBE gel, stained with ethidium bromide. Ten μl of each sample was loaded per lane. The image was collected using an Alpha Innotech FluorChem™ Imaging System. The image brightness was increased to visualize the faint rRNA bands. Lanes 1-2 show the Elution 1 results and Lanes 3-4 show the Elution 2 results. The Elution 1 samples were more concentrated than the Elution 2 samples. Lanes 1, 3: Hu (H); Lanes 2, 4: Hu (L). The undenatured 28S ribosomal RNA, 18S ribosomal RNA and small RNAs are indicated by arrows.

FIG. 6B shows the results of a DNA contamination assay of total RNA purified from human blood. Purified total RNA samples were digested with Promega's RNase ONE™ Ribonuclease (Cat. #M4265). A 15 μl digestion mix, consisting of 3 μl of 10× Reaction Buffer, 9 μl of Nuclease-Free Water and 3 μl of RNase ONE™ Ribonuclease (5-10 u/μl) was mixed with 15 μl of each total RNA sample. The digestions were incubated at 37° C. for 1 hour and then held at 4° C., until analyzed. The digests were analyzed by electrophoresis on a native, 1% agarose, 1×TBE gel, stained with ethidium bromide. Ten μl of each reaction was loaded per lane. The image was collected using an Alpha Innotech FluorChem™ Imaging System. Lanes 1-2 show the Elution 1 results and Lanes 3-4 show the Elution 2 results. Lanes 1, 3: Hu (H); Lanes 2, 4: Hu (L). Lane G: Control samples containing genomic DNA.

Example 8

DNA Zeolite Binding

This example describes assays employed to determine the amount of DNA and RNA binding to zeolite particles in the presence of an acidic buffer. As described below, zeolite particles preferentially bind to DNA molecules and have only limited binding to RNA molecules.

7.2 g frozen bovine spleen tissue was homogenized in 48 ml SV RNA Lysis Buffer (Promega cat # Z3051) including 960 ul of 48.7% beta mercaptoethanol (BME, Promega part #Z523A) using a rotor stator homogenizer. The homogenate was divided into tubes and stored at minus 80° C. All the tubes used in this example were polypropylene screw-cap centrifuge tubes.

A tube containing homogenized bovine spleen was removed from the −80° C. freezer and thawed in water at 4° C. 2 ml aliquots of the bovine spleen homogenate were dispensed into four 15 ml tubes and the remainder of the homogenate was stored at −20° C. Four (4) ml DB4.36 was added to each of the tubes and then 1 ml ZM1 was added to each tube. DB4.36 is 3M NaCl, 0.36M $Na_3$ citrate.$2H_2O$, 0.1 mM EDTA (pH 8.0), and 0.0009% Blue dye (FD&C Blue #1) adjusted to a final pH of 4.0 with concentrated hydrochloric acid, while ZM1 is 2M NaCl, 0.1 mM EDTA (pH 8.0) with zeolite added at a concentration of 0.45 g/ml. The tubes were inverted 3-4 times and shaken to mix the samples. The 4 tubes were incubated in a water bath at 70° C. for 3 minutes and then returned to a rack at room temperature.

For each sample a PureYield Clearing Column (Promega) was inserted in a 50 ml polypropylene catch tube (cap discarded) labeled C1-C4. One at a time, the 15 ml tubes 1-4 were inverted and shaken to mix and then immediately poured into the PureYield Clearing Column in the corresponding labeled tube. These clearing columns in catch tubes were centrifuged at 2000×g for 10 minutes at 22° C. The Clearing Columns were saved to later separate the zeolite from the clearing column membrane, see below. 4 ml isopropyl alcohol was added to the flow through in each tube and inverted 2-4 times to mix. This mixture was poured into a PureYield Binding Column (Promega), labeled B1-B4, in a 50 ml tube and spun in a centrifuge at 2000×g at 22° C.

The binding columns were transferred to a fresh 50 ml column and the flow through (FT 1-4) was stored at −20° C. 20 ml SV RNA Wash Solution (Promega cat #Z3091) was added to the binding column and centrifuged at 2,000×g for 5 minutes. The flow through was stored at −20° C. Then 10 ml SV RNA Wash Solution was added to the binding column and centrifuged at 2,000×g for 10 minutes. The binding columns were transferred to clean 50 ml tubes.

To elute the RNA, 1 ml of nuclease-free water was applied to the binding membrane and incubated at 22° C. for 1 minute. The columns were centrifuged at 2000×g for 2 minutes (RNA elution 1). The column was transferred to a fresh 50 ml tube and the elution with 1 ml nuclease-free water was repeated (RNA elution 2).

The used zeolite in clearing columns C1-C4 was removed from the column membrane by separating the zeolite from the membrane and then scraping off any remaining membrane. The zeolite was transferred to a fresh PureYield Clearing Column labeled C1'-C4' in a 50 ml tube. 1.0 ml nuclease-free water was added to each clearing column C1'-C4' and incubated at 22° C. for 3 minutes. The tubes were then centrifuged at 2,000×g for 10 minutes at 22° C. (zeolite elution 1). The clearing columns were transferred to fresh 50 ml tubes and the elution with 1 ml nuclease-free water was repeated (zeolite elution 2).

The first sample analysis was performed as follows to generate FIG. 7a. The samples were loaded on 1% Seakem Gold, 1×TBE gels containing ethidium bromide (Cambrex Bio Science Rockland, Inc., Rockland, Me. Cat#54907). 15 ul of zeolite (1-4) elution 1 was added to 3 ul Blue/Orange Loading Dye, 6× (Promega). 15 ul of flow through sample (FT1-4) was added to 3 ul Blue/Orange Loading Dye, 6×. 15 ul of homogenate was added to 3 ul Blue/Orange Loading Dye, 6×. Each lambda marker lane has 1 ul of lambda DNA EcoRI/HindIII marker (Promega) mixed with 9 ul water and 2 ul Blue/Orange Loading Dye, 6×. The zeolite elutions in lanes 2-5 show that certain nucleic acids are bound and released from the zeolite. In FIG. 7a, the sample loading order is as follows: 1. Lambda DNA EcoRI/HindIII marker; 2. Zeolite 1 elution 1; 3. Zeolite 2 elution 1; 4. Zeolite 3 elution 1; 5. Zeolite 4 elution 1; 6. Lambda DNA EcoRI/HindIII marker; 7. Blank; 8. Flow through 1; 9. Blank; 10. Flow through 2; 11. Blank; 12. Flow through 3; 13. Blank; 14. Flow through 4; 15. Blank; 16. Lambda DNA EcoRI/HindIII marker; 17. Blank; 18. Homogenate; 19. Blank; and 20. Blank. The gel in FIG. 7a shows the enormous amount of DNA and RNA in the homogenate in lane 18, and that very little nucleic acid remains in the PureYield Binding Column flow through in lanes 8, 10, 12 and 14.

The second sample analysis was performed as follows to generate FIG. 7b. 100 ul of each zeolite (1-4) elution 1 sample was incubated at 37° C. for two hours with 3.0 ul RNase ONE™ ribonuclease enzyme (Promega part #M426C) and 11 ul 10× RNase ONE™ buffer (Promega part #M217A) to digest the RNA. 100 ul of each zeolite (1-4) elution 1 sample was incubated at 37° C. for two hour with 3.0 ul RQ1 RNase-free DNase (Promega) and 11 ul 10× Reaction Buffer (Promega) to digest the DNA. After the incubation the samples were pipetted onto parafilm and concentrated by evaporation for one hour. 25 ul of concentrated sample was mixed with 5 ul Blue/Orange Loading Dye, 6× (Promega) and 20 ul was loaded on the gel. Each lambda marker lane has 2 ul of lambda DNA EcoRI/HindIII marker (Promega) mixed with 8 ul water and 2 ul Blue/Orange Loading Dye, 6×. Each 100 bp ladder lane has 3 ul 100 bp DNA ladder (Promega) mixed with 7 ul water and 2 ul Blue/Orange Loading Dye, 6×. All samples with loading dye were loaded on a 1× TBE, 1% agarose LE analytical grade (Promega) gel containing ethidium bromide. The RNase treatment and DNase treatment show that both RNA and DNA are bound and eluted from the zeolite. However, it is clear that zeolite only binds a small amount of RNA and is preferentially binding to DNA. Moreover, it appears that the zeolite binds the DNA strongly such that, using the conditions described above, not much of the DNA was eluted from the zeolite particles (i.e. most of the DNA remained bound to the zeolite particles).

In FIG. 7b, the sample loading order is as follows: 1. 100 bp DNA ladder; 2. Lambda DNA EcoRI/HindIII marker; 3. Blank; 4. Zeolite 1 elution 1; 5. Blank; 6. Blank 7. Zeolite 2 elution 1; 8. Blank; 9. Blank; 10. Zeolite 3 elution 1; 11. Blank; 12. Blank; 13. Zeolite 4 elution 1; 14. Blank; 15. Blank; 16. Lambda DNA EcoRI/HindIII marker; 17. Blank; 18. Zeolite 1 elution 1, treated with DNase; 19. Blank; 20. Zeolite 2 elution 1, treated with DNase; 21. Blank; 22. Zeolite 3 elution 1, treated with DNase; 23. Blank; 24. Zeolite 4 elution 1, treated with DNase; 25. Blank; 26. Lambda DNA EcoRI/HindIII marker; 27. Blank; 28. Zeolite 1 elution 1, treated with RNase; 29. Blank; 30. Zeolite 2 elution 1, treated with RNase; 31. Blank; 32. Zeolite 3 elution 1, treated with RNase; 33. Blank; 34. Zeolite 4 elution 1, treated with RNase; 35. Blank; 36. Lambda DNA EcoRI/HindIII marker; 37. 100 bp DNA ladder. The DNase-treated samples in lanes 18, 20, 22 and 24 show distinct RNA bands as well as a smear. The RNase-treated samples show a faint smear of DNA in lanes 28, 30, 32, and 34.

The third sample analysis was performed as follows to generate FIG. 7c. 10 ul of each RNA elution 1 sample (#1, 2, and 4) was incubated at 37° C. for two hours with 2.0 ul RNase ONE™ ribonuclease enzyme (Promega) and 1.3 ul 10× RNase ONE™ buffer (Promega) to digest the RNA. RNA 3 elution 1 was incubated at the same temperature and for the same time as the other samples, but had 4.0 ul RNase ONE ribonuclease enzyme with the 1.3 ul 10× RNase ONE buffer. 3 ul Blue/Orange Loading Dye, 6× was added to each RNase-treated RNA elution sample. 2 ul Blue/Orange Loading Dye, 6× was added to 10 ul of each RNA elution sample. Each lambda marker lane has 2 ul of lambda DNA EcoRI/HindIII marker (Promega) mixed with 8 ul water and 2 ul Blue/Orange Loading Dye, 6×. Each 100 bp ladder lane has 2 ul 100 bp DNA ladder (Promega) mixed with 8 ul water and 2 ul Blue/Orange Loading Dye, 6×.

In FIG. 7c, the sample loading order is as follows: 1. Lambda DNA EcoRI/HindIII marker; 2. Blank; 3. RNA 1 elution 1; 4. RNA 2 elution 1; 5. RNA 3 elution 1; 6. RNA 4 elution 1; 7. Blank; 8. Lambda DNA EcoRI/HindIII marker; 9. 100 bp DNA ladder; 10. Blank; 11. RNA 1 elution 1, treated with RNase; 12. RNA 2 elution 1, treated with RNase; 13. RNA 3 elution 1, treated with RNase; 14. RNA 4 elution 1, treated with RNase; 15. Blank; and 16. Lambda DNA EcoRI/HindIII marker. The gel in FIG. 7C shows the RNA eluted from the PureYield Binding membrane in lanes 3-6. The RNase-treated samples in lanes 11-14 show little or no DNA eluted from the PureYield Binding membrane.

Example 9

Preferential DNA or RNA Binding with Various Substrates in an Acidic Buffer

This Example describes protocols used to assay various substrates for nucleic acid binding in the presence of an acidic buffer. Besides demonstrating that various zeolite particle solutions preferentially bind DNA, these assays demonstrated that titanium oxide preferentially binds RNA.

600 mg frozen bovine spleen was homogenized per 2 ml SV RNA Lysis Buffer (Promega) including 20 ul 48.7% beta mercaptoethanol (BME, Promega) per milliliter buffer using a rotor stator homogenizer. The homogenate was divided into tubes and stored at minus 80° C.

Tubes containing homogenized bovine spleen were removed from the −80° C. freezer and thawed in water at 4° C. The homogenate was diluted with an equal amount of SV RNA Lysis Buffer with BME added. 2 ml aliquots of the diluted bovine spleen homogenate were dispensed into 15 ml tubes. 4 ml DB4 was added to each of the tubes that later had added zeolite powder, zeolite in solution or the non-zeolite binding matrices. DB4 is 3.0M NaCl, 0.30M $Na_3$ citrate.$2H_2O$, and 0.0009% Blue dye (FD&C Blue #1) adjusted to a final pH of 4.0 with concentrated hydrochloric acid. 4 ml reduced salt DB4 was added to a second set of tubes with zeolite powder or zeolite in solution. Reduced salt DB4 is 2.2M NaCl, 0.30M $Na_3$ citrate.$2H_2O$, adjusted to a final pH of 4.0 with concentrated hydrochloric acid. After dilution buffer was added the tubes were mixed by inversion. The tubes were incubated in a water bath at 70° C. for 3 minutes and then returned to a rack at room temperature. Then to each of the tubes, one of the following binding matrices was added: 0.5 g zeolite powder (Molecular Sieves, type 13x), 0.5 g zeolite in 1-2 ml salt water (2-5M NaCl), 0.5 g zeolite in 1.0 ml water, 0.5 g zeolite in 1.0 ml isopropanol, 0.5 g alumina in 1.0 ml water, 0.5 g Sea Sand, 0.5 g titanium (IV) oxide anatase powder in 1.0 ml water, 0.25 g zinc oxide in 1.0 ml water, 0.5 g zirconium oxide in 1.0 ml water. The tubes were inverted and shaken to mix the samples.

For each sample a PureYield Clearing Column (Promega) was inserted in 50 ml polypropylene catch tube (cap discarded). One at a time, the 15 ml tubes were inverted and shaken to mix and then immediately poured into a PureYield Clearing Column. These clearing columns in catch tubes were centrifuged at 2000×g for 10 minutes at 24° C. The clearing columns were discarded. 4 ml isopropyl alcohol was added to the flow through in each tube and inverted 2-4 times to mix. This mixture was poured into a PureYield Binding Column (Promega) in a 50 ml tube and spun in a centrifuge at 2000×g at 24° C.

The binding columns were transferred to a clean 50 ml tube. 20 ml SV RNA Wash Solution (Promega, prepared following instructions) was applied to the column and centrifuged at 2,000×g for 6 minutes. A second wash of 10 ml SV RNA Wash Solution was added with an additional centrifugation at 2,000×g for 6 minutes. The binding columns were transferred to clean 50 ml tubes.

To elute the RNA, 1 ml of nuclease-free water was applied to the binding membrane and incubated at 22° C. for 1 minute. The columns were spun in a centrifuge at 2000×g for 2 minutes (elution 1). The column was transferred to a fresh 50 ml tube and the elution with 1 ml nuclease-free water was repeated (elution 2).

Figure 8:
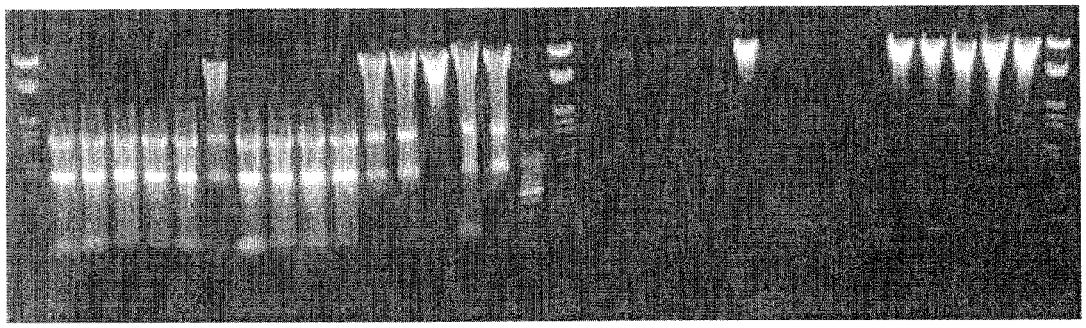
FIG. 8 shows the results of an RNase digestion assay performed as described in Example 9.

FIG. 8 was generated as follows. 10 ul of each sample was incubated at 37° C. for two hours with 1.0 ul RNase ONE™ ribonuclease enzyme (Promega part #M426C) and 1.2 ul 10× RNase ONE™ buffer (Promega part #M217A) to digest the RNA. After the incubation the RNase treated samples were each mixed with 2.5 ul Blue/Orange Loading Dye, 6× (Promega part #G190A) and 10 ul of untreated sample mixed with 2.0 ul Blue/Orange Loading Dye, 6×. Each lambda marker lane has 2 ul of lambda DNA EcoRI/HindIII marker (Promega part #G173A) mixed with 8 ul water and 2 ul Blue/Orange Loading Dye, 6×. Each 100 bp ladder lane has 3 ul 100 bp DNA ladder (Promega part #G210A) mixed with 7 ul water and 2 ul Blue/Orange Loading Dye, 6×. All samples with loading dye were loaded on a 1×TBE, 1% agarose LE analytical grade (Promega) gel containing ethidium bromide.

In FIG. 8, the sample loading order is as follows: 1. Lambda DNA EcoRI/HindIII marker; 2. Zeolite powder A; 3. Zeolite powder B; 4. zeolite in 2M NaCl; 5. zeolite in water A; 6. zeolite in water B; 7. Zeolite in isopropanol; 8. zeolite powder with lower salt DB4; 9. zeolite in water with lower salt DB4; 10. zeolite in 5M NaCl with lower salt DB4; 11. zeolite in 2.5M NaCl with lower salt DB4; 12. alumina; 13. sea sand; 14. titanium oxide; 15. zinc oxide; 16. zirconium oxide; 17. 100 bp DNA ladder; 18. Lambda DNA EcoRI/HindIII marker; 19. Zeolite powder A, treated with RNase; 20. Zeolite powder B, treated with RNase; 21. zeolite in 2M NaCl, treated with RNase; 22. zeolite in water A, treated with RNase; 23. zeolite in water B, treated with RNase; 24. Zeolite in isopropanol, treated with RNase; 25. zeolite powder with lower salt DB4, treated with RNase; 26. zeolite in water with lower salt DB4, treated with RNase; 27. zeolite in 5M NaCl with lower salt DB4, treated with RNase; 28. zeolite in 2.5M NaCl with lower salt DB4, treated with RNase; 29. alumina, treated with RNase; 30. sea sand, treated with RNase; 31. titanium oxide, treated with RNase; 32. zinc oxide, treated with RNase; 33. zirconium oxide, treated with RNase; and 34. Lambda DNA EcoRI/HindIII marker.

The gel in FIG. 8 shows that titanium oxide binds RNA preferentially as shown by the DNA and not RNA present in the binding column elution (untreated sample in lane 14, RNase treated sample in lane 31.) In contrast to the titanium oxide, the gel shows that zeolite in powder form or dissolved in water solutions binds most or all of the DNA present in the lysate and leaves the RNA for elution from the binding column. The binding matrices alumina, sea sand, zinc oxide and zirconium oxide show binding of some RNA as indicated by the loss or reduction in intensity of the smallest RNA band and reduction in band intensity for the larger 18S and 28S rRNA bands.

Example 10

Zeolite Membranes, Silica-Zeolite Membranes and Zeolite-Silica Particle Composites This example describes generating zeolite membranes, silica-zeolite coated membranes and zeolite-silica particle composites.

Zeolite membranes were generated as follows. 0.5 gm of zeolite (Aldrich, cat #233641, Molecular Sieves 3A, with a formula of $K_n Na_{12-n}[(AlO_2)_{12}(SiO_2)_{12}] \cdot xH_2O$) was added to each of 2 Promega clearing columns (cat #A2492) containing cellulose membranes, labeled as 1A and 1B. 0.5 gm of zeolite (Aldrich cat #233641) was added to each of 2 Promega binding columns containing silica membranes, labeled as 2A and 2B. 0.5 gm of zeolite (Sigma-Aldrich cat #283592, Molecular sieves, 13X, with a formula of: $Na_{86}[(AlO_2)_{86}(SiO_2)_{106}] \cdot xH_2O$) was added to each of 2 Promega binding columns containing silica membranes, labeled as 3A and 3B. All 6 columns were inserted into 50 ml plastic tubes.

To each of the above columns, 1 ml of 93% (wt/vol) KOH was added, and the contents mixed using a plastic pipette tip to thoroughly wet the zeolite particles. Columns were centrifuged at 2000×g for 5 minutes in a swinging bucket rotor. 2 ml of 1N HCl was then added and the tubes/columns were centrifuged at 2000×g for 5 minutes. A second 2 ml of 1N HCl was then added (except for tube 6 in which 2 ml of nuclease-free water was added) and the tubes/columns were centrifuged at 2000×g for 5 minutes. 5 ml of nuclease free water (Promega) was then added and the tubes/columns were centrifuged at 2000×g for 5 minutes. A second 5 ml of nuclease free water (Promega) was then added and the tubes/columns were centrifuged at 2000×g for 5 minutes. All columns were transferred to clean 50 ml tubes for use in the following Example showing their utility in removing DNA from RNA preparations.

Silica-zeolite composites were generated using Scotchlite™ S60 Glass bubbles (3M, St. Paul, Minn.). 0.6 gm of Scotchlite S60 glass bubbles were added to a 50 ml plastic tube containing 1.3 gm of zeolite (Sigma-Aldrich cat #283592, Molecular sieves, 13X) and thoroughly mixed. 4 ml of 93% KOH was added per tube and thoroughly mixed, then poured into a Promega clearing column inserted into a 50 ml tube. The tube was centrifuged at 2000×g for 10 minutes in a swinging bucket rotor. Then 4 ml of 1N HCl was added to the column, and the tube was centrifuged at 2000×g for 10 minutes. Then a second 4 ml of 1N HCl was added to the column, and the tube was centrifuged at 2000×g for 10 minutes. Then 5 ml of nuclease free water was added to the column, and the tube was centrifuged at 2000×g for 10 minutes. Then a second 5 ml of nuclease free water was added to the column, and the tube was centrifuged at 2000×g for 10 minutes. The flow-through fluid in the tube was discarded. Then a third 5 ml of nuclease free water was added to the column, and the tube was centrifuged at 2000×g for 10 minutes. The column contents were transferred to a clean 50 ml plastic tube, and nuclease free water was added to 25 ml total volume.

Example 11

Using Zeolite Membranes and Silica-Zeolite Composites

This Example shows that zeolite membrane, silica-zeolite composite membrane, and silica-zeolite composite in solution can remove DNA from RNA in tissue sample purifications. 1.61 g and 1.69 g frozen bovine liver were homogenized in 21.5 ml and 22.5 ml SV RNA Lysis Buffer (Promega), respectively, including 430 ul and 450 ul of 48.7% beta mercaptoethanol (BME, Promega) using a rotor stator homogenizer. The two homogenates were mixed together. All the tubes used in this example were polypropylene screw-cap centrifuge tubes.

2 ml aliquots of the bovine liver homogenate (lysate) were dispensed into 15 ml tubes and the remainder of the lysate was stored at −80° C. Four (4.0) ml DB4.36 was added to each of the tubes with lysate. DB4.36 is 3M NaCl, 0.36M $Na_3$ citrate.$2H_2O$, 0.1 mM EDTA (pH 8.0), and 0.0009% Blue dye (FD&C Blue #1) adjusted to a final pH of 4.0 with concentrated hydrochloric acid. The tubes were inverted 3-4 times and shaken to mix the samples. The tubes were incubated in a water bath at 70° C. for 5 minutes and then returned to a rack at room temperature. 0.5 ml S60 Silica-zeolite composite was added to each of two tubes (containing lysate and dilution buffer) and heated for 5 minutes at 70° C. and then returned to a rack at room temperature. After cooling these two S60 mixtures were shaken by inversion and transferred to a PureYield™ (PY) Binding column in tubes 4A and 4B. The remaining lysate/dilution buffer mixtures were inverted and shaken to mix one at a time and immediately transferred to columns in tubes 1A, 1B, 2A, 2B, 3A, 3B, 5A, 5B, 6, 7, 8A and 8B. The columns were swirled to mix. The columns in tubes 1A, 1B, 2A, 2B, 3A, 3B, 4A, 4B, 5A, 5B, 6 and 7 contain a membrane or zeolite powder as described in Table 7. The negative control tubes 8A and 8B have only PureYield™ binding columns without any added zeolite or silica. Tubes 1A and 1B were allowed to drip by gravity and the flow through was reapplied to the column 2 times. A small amount of flow through for tube 1A was lost in transfer.

TABLE 7

| Tube # | | Column type for clearing step |
|---|---|---|
| 1A, 1B | zeolite membrane (Aldrich, Type 3A) | PY Clearing Column |
| 2A, 2B | silica-zeolite membrane composite batch 2 (Aldrich, Type 3A) | PY Binding Column |
| 3A, 3B | silica-zeolite membrane composite batch 1 (Sigma, Type 13X cat#283592-1KG) | PY Binding Column |
| 4A, 4B | S60 Silica-zeolite composite in solution | PY Binding Column |
| 5A, 5B | zeolite powder (Aldrich Type 3A) | PY Binding Column |
| 6 | KOH 1 Water membrane (Sigma, Type 13X cat#283592-1KG) | PY Binding Column |
| 7 | KOH 2 HCl membrane (Sigma, Type 13X cat#283592-1KG) | PY Binding Column |
| 8A, 8B | Negative Control (no additional zeolite or silica) | PY Binding Column |

All tubes were centrifuged at 2000×g for 10 minutes at 24° C. Tubes 3A and 3B were centrifuged for an additional 5 minutes at 2,000×g at 24° C. Tubes 2A, 2B, 8A and 8B were centrifuged for an additional 2 times at 2000×g for 5 minutes. Negative control tube 8A had yet another centrifugation at 3000×g for 5 minutes at 24° C., but remained clogged so was not processed beyond this step. 4 ml isopropyl alcohol was added to the flow through in each tube and inverted and shaken well to mix. This mixture was poured into a correspondingly labeled PureYield™ Binding Column (Promega) attached to a vacuum manifold and vacuum was applied. Negative control tube 8B as well as tubes 6 and 7 clogged and so were not processed beyond this step.

After the mixture passed through the column, 20 ml and then 10 ml SV RNA Wash solution was added to the binding column with the vacuum applied each time until there was no standing wash solution on the column membrane. The vacuum was applied for an additional 3 minutes to dry the membrane. The binding columns were transferred to clean 50 ml tubes. To elute the RNA, 1 ml of nuclease-free water was applied to the binding membrane and incubated at 22° C. for 2 minutes. The columns were centrifuged at 2000×g for 3 minutes at 24° C.

FIGS. 9A and 9B were generated as follows. 10 ul of each sample was incubated at 37° C. for two hours with 2.0 ul RNase ONE™ ribonuclease enzyme (Promega) and 1.3 ul 10× RNase ONE™ buffer (Promega) to digest the RNA. After the incubation the RNase treated samples were each mixed with 2.5 ul Blue/Orange Loading Dye, 6× (Promega) and 10 ul of untreated sample mixed with 2.0 ul Blue/Orange Loading Dye, 6×. Each lambda marker lane had 2 ul of lambda DNA EcoRI/HindIII marker (Promega) mixed with 8 ul water and 2 ul Blue/Orange Loading Dye, 6×. Each 100 bp ladder lane had 2 ul 100 bp DNA ladder (Promega) mixed with 8 ul water and 2 ul Blue/Orange Loading Dye, 6×. All samples with loading dye were loaded on a 1×TBE, 1% agarose gel containing ethidium bromide.

The samples were loaded in the same order for FIGS. 9A and 9B, the only difference was that 9B samples were treated with RNase ONE™ ribonuclease while the 9A samples were untreated. The sample loading order is as follows: 1. Lambda DNA EcoRI/HindIII marker; 2. Blank; 3. Sample 1A, zeolite membrane; 4. Sample 1B, zeolite membrane; 5. Sample 2A, silica-zeolite membrane (Type 3A); 6. Sample 2B, silica-zeolite membrane (Type 3A); 7. Sample 3A, silica-zeolite membrane (Type 13X); 8. Sample 3B, silica-zeolite membrane (Type 13X); 9. Sample 4A, S60 Silica-zeolite composite; 10. Sample 4B, S60 Silica-zeolite composite; 11. Sample 5A zeolite powder (Type 3A); 12. Sample 5B zeolite powder (Type 3A); 13. Blank; 14. Lambda DNA EcoRI/HindIII marker; and 15. 100 bp DNA ladder. The gel in FIG. 9A demonstrated that RNA has been purified using different types of zeolite (Type 3A or Type 13X) in membrane form either by itself or as a silica-zeolite composite membrane as well as a silica-zeolite composite in solution or zeolite powder. The gel in FIG. 9B showed that no visible DNA co-purified with the RNA.

Example 12

Screening Zeolites

This example describes a method for screening zeolites for nucleic acid purification. In particular, this example describes screening different zeolites for the ability to leave RNA including small RNA in solution and to remove DNA. The initial screen (part A.) used a difficult lysate sample that has a lot of RNA, DNA and contaminants to challenge the zeolites. The second screen (part B) includes a subset of the zeolites from part A, as well as an additional brand (Praxair) of Molecular Sieves Type 13X which has the same synthesis source as Sigma catalog #3010. The second screen uses a typical lysate sample amount to examine the effectiveness of the zeolites under less stringent conditions. The dilution buffer employed was DB4 which is SV RNA Dilution Buffer Promega (Promega, 3M NaCl, 0.3M $Na_3$ citrate.$2H_2O$, 0.2% SDS, 0.1 mM EDTA (pH 8.0) and 0.0009% Blue dye (FD&C Blue #1)) with the final pH adjusted to pH 4.0 with concentrated hydrochloric acid.

Part A

TABLE 8

| Tube # | Zeolite Name | Source | Identification |
|---|---|---|---|
| 1, 2 | Molecular sieves, type 3A, <50 micron | Acros Organics, Fair Lawn, New Jersey, cat#214795000, C.A.S. 308080-99-1 | Acros 3A |
| 3, 4 | Molecular sieves, type 3A, powder, undried | Aldrich, St. Louis, MO, cat #233641-500G, C.A.S. 308080-99-1 | Aldrich 3A |
| 5, 6 | Molecular sieves, type 4A | Acros cat#214805000, C.A.S. 70955-01-0 | Acros 4A |
| 7, 8 | Molecular sieves, type 4A | Fluka cat#69836 | Fluka 4A |
| 9, 10 | Molecular sieves, Type 5A, <50 micrometers | Acros cat#214815000 C.A.S. 69912-79-4 | Acros 5A |
| 11, 12 | Molecular sieves, Type 5A, powder, undried | Aldrich cat#233676-1kg | Aldrich 5A |
| 13, 14 | Molecular sieves, Type 13x, powder, <50 micron | Acros cat# 269255000, C.A.S. 63231-69-6 | Acros 13X |
| 15, 16 | Molecular sieves, Type 13x, powder | Alfa Aesar/Lancaster, Pelham, NH, cat#L06232 | Alfa Aesar 13X |
| 17, 18 | Molecular sieves, UOP, Type 13x | Fluka, Switzerland, cat#69856 | Fluka 13X |
| 19, 20 | Molecular sieves, Type 13x, <10 um, powder | Sigma Chemical Co., St. Louis, MO, cat#M3010-250G | Sigma 13X, 3010 |
| 21, 22 | Molecular sieves, Type 13x, powder | Sigma cat#283592-1kg | Sigma 13X #2 |
| 23, 24 | Molecular sieves, Organophilic | Aldrich cat#419095-100G | Aldrich organophilic |
| 25, 26 | Zeolite | MP Biomedicals, LLC, Aurora, OH, cat#193902 | MP Bio zeolite |

The following protocol was employed. 2 ml SV RNA Lysis Buffer (Promega) including 20 ul 48.7% beta mercaptoethanol (BME, Promega) per milliliter buffer was added per 600 mg frozen bovine spleen and homogenized using a rotor stator homogenizer. The homogenized lysate was divided into tubes and stored at minus 80° C. Tubes containing bovine spleen lysate were removed from the −80° C. freezer and thawed in water at 4° C. 2 ml aliquots of the bovine lysate were dispensed into 15 ml tubes. 4 ml DB4 was added and 0.5 g zeolite (see the Table 8 above for the type of zeolite added to the tube) was added to each 15 ml tube. The 15 ml tubes were inverted and shaken well to mix the samples and then incubated in a water bath at 70° C. for 5 minutes. The 15 ml tubes were returned to a rack at room temperature.

For each sample a PureYield™ Clearing Column (Promega) was inserted in 50 ml polypropylene catch tube. One at a time, the 15 ml tubes were inverted and shaken to mix and then immediately poured into the PureYield™ Clearing Column in the corresponding labeled tube. These clearing columns in catch tubes were centrifuged at 2000×g for 10 minutes at 24° C. The Clearing Columns were discarded. 4 ml isopropyl alcohol was added to the flow through in each tube and inverted and shaken 2-4 times to mix. This mixture was poured into a PureYield™ Binding Column (Promega) in a labeled 50 ml tube and spun in a centrifuge at 2000×g at 24° C. Tubes 9 and 17-26 were centrifuged an additional 3 minutes. Tubes 18 and 22-26 were centrifuged a third time for an additional 3 minutes.

The binding columns were connected to a vacuum manifold (Promega). The columns were washed with 20 ml and then 10 ml SV RNA Wash Solution (Promega) applying a vacuum. After all wash solution had flowed through, the vacuum was applied for an additional 3 minutes to dry the column membrane. The binding columns were transferred to clean 50 ml tubes. To elute the RNA, 1 ml of nuclease-free water was applied to the binding membrane and incubated at 22° C. for 3 minutes with the tube capped. The columns were spun in a centrifuge at 2000×g for 3 minutes.

To evaluate the eluates the samples were loaded on a gel. 10 ul of each elution was incubated at 37° C. for two hours with 2.0 ul RNase ONE™ ribonuclease enzyme (Promega) and 1.3 ul 10× RNase ONE™ buffer (Promega) to digest the RNA. The RNase ONE™-treated samples were stored at −20° C. 2.5 ul of Blue/Orange 6× loading dye (Promega) was added to the thawed RNase ONE™-treated samples. 2 ul of Blue/Orange 6× loading dye was added to 10 ul of untreated sample. Each lambda marker lane has 2 ul of lambda DNA EcoRI/HindIII marker (Promega) mixed with 8 ul water and 2 ul Blue/Orange Loading Dye, 6×. Each 100 bp ladder lane has 2 ul 100 bp DNA ladder (Promega) mixed with 8 ul water and 2 ul Blue/Orange Loading Dye, 6×. 10 ul of lysate was mixed with 2 ul Blue/Orange Loading Dye, 6×. The lysate and all samples with loading dye were loaded on a 1×TBE 1% agarose gel containing ethidium bromide.

The gel in FIG. 10A shows the presence of RNA in all samples, with some differences in the presence of small rRNA purified. The gel also shows differences in the amount of DNA carried through the purification process. The most efficient zeolite tested here for capturing small rRNA is Sigma molecular sieves Type 13X (Sigma, cat #283592). The most efficient zeolite tested for lack of DNA is the Acros molecular sieves type 3A. The molecular sieves Type 5A by Acros did slightly better than Type 5A by Aldrich but both show a certain amount of DNA as well as a white opaque contaminant visible in the eluate in tubes 10, 11 and 12 (small amount in tube 9). The top row and bottom rows in FIG. 10A are the same samples loaded in the same order, except where noted. The bottom row samples have been treated with RNase ONE™, while the bottom row contains an additional lane with lysate that has not been treated with RNase. The lanes in FIG. 10A were loaded in the following order: 1. Lambda DNA EcoRI/HindIII marker, 2. Blank, 3. Acros 3A, 4. Acros 3A, 5. Aldrich 3A, 6. Aldrich 3A, 7. Acros 4A, 8. Acros 4A, 9. Fluka 4A, 10. Fluka 4A, 11. Acros 5A, 12. Acros 5A, 13. Aldrich 5A, 14. Aldrich 5A, 15. Blank, 16. Lambda DNA EcoRI/HindIII marker, 17. 100 bp DNA ladder, 18. Blank, 19. Acros Type 13X, 20. Acros Type 13X, 21. Alfa Aesar Type 13X, 22. Alfa Aesar Type 13X, 23. Fluka Type 13X, 24. Fluka Type 13X, 25. Sigma Type 13X, #3010, 26. Sigma Type 13X,

3010, 27. Sigma Type 13X, #2, 28. Sigma Type 13X, #2, 29. Aldrich Organophilic, 30. Aldrich Organophilic, 31. MP Bio zeolite, 32. MP Bio zeolite, 33. Blank, 34. Lambda DNA EcoRI/HindIII marker, 35. Top: 100 bp DNA ladder, 35. Bottom: Blank, 36. Blank, 37. Top: Blank, 37. Bottom: Lysate.

Part B

For part B, the same protocol was followed as in part A with the following exceptions: (1) The frozen bovine spleen lysate was diluted with an equal volume of SV RNA Lysis Buffer with BME; (2) The lysate and dilution buffer were mixed prior to addition of the powder zeolite; (3) The 70° C. incubation was for 3 minutes; (4) Only one centrifugation was required for the clearing column step; (5) The RNase treatment of samples was a one-hour incubation only.

TABLE 9

| Tube # | Zeolite Name | Source | Identification |
|---|---|---|---|
| 1, 2 | Molecular sieves, type 3A, <50 micrometers | Acros Organics, cat#214795000, C.A.S. 308080-99-1 | Acros 3A |
| 3, 4 | Molecular sieves, type 3A, powder, undried | Aldrich, cat #233641-500G | Aldrich 3A |
| 5, 6 | Molecular sieves, Type 13x, powder | Alfa Aesar/Lancaster, cat#L06232 | Alfa Aesar 13X |
| 7, 8 | Molecular sieves, Type 13X, powder | Praxair, Danbury, CT. part#MS-1329 | Praxair 13X |
| 9, 10 | Molecular sieves, Type 13x, <10 um, powder | Sigma Chemical Co., cat#M3010-250G | Sigma 13X, 3010 |
| 11, 12 | Molecular sieves, Type 13x, powder | Sigma cat#283592-1kg | Sigma 13X #2 |

The gel in FIG. 10B shows that even the under less stringent conditions of the second screen, the Aldrich type 3A still outperforms the Acros Type 3A for removing DNA while leaving RNA in solution. The Alfa Aesar Type 13X does better in the second screen for removing DNA contamination than in the more stringent screen of part A. As expected, the Praxair zeolite and the Sigma Type 13X cat #3010 (same description, synthesized by the same company) behaved similarly by retaining the small rRNA and reducing the DNA contamination. The Sigma Type 13X cat #283592 gave results similar to the first screen and to the Aldrich Type 3A of the second screen. The lanes in FIGS. 10B (untreated samples) and 10C (RNase-treated samples) were loaded in the following order: 1. Lambda DNA EcoRI/HindIII marker; 2. Blank; 3. Acros 3A; 4. Acros 3A; 5. Aldrich 3A; 6. Aldrich 3A; 7. Alfa Aesar 13X; 8. Alfa Aesar 13X; 9. Praxair 13X; 10. Praxair 13X; 11. Sigma Type 13X, #3010; 12. Sigma Type 13X, #3010; 13. Sigma Type 13X, #2; 14. Sigma Type 13X, #2; 15. Blank; 16. Lambda DNA EcoRI/HindIII marker; 17. 100 bp DNA ladder Example 13

Generating Magnetic and Paramagnetic Zeolite Particles

This Example describes the production of $Fe_3O_4$-zeolite magnetic particles. 3 grams of zeolite (Aldrich cat #233641) was placed into a 50 ml tube, and 1 gram of $Fe_3O_4$ (Aldrich 31,006-9) was added. The contents were mixed by vortexing, and 5 ml of 56% KOH was added, followed by additional vortexing. The contents were poured into a Promega clearing column inserted into a 50 ml plastic collection tube, and centrifuged at 2000×g for 2 minutes in a swinging bucket rotor (all subsequent spins as well). Then 3 ml of 1N HCl was added, and the column was centrifuged for 2 minutes at 2000×g. 3 ml of 1N HCl was added to the column, and it was centrifuged at 2000×g for 2 minutes. 5 ml of nuclease free water was added, and the column spun again for 2 minutes at 2000×g. After discarding the flowthrough from the collection tube, an additional 5 ml of nuclease free water was added to the column, and the column/tube was spun again for 2 minutes at 2000×g.

The following tube was used as a balance in the centrifuge with the above tube, and was used for MagneSil®-zeolite magnetic particle production. 10 ml of Promega MagneSil® (100 mg per ml) was added to a Promega clearing column, and the contents centrifuged 2000×g for 2 minutes in a swinging bucket rotor (all subsequent spins as well). The flowthrough was discarded, and the resulting 1 gm of MagneSil® was added to a 50 ml plastic tube containing 3 gm of zeolite 3A (Aldrich cat #233641), and the contents were mixed by vortexing. Then 5 ml of 56% KOH was added, followed by additional vortexing. The contents were poured into a Promega clearing column, inserted into a 50 ml collection tube, and centrifuged at 2000×g for 2 minutes. Then 3 ml of 1N HCl was added, and the column was centrifuged for 2 minutes at 2000×g. 3 ml of 1N HCl was added to the column, and it was centrifuged at 2000×g for 2 minutes. 5 ml of nuclease free water was added, and the column spun again for 2 minutes at 2000×g. After discarding the flowthrough from the collection tube, an additional 5 ml of nuclease free water was added, and the column spun again for 2 minutes at 2000× g.

The above $Fe_3O_4$-zeolite magnetic particles and the above MagneSil®-zeolite particles were each removed from their respective columns and resuspended in 15 ml of nuclease free water, each, in clean 50 ml plastic tubes. The tubes were magnetized for 30 seconds with mixing, so that most of the particles were captured by the magnet. The remaining solution, for each particle type, was transferred to a clean 50 ml tube which was then magnetized for 90 seconds with mixing. The particles magnetically captured were labeled "first cut" and the remaining particles were transferred to a clean 50 ml tube and the contents magnetized for 5 minutes with occasional mixing. The particles magnetically captured in the final tube were labeled "second cut," and the remaining liquid was discarded. The particles produced by the "second cut" were lighter in color than the "first cut" particles indicating a greater zeolite content on average. The initially captured particles were darker in color than the "first cut" particles. Using this method, magnetic (or paramagnetic) particles with greater zeolite content were enriched for by collecting particles with a slower magnetic response time. Materials that were not magnetically responsive were discarded at the end of the procedure.

Example 14

$Fe_3O_4$-Zeolite Magnetic Particle and MagneSil®-Zeolite Magnetic Particle Purification This Examples describes the use of $Fe_3O_4$ particles coated with zeolite and MagneSil® particles coated with zeolite to purify RNA from lysate. A HEK 293 Dallas human cell culture was lysed with 4 ml SV RNA Lysis Buffer (Promega) including 80 ul of 48.7% beta mercaptoethanol (BME, Promega). The flask was gently shaken with the lysis buffer to lyse the cells. The lysate was stored at −70° C.

The making of the zeolite-coated particles was previously described in Example 13. This experiment used the $Fe_3O_4$- zeolite magnetic particles and the MagneSil®-zeolite magnetic particles initially captured with magnetization, as well as the Fe$_3$O$_4$-zeolite magnetic particles "second cut". The magnetic-zeolite particles were suspended in DB4.36 at 100 mg/ml. Zeolite Molecular Sieve Type 13X (Praxair) was also suspended in DB4.36 at 100 mg/ml. DB4.36 is 3M NaCl, 0.36M Na$_3$ citrate.2H$_2$O, 0.1 mM EDTA (pH 8.0), and 0.0009% Blue dye (FD&C Blue #1), adjusted to a final pH of 4.0 with concentrated hydrochloric acid.

Twelve 50 ul aliquots of the human cell lysate were dispensed into a 96-well microplate U-form (Greiner bio-one cat #650101) containing 100 ul DB4.36 per well, and mixed. 50 ul of zeolite or magnetic-zeolite particles (100 mg/ml) were added and mixed. The plate was heated in a hybridization oven at 70° C. for 15 minutes. The plate was then placed on a MagnaBot® 96 Magnetic Separation Device (Promega) to separate the paramagnetic particle from the cleared lysate. The cleared lysates were transferred to clean wells in the 96-well plate. The Fe$_3$O$_4$-zeolite magnetic particles (second cut) were transferred two subsequent times to clean wells on the MagnaBot® to separate the particles from the cleared lysate. The Type 13X zeolite samples (non-paramagnetic) were transferred to a Spin-X® centrifuge tube filter (Corning Inc. cat #8160) and spun twice in a microcentrifuge at 8000 rpm for 1 minute each, plus an additional spin at 12,000 rpm for 1 minute. The cleared lysate was transferred to the 96-well plate. 10 ul of cleared lysate was removed from each sample for analysis.

100 ul of isopropanol was added to each well containing cleared lysate from Fe$_3$O$_4$-zeolite particles (main) and MagneSil®-zeolite particles (main). 60 ul of isopropanol was added to each well containing the cleared lysate from the Fe$_3$O$_4$-zeolite particles (second cut) and zeolite Type 13X, because the volume was just over half of the volume of the cleared lysate from Fe$_3$O$_4$-zeolite particles (main) and MagneSil®-zeolite particles (main). 10 ul of MagneSil Blue (Promega cat #A2201) was added to each cleared lysate and mixed. The samples were incubated at 22° C. for 20 minutes. The plate was placed on the MagnaBot® magnetic separator and after the paramagnetic particles separated, the lysate was removed. The paramagnetic particles were washed twice with 300 ul SV RNA Wash Solution (Promega cat #Z309C) using the MagnaBot® magnetic separator. The nucleic acid was eluted with 50 ul of nuclease-free water incubating for 15 minutes at 50° C. on the heat block.

FIGS. 11A, 11B and 11C were generated as follows. 10 ul of each eluate was incubated at 37° C. for 3 hours with 2.0 ul RNase ONE™ ribonuclease enzyme (Promega part #M426C) and 1.3 ul 10× RNase ONE™ buffer (Promega part #M217A) to digest the RNA. After the incubation the RNase treated samples were each mixed with 2.5 ul Blue/Orange Loading Dye, 6× (Promega) and 10 ul of untreated sample mixed with 2.0 ul Blue/Orange Loading Dye, 6×. 10 ul of cleared lysate or 10 ul of lysate was mixed with 2.0 ul Blue/Orange Loading Dye, 6×. Each lambda marker lane had 2 ul of lambda DNA EcoRI/HindIII marker (Promega) mixed with 8 ul water and 2 ul Blue/Orange Loading Dye, 6×. Each 100 bp ladder lane had 2 ul 100 bp DNA ladder (Promega) mixed with 8 ul water and 2 ul Blue/Orange Loading Dye, 6×. All samples with loading dye were loaded on a 1× TBE, 1% agarose gel containing ethidium bromide.

FIGS. 11A and B demonstrated that RNA is purified using zeolite-coated MagneSil® particle or zeolite-coated Fe$_3$O$_4$ particles. FIG. 11B demonstrated that the bands seen in FIG. 11A were removed with RNase treatment and that DNA was not detected in the samples on the gel. FIG. 11C demonstrated that the DNA was not present in the cleared lysate, but removed from the lysate during the magnetic zeolite clearing step.

The samples were loaded in the same order for FIGS. 11A and 11B. The only differences were that 11B samples were treated with RNase ONE™ ribonuclease while the 11A samples were untreated, and that 11B has lysate loaded in well 19 and an addition Lambda DNA Marker in well 20. The gels in FIGS. 11A and B were loaded in the following order: 1. Lambda DNA EcoRI/HindIII marker; 2. Blank; 3. MagneSil®-zeolite particles (main)-1; 4. MagneSil®-zeolite particles (main)-2; 5. MagneSil®-zeolite particles (main)-3; 6. Fe$_3$O$_4$-zeolite particles (main)-1; 7. Fe$_3$O$_4$-zeolite particles (main)-2; 8. Fe$_3$O$_4$-zeolite particles (main)-3; 9. Fe$_3$O$_4$-zeolite particles (second cut)-1; 10. Fe$_3$O$_4$-zeolite particles (second cut)-2; 11. Fe$_3$O$_4$-zeolite particles (second cut)-3; 12. Zeolite (Type 13X)-1; 13. Zeolite (Type 13X)-2; 14. Zeolite (Type 13X)-3; 15. Blank; 16. Lambda DNA EcoRI/HindIII marker; 17. 100 bp DNA ladder; 18. Blank 19. Lysate (only in FIG. 11B); and 20. Lambda DNA EcoRI/HindIII marker (only in FIG. 11B). For FIG. 11C, which shows the cleared lysate, and lysate, the sample loading order was as follows, with two blank lanes between each sample and seven blank lanes between the last sample and the lysate: 1. MagneSil®-zeolite particles (main) cleared lysate-1; 2. MagneSil®-zeolite particles (main) cleared lysate-2; 3. MagneSil®-zeolite particles (main) cleared lysate-3; 4. Fe$_3$O$_4$-zeolite particles (main) cleared lysate-1; 5. Fe$_3$O$_4$-zeolite particles (main) cleared lysate-2; 6. Fe$_3$O$_4$-zeolite particles (main) cleared lysate-3; 7. Fe$_3$O$_4$-zeolite particles (second cut) cleared lysate-1; 8. Fe$_2$O$_3$-zeolite particles (second cut) cleared lysate-2; 9. Fe$_3$O$_4$-zeolite particles (second cut) cleared lysate-3; 10. Zeolite (Type 13X) cleared lysate-1; 11. Zeolite (Type 13X) cleared lysate-2; 12. Zeolite (Type 13X) cleared lysate-3 13. Lysate.

Example 15

Purifying RNA from a RNA/DNA Mixture Using Magnetic Zeolite Particles

Figure 12:
FIG. 12 shows the results from Example 15, which describes the use of magnetic zeolite particles to generate a purified RNA sample.

This Example describes the use of magnetic zeolite particles to generate a purified RNA sample. A mixture of RNA and DNA was prepared by combining 10 ul of 500 ug/ml kanamycin mRNA (Promega cat #C1381) with 100 ul of 1 kb DNA ladder (Promega cat #G571A). Magnetic zeolite particles made (as described in Example 13) were added to 1.5 ml Eppendorf tubes, 20 mg of particles per tube. To each tube was added (in order): 10 ul of dilution buffer (DB4), 5 ul Lysis buffer, and 6 ul of the above RNA/DNA mixture. Tubes were capped, mixed and heated for 5 minutes at 70° C., then cooled to 21° C. for 5 minutes, and then placed on a magnetic separation stand for 10 minutes. 5 ul of each magnetically separated solution was added per well on a 1% agarose gel, as shown in FIG. 12. Due to considerable salt/buffer in many samples, there is a "salt front" that curves sample migration in the gel. The lanes in FIG. 12 were loaded as follows: 1. Fe$_3$O$_4$ control (no zeolite coating); 2 Fe$_3$O$_4$-zeolite "main;" 3. Fe$_3$O$_4$-zeolite "first cut;" 4 Fe$_3$O$_4$-zeolite "second cut," 5. RNA/DNA mix, no particle treatment; 6. kanamycin mRNA standard; 7 MagneSil-zeolite "main," 8. MagneSil-control, not coated with zeolite; 9. blank; 10. MagneSil-zeolite "first cut;" 11 MagneSil-zeolite "second cut;" and 12. blank. The gel in FIG. 12 shows that magnetic zeolites removed DNA from a RNA/DNA mixture, using magnetic separation to purify RNA away from DNA.

Example 16

The Effect of GTC on Removal of DNA From a RNA/DNA Mixture

This Example describes the effect of guanidine on RNA purification with zeolites. A mixture of RNA and DNA was prepared by combining 10 ul of 500 ug/ml kanamycin mRNA (Promega cat #C1381) with 25 ul of 1 kb DNA ladder (Promega cat #G571A). 100 mg of zeolite 13X (Sigma-Aldrich cat #283592) was added per column, for two columns (Costar cat #8169, Corning, N.Y. (containing a 0.22 micron nylon membrane)), and 100 mg of zeolite 3A (Aldrich cat #233641) per Costar 8169 column, for two columns. All columns were placed in 1.5 ml microfuge tubes.

Figure 13:
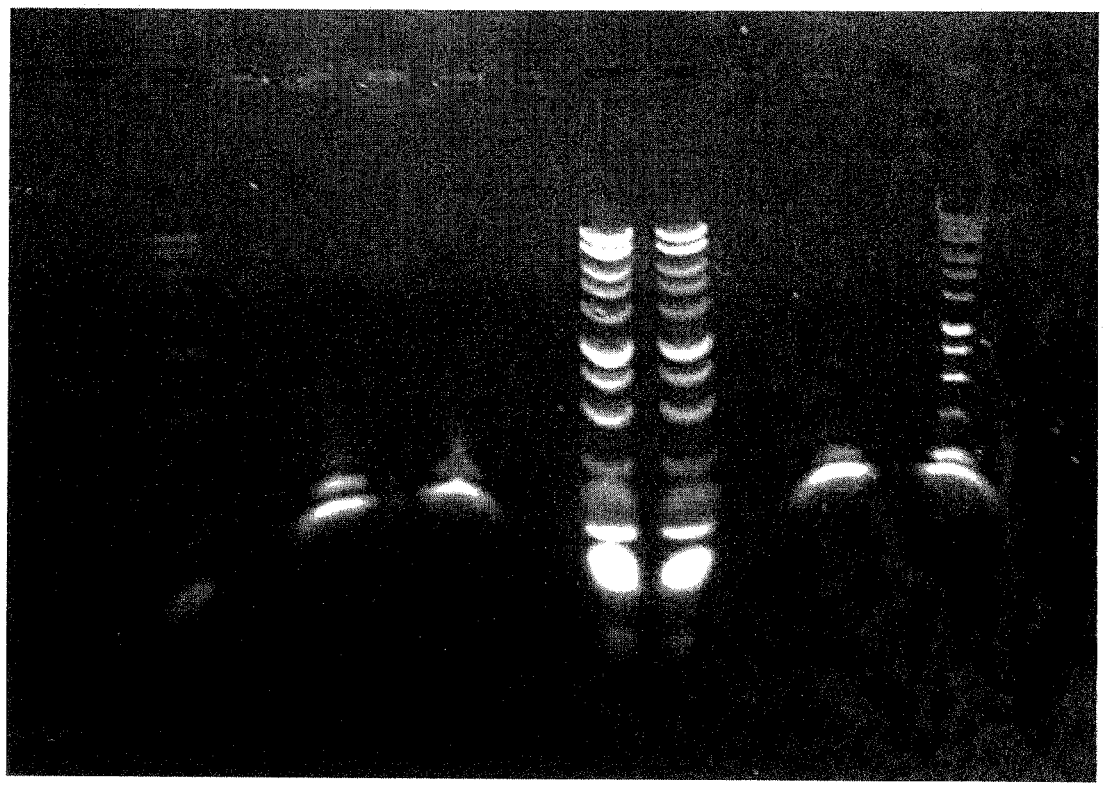
FIG. 13 shows the results of Example 16, which describes the effect of guanidine on RNA purification with zeolites.

To columns 13X-DB4-only and 3A-DB4-only, 100 ul of dilution buffer DB4 (see Example 3) was added. For samples 13X-plus-Lysis and 3A-plus-Lysis, 100 ul DB4 and 50 ul of Lysis solution (4M guanidine thiocyanate, 10 mM Tris, pH 7.5, with beta-mercaptoethanol added separately to a final concentration of 0.974% (v/v)), was added per column. The contents of all 4 columns were mixed, and 5 ul of the RNA/DNA mix (above) was added per column. The tubes were capped, and the tubes were incubated at 70° C. for 3 minutes, then cooled to 21° C. for 5 minutes. The tubes were centrifuged at 8000×g for 60 seconds. 10 ul of the flowthroughs were loaded per well in a 1% agarose non-denaturing gel. The results are shown in FIG. 13. The lanes in FIG. 13 were loaded in the following order: 1. and 2. were blank; 3. $\frac{1}{10}^{th}$ diluted RNA/DNA mix standard; 4. blank; 5. zeolite 13X plus Lysis; 6. blank; 7. 13X DB4 only; 8. blank; 9. undiluted RNA/DNA mix standard; 10. 50% diluted RNA/DNA mix standard; 11. blank; 12. zeolite 3A-plus-Lysis; 13. blank; and 14. 3A-DB4-only. The gel in FIG. 13 shows that zeolite 13X removed DNA in dilution buffer BD4 only, as well as in the DB4-plus-Lysis sample. Zeolite 3A partially removed DNA, leaving RNA, and the DB4-plus Lysis sample showed no visually detectable DNA, leaving the RNA in the flowthrough. As such, this example shows the purification of RNA (removal of DNA) with zeolites and dilution buffer alone, and enhanced purification of RNA with zeolites and a buffer containing guanidine.

Example 17

Dilution Buffer pH Range, Used with Liver Lysates

This example describes various pH ranges for citrate buffer that are effective for purifying RNA with zeolites. 5.71 g frozen bovine liver tissue was homogenized in 114.2 ml SV RNA Lysis Buffer (Promega cat #Z3051), including 2.28 ml of 48.7% beta mercaptoethanol (BME, Promega part #Z523A) using a rotor stator homogenizer. All the tubes used in this example were polypropylene screw-cap centrifuge tubes. 2 ml aliquots of the bovine liver homogenate (lysate) were dispensed into 15 ml tubes and the remainder of the lysate was stored at −80° C. Four (4.0) ml buffer was added to each of the tubes with lysate. The citrate buffer was 3M NaCl, 0.36M Na$_3$ citrate.2H$_2$O adjusted to a final pH ranging from 2.9 to 6.4 with concentrated hydrochloric acid. Two negative control tubes had no buffer added to the lysate. All 15 ml tubes were inverted 3-4 times and shaken to mix the samples. The tubes were incubated in a water bath at 70° C. for 5 minutes and then returned to a rack at room temperature to cool for 5 minutes.

For each sample a PureYield Clearing Column (Promega) was inserted in 50 ml polypropylene catch tube (caps discarded). One at a time, the 15 ml tubes were inverted and shaken to mix and then immediately poured into the PureYield Clearing Column in the corresponding labeled tube. These clearing columns in catch tubes were centrifuged at 2000×g for 10 minutes at 24° C. The Clearing Columns were discarded. 4 ml isopropyl alcohol was added to the flow through in each tube and inverted and shaken well to mix. This mixture was poured into a correspondingly labeled PureYield™ Binding Column (Promega cat #Z3091) attached to a vacuum manifold and vacuum was applied. The negative control tubes without buffer clogged as well as tube 2.9B (citrate buffer at pH 2.9) and so were not processed beyond this step.

After the mixture passed through the column, 20 ml and then 10 ml SV RNA Wash solution was added to the binding column with the vacuum applied each time until there was no standing wash solution on the column membrane. The vacuum was applied for an additional 3 minutes to dry the membrane. The binding columns were transferred to clean 50 ml tubes. To elute the RNA, 1 ml of nuclease-free water was applied to the binding membrane and incubated at 22° C. for 2 minutes. The columns were centrifuged at 2000×g for 3 minutes at 24° C.

FIGS. 14A and 14B were generated as follows. 10 ul of each sample was incubated at 37° C. for 1.5 hours with 2.0 ul RNase ONE™ ribonuclease enzyme (Promega) and 1.3 ul 10× RNase ONE™ buffer (Promega) to digest the RNA. After the incubation the RNase treated samples were each mixed with 2.5 ul Blue/Orange Loading Dye, 6× (Promega) and 10 ul of untreated sample mixed with 2.0 ul Blue/Orange Loading Dye, 6×. Each lambda marker lane had 2 ul of lambda DNA EcoRI/HindIII marker (Promega) mixed with 8 ul water and 2 ul Blue/Orange Loading Dye, 6×. Each 100 bp ladder lane had 2 ul 100 bp DNA ladder (Promega) mixed with 8 ul water and 2 ul Blue/Orange Loading Dye, 6×. All samples with loading dye were loaded on a 1×TBE, 1% agarose gel containing ethidium bromide (Cambrex).

The gel in FIG. 14A (untreated samples) was loaded in the following order: 1. Lambda DNA EcoRI/HindIII marker; 2. Blank; 3. pH 2.9A; 4. blank; 5. pH 3.4A; 6. pH 3.4B; 7. pH 4.1A; 8. pH 4.1B; 9. pH 4.6A; 10. pH 4.6B; 11. pH 5.0A; 12. pH 5.0B; 13. pH 5.5A; 14. pH 5.5B; 15. pH 6.0A; 16. pH 6.0B; 17. pH 6.4A; 18. pH 6.4B; 19. Lambda DNA EcoRI/HindIII marker; and 20. 100 bp DNA ladder. The gel in FIG. 14B (RNase-treated samples) was loaded in the following order: 1. Lambda DNA EcoRI/HindIII marker; 2. 100 bp DNA ladder; 3. Blank; 4. pH 2.9A, Treated with RNase; 5. pH 3.4A, Treated with RNase; 6. pH 3.4B, Treated with RNase; 7. pH 4.1A, Treated with RNase; 8. pH 4.1B, Treated with RNase; 9. pH 4.6A, Treated with RNase; 10. pH 4.6B, Treated with RNase; 11. pH 5.0A, Treated with RNase; 12. pH 5.0B, Treated with RNase; 13. pH 5.5A, Treated with RNase; 14. pH 5.5B, Treated with RNase; 15. pH 6.0A, Treated with RNase 16. pH 6.0B, Treated with RNase; 17. pH 6.4A, Treated with RNase; 18. pH 6.4B, Treated with RNase; 19. Blank; and 20. Lambda DNA EcoRI/HindIII marker. FIG. 14A demonstrates that RNA has been purified away from DNA at a citrate buffer pH ranging from 3.4 to 5.0, while citrate buffer pH range from 5.5 to 6.4 purifies both RNA and DNA. FIG. 14B demonstrates that no visible DNA co-purified with the RNA at pH 3.4-5.0, while DNA is present at pH 5.5-6.4.

Example 18

RNA Purification Employing Various pH Ranges

Figure 15:
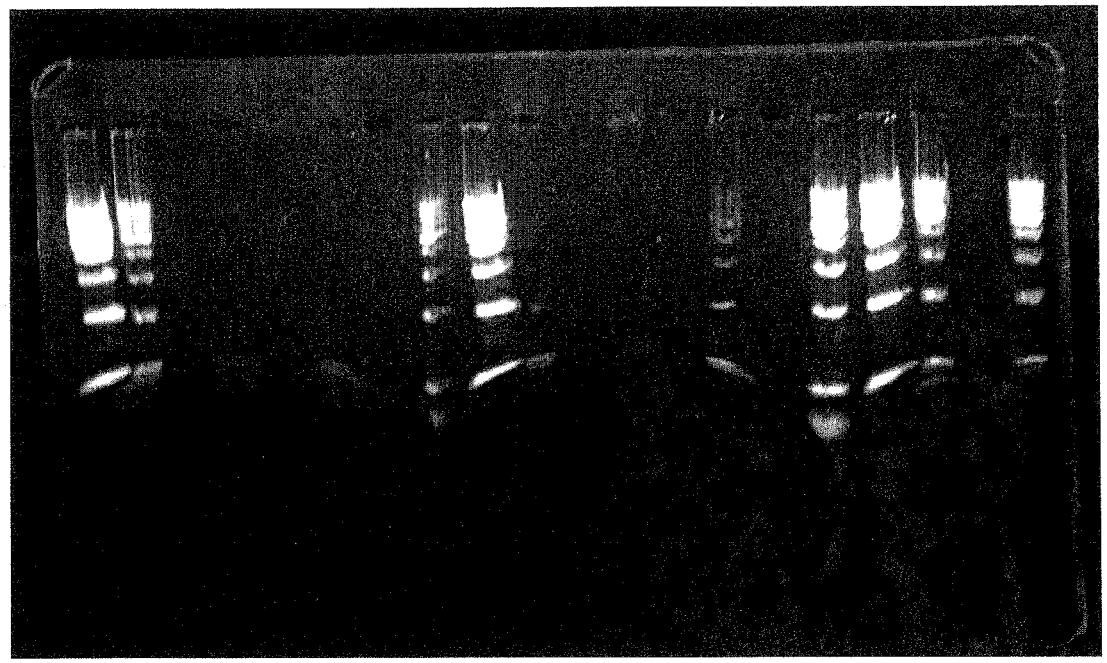
FIG. 15 shows the results of Example 18, which describes the results of using various pH ranges for citrate buffers on the selective removal of DNA from mixtures of RNA and DNA.

This example describes the removal of DNA from a mixture of RNA and DNA using zeolites and citrate buffer at various pH ranges. A mixture of RNA and DNA was prepared by adding 150 ul of 1 kb DNA ladder (Promega cat #G571A) to 10 ug of kanamycin mRNA (Promega cat #C1381). 10 mg of zeolite 13X ((Sigma-Aldrich cat #283592) was added per column to 8 columns (Costar #8169) nested in 1.5 ml tubes, each column containing 100 ul of 0.6M citrate buffer at a different pH: (1) 5.0, (2) 5.0, (3) 5.1, (5) 5.2 plus an additional 50 ul of Lysis buffer (4M guanidine thiocyanate, 10 mM Tris pH 7.5, 0.97% beta-mercaptoethanol), (6) pH 5.3, (7) pH 5.5 and (8) pH 6.4. 10 ul of the above RNA/DNA mix was added per column, and the tubes capped and incubated at 70° C. for 3 minutes (except sample (1) which was kept at room temperature). Samples were incubated at 22° C. for 5 minutes, then centrifuged at 8000×g for 2 minutes. 10 ul of the flowthrough was run per well on a 1% agarose, TBE non-denaturing gel. The resulting gel photo is shown below in FIG. 15. The lanes in FIG. 15 were loaded as follows: 1. RNA/DNA mixture, standard; 2. 0.6M citrate pH 5.0, no 70° C. incubation; 3. blank; 4. 0.6M citrate pH 5.0, with 70° C. incubation; 5. blank; 6. 0.6M citrate pH 5.1; 7. blank; 8. RNA/DNA mixture, standard; 9. 1 kb DNA ladder, standard; 10. 0.6M citrate pH 5.2; 11. blank; 12. 0.6M citrate pH 5.2 plus lysis solution; 13. blank; 14. 0.6M citrate pH 5.3; 15. blank; 16. 0.6M citrate pH 5.5; 17. 1 kb DNA ladder, standard; 18. 0.6M citrate pH 6.4; 19. blank; 20. 10 ul sample of lane 6 plus 1 ul of DNA/RNA mix. This result has demonstrated removal of DNA without RNA removal using 0.6M citrate buffers with pH ranging from pH 5.0 to pH 5.3.

Example 19

Removal of DNA from Protein Solutions

Figure 16:
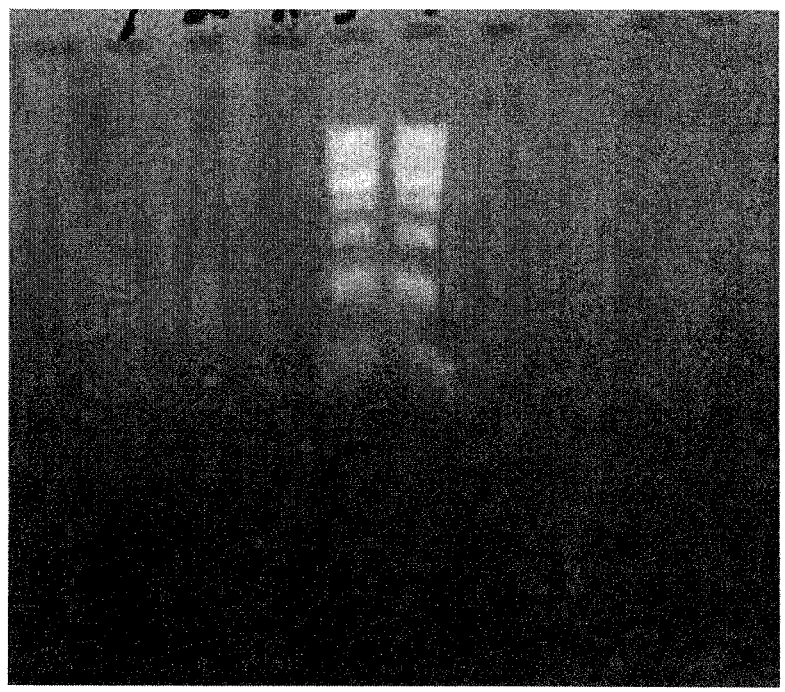
FIG. 16 shows the results of Example 19, which describes the results of removing DNA from a solution containing a mixture of protein and DNA.

This example describes the removal of DNA from protein solutions using zeolites. 10 mg of zeolite 13X ((Sigma-Aldrich cat #283592) was added per column to 2 columns (Costar #8169) nested in 1.5 ml tubes. 40 ul of 0.6M sodium citrate buffer, pH 4.6 was added to each column, and mixed. Then 10 ul of 1 kb DNA ladder (Promega cat #G571A), and 5 ul of CelluACE™ (Promega cat #FF3800) enzyme mixture was added and the contents mixed. Two columns (3 and 4) with identical contents to 1 and 2 above were prepared, except that they did not contain zeolite. All 4 tubes were capped and incubated at 50° C. for 20 minutes, then incubated at 21° C. for 5 minutes. The columns were microfuged at 8000×g for 2 minutes. 10 ul of each sample flowthrough was run per well, in a 1% TBE non-denaturing agarose gel. As shown in the FIG. 16 gel photo, the samples without zeolite have retained the DNA, but those containing zeolite have no visible DNA remaining in the sample. CelluACE activity was measured and the samples containing zeolite showed 866 units of activity, while those without zeolite (still containing DNA) showed 1306 units of activity. The resulting gel photo is shown in FIG. 16. The lanes in FIG. 16 were loaded as follows: 1. CelluACE plus zeolite A; 2. CelluACE plus zeolite B; 3. CelluACE, no zeolite A; and 4. CelluACE, no zeolite B.

Example 20

Isolation of Total RNA from Cow Heart Using an Acetate Dilution Buffer

This example describes the isolation of total RNA from cow heart tissue using an acetate dilution buffer. A cow heart lysate was prepared by homogenizing frozen tissue in 4° C. Lysis Buffer (4M guanidine thiocyanate, 10 mM Tris, pH 7.5, with beta-mercaptoethanol added separately to a final concentration of 0.974% (v/v)) with a PRO 200 rotor/stator homogenizer (PRO Scientific, Inc., Oxford, Conn.). The lysate was prepared at a concentration of 300 mg/ml (wet weight) and was stored in 10 ml aliquots at −70° C., until use. The frozen lysate was thawed at 4° C. The lysate was diluted to 150 mg/ml by adding an equal volume of 4° C. Lysis Buffer. Two 1 ml aliquots (150 mg of cow heart per isolation) were dispensed into plastic, 15 ml, screw capped tubes. An additional 1 ml of 4° C. lysis buffer was added to increase the final volume to 2 ml. Four ml of Acetate dilution buffer, designated "DB4.6A" (0.6M Na acetate (pH adjusted to 4.01 with glacial acetic acid), 3M NaCl; adjusted to a final pH of 4.0 with 10N NaOH), was added to each sample, mixed by inversion 3-4 times and then vortexed until homogeneous. One ml of clearing agent (2M NaCl, 0.1 mM EDTA (pH 8.0), 0.45 g/ml Molecular Sieves, type 13X (zeolite)) was added to each tube, mixed by inversion 2-3 times and then vortexed until homogeneous. The tubes were inverted 2-3 times a second time to resuspend the clearing agent, incubated at 70° C. in a hybridization oven for 5 minutes and then placed at ambient temperature (23-24° C.) for 5 minutes to cool.

The following steps were performed at ambient temperature (23-24° C.). Each mixture was shaken vigorously, vortexed and poured into a Promega clearing column, nested in a 50 ml collection tube. The columns were centrifuged in a swinging bucket rotor at 2,000×g, 23° C. for 10 minutes. The cleared lysates, containing RNA, were captured in 50 ml collection tubes. The sample debris, clearing agent and DNA were captured by the clearing column membrane and were discarded with the clearing columns. Four ml of isopropanol was added to each tube of cleared lysate and mixed by swirling the tube. Each mixture was applied to a Promega binding column, and attached to a vacuum manifold. A vacuum of approximately 15 in. Hg was applied to the columns. Each sample passed through the column, leaving the RNA bound to the binding column membrane. The membranes were washed twice with 20 ml and then 10 ml of wash solution (60 mM potassium acetate, 10 mM Tris, pH 7.5, 60% ethanol) to remove impurities and salts. The membranes were vacuum dried for at least 3 minutes on the vacuum manifold. The binding columns were transferred to 50 ml collection tubes for elution. One ml of nuclease-free water was applied to each membrane and incubated for 2-3 minutes at 23-24° C. The column assemblies were centrifuged, using a swinging bucket rotor, at 2,000×g for 3 minutes to collect the purified total RNA. The purified total RNA samples were analyzed by spectrophotometry and agarose gel analysis. Total RNA yields were determined by absorbance at 260 nm. The results are shown in table 10 below and FIGS. 17A and 17B.

TABLE 10

Total RNA Yield from Cow Heart Using an Acetate Dilution Buffer.

| Sample ID | Total RNA Yield (µg) |
| --- | --- |
| H150 1 | 18.4 |
| H150 2 | 15.6 |

FIG. 17A shows a gel Analysis of purified total RNA from cow heart using an acetate dilution buffer. RNA samples were analyzed by electrophoresis on a native, 1% agarose, 1×TBE gel, stained with ethidium bromide. Ten µl of each sample was loaded per lane. The image was collected using an Alpha Innotech FluorChem™ Imaging System. The lanes of the gel are as follows: Lane 1: H150 1; Lane 2: H150 2. Lane M was Promega's 1 kb DNA Ladder (Cat. #G5711), 10,000 bp, 8,000 bp, 6,000 bp, 5,000 bp, 4,000 bp, 3,000 bp, 2,500 bp, 2,000 bp, 1,500 bp, 1,000 bp, 750 bp, 500 bp, 253 bp and 250 bp. Representative size markers are indicated. The undenatured 23S ribosomal RNA, 16S ribosomal RNA and small RNAs are indicated by arrows.

FIG. 17B shows the results of a DNA contamination assay of total RNA purified from cow heart using an acetate dilution buffer. Purified total RNA samples were digested with Promega's RNase ONE™ Ribonuclease (Cat. #M4265). A 15 μl digestion mix, containing 3 μl of 10× Reaction Buffer, 9 μl of Nuclease-Free Water and 3 μl of RNase ONE™ Ribonuclease (5-10 u/μl) was mixed with 15 μl of each total RNA sample. The digestions were incubated at 37° C. for 1 hour and then held at 4° C., until analyzed. The digests were analyzed by electrophoresis on a native, 1% agarose, 1×TBE gel, stained with ethidium bromide. Ten μl of each reaction was loaded per lane. The image was collected using an Alpha Innotech FluorChem™ Imaging System. Lanes of the gel are as follows: Lane 1: H150 1; Lane 2: H150 2. Lane M was Promega's 1 kb DNA Ladder (Cat. #G5711), 10,000 bp, 8,000 bp, 6,000 bp, 5,000 bp, 4,000 bp, 3,000 bp, 2,500 bp, 2,000 bp, 1,500 bp, 1,000 bp, 750 bp, 500 bp, 253 bp and 250 bp. Representative size markers are indicated. The undenatured 23S ribosomal RNA, 16S ribosomal RNA and small RNAs are indicated by arrows.

Example 21

The Effect of Heat on Removal of DNA From a RNA/DNA Mixture

This Example describes the effect of heat on RNA purification with zeolites. Frozen bovine spleen tissue was homogenized with 1.0 ml Lysis Solution per 300 mg tissue using a rotor stator homogenizer. The Lysis Solution was SV RNA Lysis Buffer (Promega Cat. #Z3051) with beta mercaptoethanol (BME, Promega Part #Z523A) added to a final concentration of 1%. The homogenate was divided into tubes and stored at minus 80° C. All the tubes used in this example were polypropylene screw-cap centrifuge tubes.

Tubes containing homogenized bovine spleen were removed from the −80° C. freezer and thawed in water at 4° C. The bovine spleen homogenates were combined and then diluted with an equal volume of the Lysis Solution. 2 ml aliquots of the diluted bovine spleen homogenate were dispensed into fourteen 15 ml tubes. Four (4.0) ml DB4.36–EDTA (minus EDTA) was added to each of tubes 1-6. DB4.36–EDTA is 3M NaCl and 0.36M $Na_3$ citrate.$2H_2O$ adjusted with concentrated hydrochloric acid to a final pH of 4.0. Four (4.0) ml DB4.36 (pH=3.8) was added to each of tubes 7-9. DB4.36 (pH=3.8) was made by adjusting the pH of DB4.36–EDTA with concentrated hydrochloric acid to a pH of 3.82. Four (4.0) ml DB4.36+EDTA was added to each of tubes 10-14. DB4.36+EDTA is 3M NaCl, 0.36M $Na_3$ citrate.$2H_2O$, 0.1 mM EDTA (pH 8.0), and 0.0009% Blue dye (FD&C Blue #1) adjusted with concentrated hydrochloric acid to a final pH of 4.0.

To tubes 1-3 was added 1 ml zeolite mixture, which consisted of 2M NaCl, 0.1 mM EDTA (pH 8.0) with zeolite type 13X added at a concentration of 0.42 g/ml. The 3 tubes were inverted 3-4 times and shaken to mix the samples. The 3 tubes were incubated in a water bath at 70° C. for 3 minutes and then returned to room temperature.

Tubes 4-9 were inverted 3-4 times and shaken to mix the samples. Tubes 4-9 were incubated in a water bath at 70° C. for 3 minutes and then returned to room temperature. After cooling for 5 minutes, 1 ml zeolite mixture which consisted of 2M NaCl, 0.1 mM EDTA (pH 8.0) with zeolite added at a concentration of 0.42 g/ml, was added to each of tubes 4-9 and then inverted 3-4 times and shaken to mix the samples.

To tubes 10-12 was added 1 ml zeolite mixture, which consisted of 2M NaCl, 0.1 mM EDTA (pH 8.0) with zeolite added at varying concentrations: tube 10 had 0.40 g/ml, tube 11 had 0.43 g/ml, and tube 12 had 0.50 g/ml. Tubes 10-12 were inverted 3-4 times and shaken to mix the samples. Tubes 10-12 were incubated in a water bath at 70° C. for 3 minutes and then returned to room temperature.

Tubes 13 and 14 were inverted 3-4 times and shaken to mix the samples. Both tubes were incubated in a water bath at 70° C. for 3 minutes and then returned to a rack at room temperature. After cooling for 5 minutes, 0.50 g zeolite powder was added to each of tubes 13 and 14 and then inverted 3-4 times and shaken to mix the samples.

For each sample a PUREYIELD Clearing Column (Promega) was inserted in a 50 ml polypropylene catch tube (cap discarded) labeled C1-C14. One at a time, the 15 ml tubes 1-14 were inverted and shaken to mix and then immediately poured into the PUREYIELD Clearing Column in the corresponding labeled tube. These clearing columns in catch tubes were centrifuged at 3000×g for 10 minutes at 22° C. Four (4) ml isopropyl alcohol was added to the flow through in each tube and inverted 2-4 times to mix. This mixture was poured into a PUREYIELD Binding Column (Promega Cat. #A245), labeled B1-B14, in a 50 ml tube and spun in a centrifuge at 3000×g at 22° C. for 10 minutes.

Each binding column was transferred to a fresh 50 ml tube. 20 ml SV RNA Wash Solution (Promega Cat. #Z3091) was added each binding column and centrifuged at 3,000×g for 6 minutes. The flow through was discarded. Then 10 ml SV RNA Wash Solution was added to each binding column and centrifuged at 3,000×g for 6 minutes. The flow through was discarded. Each binding column was transferred to clean 50 ml tubes.

To elute the RNA, 1 ml of Nuclease-Free Water (Promega Cat. #P119C) was applied to each binding membrane and incubated at 22° C. for 1 minute. The columns were centrifuged at 3000×g for 2 minutes (RNA elution 1). Each column was transferred to a fresh 50 ml tube and the elution was repeated (RNA elution 2).

RNase ONE™ Ribonuclease Treatment

For each of the RNA elution 1 samples listed above, 10 ul of sample was added to 1.2 ul of RNase ONE 10× Buffer (Promega) in a PCR strip tube and then 1.0 ul of RNase ONE Ribonuclease enzyme (Promega) was added. The strip tube was capped and incubated at 37° C. for about one hour.

TABLE 11

| tube # | Dilution buffer | zeolite (g) | zeolite added before or after heat incubation |
|---|---|---|---|
| 1-3 | DB4.36 – EDTA | 0.42 | before |
| 4-6 | DB4.36 – EDTA | 0.42 | after |
| 7-9 | DB4.36 (pH 3.8) | 0.42 | after |
| 10 | DB4.36 + EDTA | 0.40 | before |
| 11 | DB4.36 + EDTA | 0.43 | before |
| 12 | DB4.36 + EDTA | 0.50 | before |
| 13-14 | DB4.36 + EDTA | 0.50 powder | after |

To evaluate the eluates the samples were loaded on a 1% agarose, 1×TBE gel containing ethidium bromide. 10 ul of each elution 1 or elution 2 was added to 2 ul Blue/Orange Loading Dye, 6× (Promega). 2.5 ul Blue/Orange Loading Dye, 6× was added to the RNaseONE-treated samples. Each lambda marker lane had 2 ul of lambda DNA EcoRI/HindIII marker (Promega Cat. #G1731) mixed with 9 ul water and 2 ul Blue/Orange Loading Dye, 6×. Each 100 bp DNA Ladder had 3 ul of 100 bp DNA Ladder (Promega Cat. #G2101) mixed with 7 ul water and 2 ul Blue/Orange Loading Dye, 6×.

The lanes in the top row of FIG. 18 were loaded in the following order (see Table 11 for description): 1. Lambda DNA EcoRI/HindIII marker; 2. 100 bp DNA Ladder; 3. Blank; 4. Sample 1, elution 1; 5. Sample 2, elution 1; 6. Sample 3, elution 1; 7. Sample 4, elution 1; 8. Sample 5, elution 1; 9. Sample 6, elution 1; 10. Sample 7, elution 1; 11. Sample 8, elution 1; 12. Sample 9, elution 1; 13. Sample 10, elution 1; 14. Sample 11, elution 1; 15. Sample 12, elution 1; 16. Sample 13, elution 1; 17. Sample 14, elution 1; 18. Blank 19. Lambda DNA EcoRI/HindIII marker; 20. 100 bp DNA Ladder; 21. Blank; 22. Sample 1, RNase treated; 23. Sample 2, RNase treated; 24. Sample 3, RNase treated; 25. Sample 4, RNase treated; 26. Sample 5, RNase treated; 27. Sample 6, RNase treated; 28 Sample 7, RNase treated; 29. Sample 8, RNase treated; 30. Sample 9, RNase treated; 31. Sample 10, RNase treated; 32. Sample 11, RNase treated; 33. Sample 12, RNase treated; 34. Sample 13, RNase treated; 35. Sample 14, RNase treated; and 36. Lambda DNA EcoRI/HindIII marker.

The lanes in the bottom row of FIG. 18 were loaded in the following order (see Table 11 for description): 1. Lambda DNA EcoRI/HindIII marker; 2. 100 bp DNA Ladder; 3. Blank; 4. Blank; 5. Sample 1, elution 2; 6. Sample 2, elution 2; 7. Sample 3, elution 2; 8. Sample 4, elution 2; 9. Sample 5, elution 2; 10. Sample 6, elution 2; 11. Sample 7, elution 2; 12. Sample 8, elution 2; 13. Sample 9, elution 2; 14. Sample 10, elution 2; 15. Sample 11, elution 2; 16. Sample 12, elution 2; 17. Sample 13, elution 2; 18. Sample 14, elution 2; 19. Blank 20. Lambda DNA EcoRI/HindIII marker; and 21. 100 bp DNA Ladder.

Figure 18:
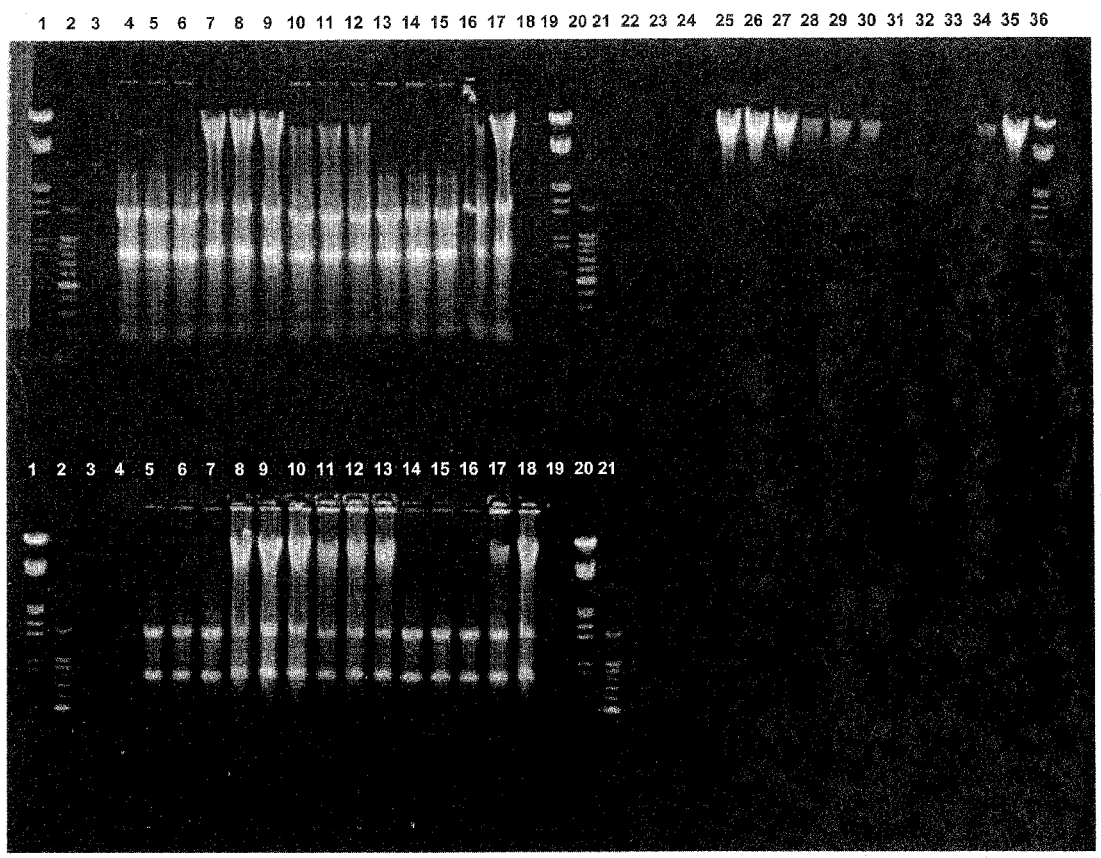
FIG. 18 shows the results of Example 21, which describes the effect of heat on RNA purification with zeolites.

The gel in FIG. 18 shows that when zeolite was added before the heating step there was no visible DNA in the eluate. In contrast, when the zeolite was added after the heat step when samples had cooled for 5 minutes, DNA was visible in the eluate.

Example 22

Heating the Reaction at Different Temperatures

This example describes the use of heat at different temperatures to improve the binding of DNA to zeolites. Frozen bovine spleen tissue was homogenized with 1.0 ml Lysis Solution per 150 mg tissue using a rotor stator homogenizer. The Lysis Solution was SV RNA Lysis Buffer (Promega Cat. #Z3051) with beta-mercaptoethanol added to a final concentration of 1%. The homogenate was divided into tubes and stored at minus 80° C. All the tubes used in this example were polypropylene screw-cap centrifuge tubes.

Tubes containing homogenized bovine spleen were removed from the −80° C. freezer and thawed in water at 4° C. 2 ml aliquots of the bovine spleen homogenate were dispensed into fourteen 15 ml tubes. Four (4.0) ml DB4.36 was added to each of the tubes 1-14. DB4.36 is 3M NaCl, 0.36M $Na_3$ citrate.$2H_2O$, 0.1 mM EDTA (pH 8.0), and 0.0009% Blue dye (FD&C Blue #1) adjusted with concentrated hydrochloric acid to a final pH of 4.0.

To tubes 1-12 was added 1 ml zeolite mixture, which consisted of 2M NaCl, 0.1 mM EDTA (pH 8.0) with zeolite Type 13X added at a concentration of 0.45 g/ml. Tubes 1-12 were inverted 3-4 times and shaken to mix the samples. Tubes 13 and 14 had no zeolite mixture added. Tubes 1-14 were incubated in a water bath for 3 minutes and then returned to a rack at room temperature. The temperature of the water baths were as follows: tubes 1-3 at 10° C., tubes 4-6 at 21° C., tubes 7-9 at 37° C., and tubes 10-12 at 70° C.

For each sample a PUREYIELD Clearing Column (Promega) was inserted in a 50 ml polypropylene catch tube (cap discarded) labeled C1-C14. One at a time, the 15 ml tubes 1-14 were inverted and shaken to mix and then immediately poured into the PUREYIELD Clearing Column in the corresponding labeled tube. These clearing columns in catch tubes were centrifuged at 2000×g for 10 minutes at 22° C. Tubes 13 and 14, without zeolite, did not have all the liquid pass through the clearing column. Four (4) ml isopropyl alcohol was added to the flow through in each tube and inverted 2-4 times to mix. This mixture was poured into a PUREYIELD Binding Column (Promega cat #A245), labeled B1-B14, in a 50 ml tube and spun in a centrifuge at 2000×g at 22° C. for 10 minutes. Tubes 13 and 14 did not have all the liquid pass through the binding column.

Each binding column was transferred to a fresh 50 ml tube. 20 ml SV RNA Wash Solution (Promega Cat #Z3091) was added to the each binding column and centrifuged at 2,000×g for 5 minutes. The flow through was discarded. Then 10 ml SV RNA Wash Solution was added to the binding column and centrifuged at 2,000×g for 10 minutes. The flow through was discarded. Each binding column was transferred to clean 50 ml tubes.

To elute the RNA, 1 ml of nuclease-free water was applied to the binding membrane and incubated at 22° C. for 2 minutes. The columns were centrifuged at 2000×g for 3 minutes (RNA elution 1). Each column was transferred to a fresh 50 ml tube and the elution with 1 ml nuclease-free water was repeated (RNA elution 2).

For ribonuclease digestion, 10 ul of each of the RNA elution 1 samples listed above was added to 1.2 ul of RNase ONE 10× Buffer (Promega Part #217A) in a PCR strip tube and then 2.0 ul of RNase ONE Ribonuclease enzyme (Promega part #M4261) was added. The strip tube was capped and incubated at 37° C. for about an hour.

To evaluate the eluates the samples were loaded on a 1% agarose, 1×TBE gel containing ethidium bromide. 10 ul of each elution 1 or elution 2 was added to 2 ul Blue/Orange Loading Dye, 6× (Promega). 2.5 ul Blue/Orange Loading Dye, 6× was added to the RNaseONE-treated samples. Each lambda marker lane had 2 ul of lambda DNA EcoRI/HindIII marker (Promega cat #G1731) mixed with 9 ul water and 2 ul Blue/Orange Loading Dye, 6×. Each 100 bp DNA Ladder had 3 ul of 100 bp DNA Ladder (Promega cat #G2101) mixed with 7 ul water and 2 ul Blue/Orange Loading Dye, 6×.

Figure 19:
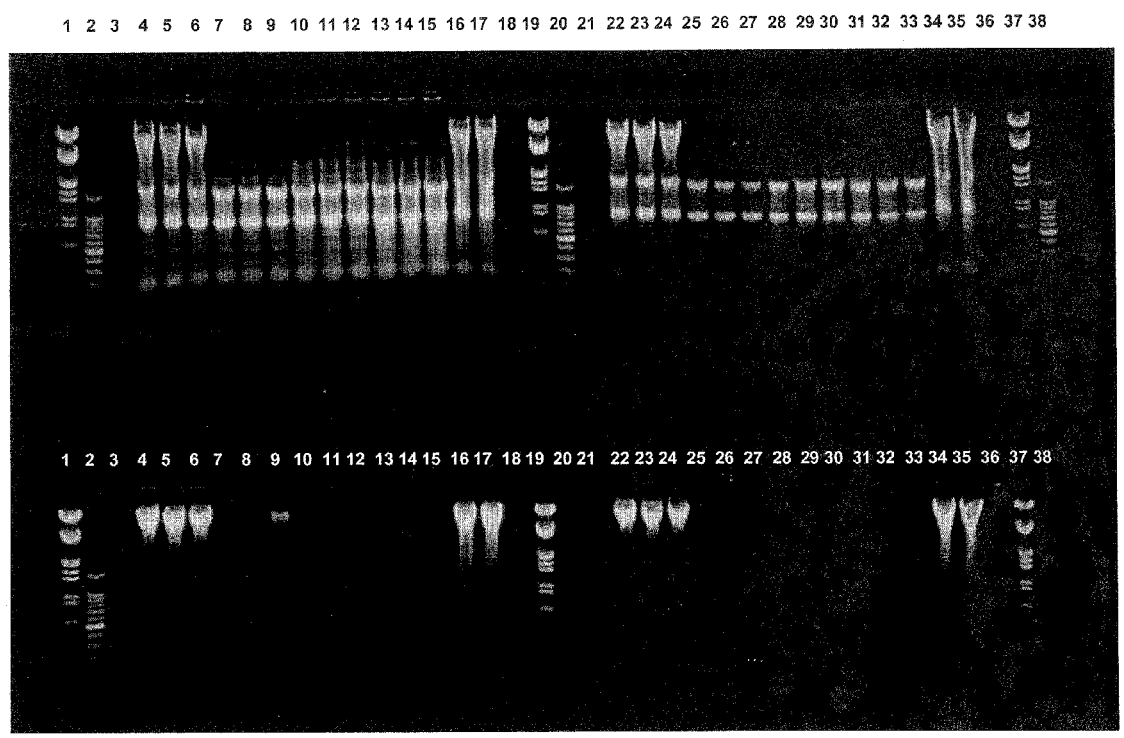
FIG. 19 shows the results of Example 22, which describes the use of heat at different temperatures to improve the binding of DNA to zeolites.

In FIG. 19 the top row and bottom rows in the gel were loaded in the same order as listed below, except where noted. The bottom row samples were treated with RNaseONE™. The lanes were as follows: 1. Lambda DNA EcoRI/HindIII marker; 2. 100 bp DNA Ladder; 3. Blank; 4. Sample 1, 10° C., elution 1; 5. Sample 2, 10° C., elution 1; 6. Sample 3, 10° C., elution 1; 7. Sample 4, 21° C., elution 1; 8. Sample 5, 21° C., elution 1; 9. Sample 6, 21° C., elution 1; 10. Sample 7, 37° C., elution 1; 11. Sample 8, 37° C., elution 1; 12. Sample 9, 37° C., elution 1; 13. Sample 10, 70° C., elution 1; 14. Sample 11, 70° C., elution 1; 15. Sample 12, 70° C., elution 1; 16. Sample 13, no zeolite, elution 1; 17. Sample 14, no zeolite, elution 1; 18. Blank; 19. Lambda DNA EcoRI/HindIII marker; 20. Top: 100 bp DNA Ladder; 20. Bottom: Blank; 21. Blank; 22. Sample 1, 10° C., elution 2; 23. Sample 2, 10° C., elution 2; 24. Sample 3, 10° C., elution 2; 25. Sample 4, 21° C., elution 2; 26. Sample 5, 21° C., elution 2; 27. Sample 6, 21° C., elution 2; 28. Sample 7, 37° C., elution 2; 29. Sample 8, 37° C., elution 2; 30. Sample 9, 37° C., elution 2; 31. Sample 10, 70° C., elution 2; 32. Sample 11, 70° C., elution 2; 33. Sample 12, 70° C., elution 2; 34. Sample 13, no zeolite, elution 2; 35. Sample 14, no zeolite, elution 2; 36. Blank; 37. Lambda DNA EcoRI/HindIII marker; 38. Top: 100 bp DNA Ladder; and 38. Bottom: Blank.

The gel in FIG. 19 showed the most DNA present in samples 13 and 14 (lanes 16 and 17) which did not have zeolite. There was also an intense DNA band in elution 1 and elution 2 of samples 1-3 (lanes 4-6 and 22-24) with the "heat" incubation at 10° C. When the heat incubation was 21° C., DNA was visible on the gel in elution 1 of sample 6 (lane 9) but not elution 2 (lane 27), and not in either elution of samples 4 or 5 (lanes 7, 8, 25, and 26). The DNA band was much less intense in sample 6 elution 1 than the 10° C. incubation eluates or the "no zeolite" eluates. No DNA was visible in the elutions of samples heated at 37° C. or 70° C. (lanes 10-15 and 28-33). These results showed that at room temperature zeolite bound DNA and that increasing the temperature generally improved the amount of DNA bound, and therefore removal of DNA from the final purified RNA improved.

Example 23

Zeolite 13X Binding of Oligonucleotides, and Elution There From

This example describes the binding of zeolite 13X to a mixture of double stranded 35 bp DNA, single stranded 35 base DNA, single stranded 30 base DNA, 25 bp double stranded RNA, 25 base single stranded RNA and 21 base single stranded RNA, and elutions of the bound oligonucleotides. The nucleic acid bound to the zeolite particles was separated from the remaining aqueous phase by placing the zeolite particles in a Corning 0.22µ nylon membrane Spin-X column, followed by centrifugal separation.

The mixture of RNA and DNA oligonucleotides (all $T_m$ values below were calculated for 50 mM NaCl) was made by combining the following:

(21 bases, SEQ ID NO: 1)
$RNA_1$ = 5'-UAUUGCACUUGUCCCGGCCUG-3' $T_m$ 46° C.

(25 bases, SEQ ID NO: 2)
$RNA_2$ = 5'-GAGACCCAGUAGCCAGAUGUAGCUU-3' $T_m$ 61° C.;

(SEQ ID NO: 3)
$RNA_{2-COMPL}$ ("$RNA_2$.") = 5'-AAGCUACAUCUGGCUACUGGGUCUC-3' 25 b $T_m$ 62° C.;

(35 bp, SEQ ID NO: 4)
$DNA_A$ = 5'-AGCTGTCTAGGTGACACGCTAGAGTACTCGAGCTA-3' $T_m$ 65° C.;

(SEQ ID NO: 5)
$DNA_{A'-COMPL}$ = 5'-TAGCTCGAGTACTCTAGCGTGTCACCTAGACAGCT-3' $T_m$ 65° C.;

(30 bases, SEQ ID NO: 6)
$DNA_B$ = 5'-GTTACACATGCCTACACGCTCCATCATAGG-3' $T_m$ 62° C.

There was an excess of either one of the complementary sequences (for example $RNA_2$ and its complementary sequence, denoted as "$RNA_{2-COMPL}$" or "$RNA_2$.") or the other oligonucleotide, so that one of the single stranded RNA (25 base), or DNA (35 base) oligonucleotides was present in the mixture, in addition to the double stranded DNA or double stranded RNA which consisted of the two hybridized complementary sequences.

The initial binding mixture was composed of: 24 ul of the oligonucleotide mix (above), added to 60 ul Lysis Buffer (Promega RNA Lysis Buffer, including 1% beta mercaptoethanol), which was then added to 120 ul of Dilution Buffer (Promega RNA Dilution Buffer). All the tubes used in this example were autoclaved 1.5 ml polypropylene micro-centrifuge tubes. 17 ul aliquots of the above mixture were dispensed into tubes, in triplicate, for each temperature tested. Duplicate samples of "plus zeolite at 21° C." and duplicate samples of "plus zeolite at 38° C." were run. Single control samples were run without added zeolite for both 21° C. and 38° C. (control solutions were incubated and centrifuged through nylon membranes under identical conditions with the "plus zeolite" samples). For the "plus zeolite" tubes, 2.5 ul of zeolite solution (47% wt/vol of 13X zeolite in 2M NaCl, 0.1 mM EDTA) was added to each of the tubes with the oligonucleotide mixture. All samples were mixed and held at 21° C. for 5 minutes, then two "plus zeolite" and one "no zeolite added" control tube were incubated at 38° C. (note that this is well below the $T_m$ for the above mixture components) for 15 minutes. The remaining three samples were incubated at 21° C. for 15 minutes. Then the samples were transferred to Corning nylon 0.22µ columns, and centrifuged at 11,000×g for 30 seconds. Columns were transferred to fresh tubes. The zeolite particles were then washed in 19 ul of a Lysis/Dilution mixture [composed of 100 ul Lysis Buffer, combined with 200 ul Dilution Buffer] as a method of washing the zeolite particles and nylon membrane. The separation process was repeated and the columns placed in fresh tubes. The zeolite particles were then eluted in 19 ul of nuclease free water for 5 minutes at 21° C. The separation process was repeated and the columns placed in fresh tubes. The elution process was repeated a second time. The zeolite particles were then resuspended in 39 ul of nuclease free water for 5 minutes at 21° C. The resulting solutions (including zeolite particles in elution 3) were removed from the column, and placed in fresh tubes. The samples were run on 15% acrylamide gels, and the samples stored at −20° C.

For each of the above tubes, 5 ul was removed and loaded per lane onto a 15% acrylamide formamide gel, and separated by electrophoresis, except that 10 ul was used in the final elution of the zeolite particles (as 39 ul elutions were performed in the third elution, compared to 19 ul for elutions 1 and 2). The elution samples required about 2 hours at 80 volts in TBE buffer and the flowthrough samples containing Lysis Buffer and Dilution Buffer required about 7 hours at 40 volts in TBE buffer (due to the significant salt effects on the separation).

The resulting gel scans shown in FIGS. 20A and 20C demonstrated that both double stranded DNA (top band, 35 base pairs) and single stranded DNA (third band down, 35 bases) were bound to zeolite 13X at both 21° C. and 38° C. In contrast, FIGS. 20A and 20C also showed that both double stranded RNA (second band down, 25 base pairs) and single stranded RNA (25 bases and 21 bases) have much lower binding to zeolite at both 21° C. and 38° C. compared to the binding of DNA. The bound double stranded DNA and single stranded DNA was shown to elute in FIGS. 20B and 20C. While some double stranded RNA was eluted from the zeolite, this was much less than the amount of double stranded RNA that did not bind to the zeolite in the flowthrough.

It was also noted that the "no zeolite" samples showed some binding of RNA, which may have been due to the nylon membrane that was used in the separation process. Similarly the first and second elutions of the "no zeolite" samples showed some RNA being eluted, which may have been due to the nylon membrane used in the column separation. This suggests that the double stranded RNA seen in the "+ zeolite" samples may largely be due to binding to the nylon membrane, rather than to binding to the zeolite. Moreover, the "+ zeolite" samples shown in elution 3 of FIGS. 20B and 20D did not show visible eluted RNA, which suggests that the RNA seen to elute in the first and second elutions was likely due to its binding to the nylon membrane. Once the zeolite was separated from the nylon membrane in the third elution, no RNA was shown to elute from the zeolite. In contrast, both double stranded DNA and single stranded DNA were eluted in the third elution from the zeolite when it was separated from the nylon membrane (FIGS. 20B and 20D).

Comparing both the binding (FIGS. 20A and 20C) and elutions (FIGS. 20B and 20D), it was apparent that the heating of samples from 21° C. to 38° C. increased the binding of double stranded DNA to the zeolite. Comparing the flowthrough bands of 21° C. (FIG. 20A) to those of 38° C. (FIG. 20C), double stranded DNA was more completely bound to the zeolite at 38° C. The amount of double stranded RNA remaining unbound was relatively similar between 21° C. and 38° C., which is consistent with the idea that the observed background binding of RNA to the nylon membrane was not affected much by the increased temperature.

Example 24

Zeolite Binding of Genomic DNA and Oligonucleotides, and Elution Therefrom

This example describes the binding of zeolite to a mixture of: genomic DNA (Promega catalog #G304A, 90% of which is 50,000 base pairs (bp) or larger), double stranded 35 bp DNA, single stranded 35 base DNA, single stranded 30 base DNA, 25 bp double stranded RNA, 25 base single stranded RNA and 20 base single stranded RNA. The nucleic acid bound to the zeolite particles was separated from the remaining aqueous phase by either (A) forming a zeolite pellet by centrifugation, or (B) placing the zeolite particles in a Corning 0.22µ nylon membrane Spin-X column (Corning catalog #8169, Corning, N.Y.) followed by centrifugal separation, or (C) magnetic separation of zeolite coated $Fe_3O_4$ particles.

The mixture of RNA and DNA oligonucleotides was made by combining the following:

```
                              (20 bases, SEQ ID NO: 7)
RNA₁ = 5'-AGACCCAGUAGCCAGAUGUA-3' T_m 56° C.

(25 bases, SEQ ID NO: 2)
RNA₂ = 5'-GAGACCCAGUAGCCAGAUGUAGCUU-3' T_m 61° C.;

(SEQ ID NO: 3)
RNA₂-COMPL = 5'-AAGCUACAUCUGGCUACUGGGUCUC-3';
T_m 62° C.

(35 bp, SEQ ID NO: 4)
DNA_A = 5'-AGCTGTCTAGGTGACACGCTAGAGTACTCGAGCTA-3';
T_m 65° C.

(SEQ ID NO: 5)
DNA_A-COMPL = 5'-TAGCTCGAGTACTCTAGCGTGTCACCTAGACAG
CT-3' T_m 65° C.;

(30 bases, SEQ ID NO: 6)
DNA_B = 5'-GTTACACATGCCTACACGCTCCATCATAGG-3'
T_m 62° C.
```

There was an excess of either one of the complementary sequences (-$_{COMPL}$) or the other, so that one of the single stranded RNA (25 base), or DNA (35 base) oligonucleotides was present in the mixture in addition to the double stranded molecules. Hybridization between the $R_1$ 20 base sequence and the complementary $R_2$ 25 base sequence generated molecules that were 20 base pairs with a 5 base single stranded overhang (third band from the top in the oligo ladder). Because it is partly double stranded and partly single stranded, it is listed as "20 bp/5b" (20 bases double stranded and 5 bases single stranded) on the gel scan images although it is referred to here as double stranded for purposes of brevity.

The initial binding mixture was composed of: 24 ul of the oligonucleotide mixture (above) added to 60 ul RNA Lysis Buffer (Promega cat Z3051, including 1% beta mercaptoethanol), which was then added to 120 ul of Dilution Buffer. All the tubes used in this example were autoclaved 1.5 ml polypropylene micro-centrifuge tubes. 17 ul aliquots of the above mixture were dispensed into tubes, in triplicate, for each zeolite condition tested ("pellet", "spin column", and "magnetic particle"). For all but the "initial mix" tubes, 2.5 ul of zeolite solution (47% wt/vol of 13X zeolite in 2M NaCl, 0.1 mM EDTA) for "pellet" and "spin column" and 2.5 ul of 0.1% (wt/vol) $Fe_3O_4$-zeolite 3A made as described in Example 13 was added to each of the tubes with the initial mixture of human genomic DNA plus oligonucleotides. All samples were mixed and held at 21° C. for 5 minutes, then 70° C. for 5 minutes. The "spin column" samples were transferred to Corning nylon 0.22µ columns (above), and centrifuged at 11,000×g for 1 minute, along with the "pellet" sample tubes. The "magnetic zeolite" samples were placed on a magnetic rack and the supernatants removed to clean tubes and stored at −20° C. The pellet supernatants and column flowthroughs were transferred to fresh tubes and stored at −20° C. The zeolite particles were then resuspended in 17 ul of ⅓ Lysis Buffer (above) and ⅔ Dilution Buffer (above). The separation process was repeated and the resulting solutions stored in fresh tubes at −20° C. The zeolite particles were then resuspended in 17 ul of nuclease free water for 5 minutes at 21° C. The separation process was repeated and the resulting solutions stored in fresh tubes at −20° C. The elution process was repeated a second time. The zeolite particles were then resuspended in 30 ul of nuclease free water for 5 minutes at 21° C. The resulting solutions (including zeolite particles) were stored at −20° C.

For each of the above tubes, 5 ul was removed and loaded per lane onto a 14% acrylamide formamide gel, and separated by electrophoresis, except that 30 ul was used in the final elution of the zeolite particles in the nylon 0.2µ column to facilitate resuspension of the zeolite particles, and 10 ul of this elution was loaded per well. The elutions required about 90 minutes at 100 volts in TBE buffer and the samples containing Lysis Buffer and Dilution Buffer (as above) required about 6 hours at 40 volts (due to the significant salt effects on the separation).

Figure 21B:
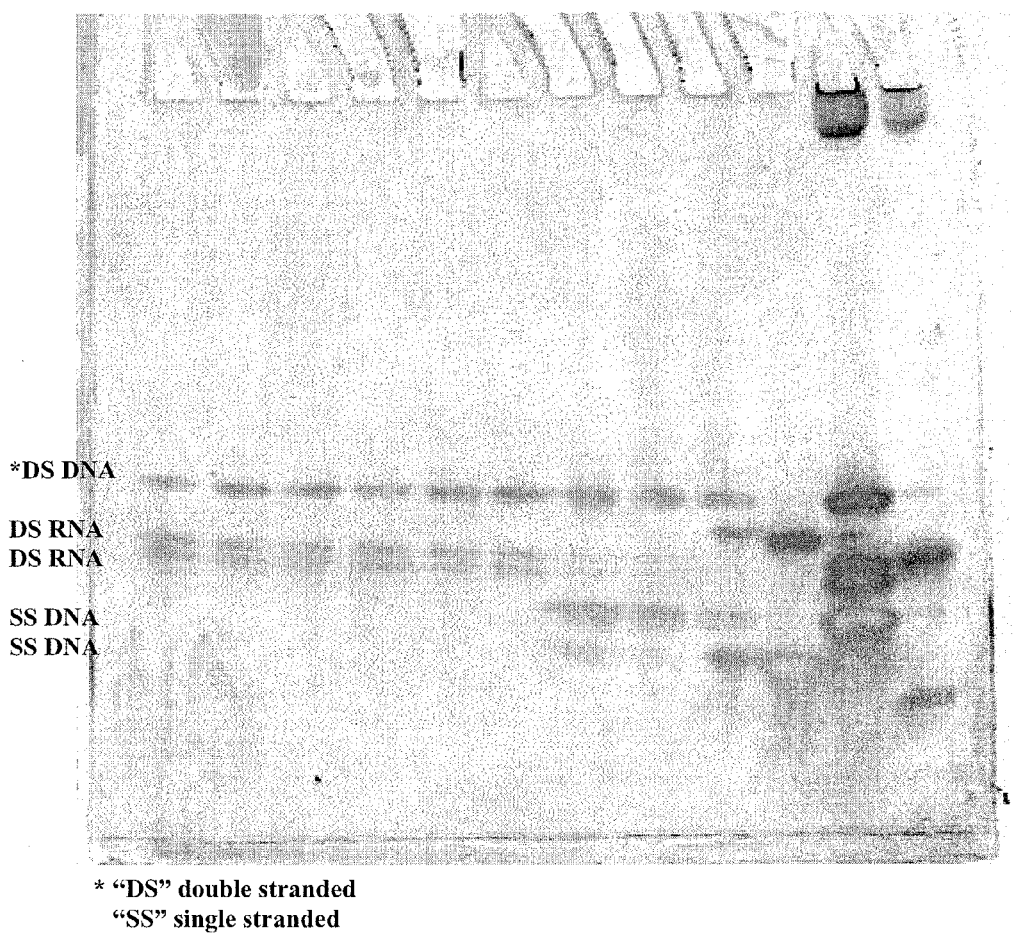
FIG. 21 shows the results of Example 24, which describes the binding of zeolite to a mixture of: genomic DNA double stranded 35 bp DNA, single stranded 35 base DNA, single stranded 30 base DNA, 25 bp double stranded RNA, 25 base single stranded RNA and 20 base single stranded RNA.
Figure 21C:
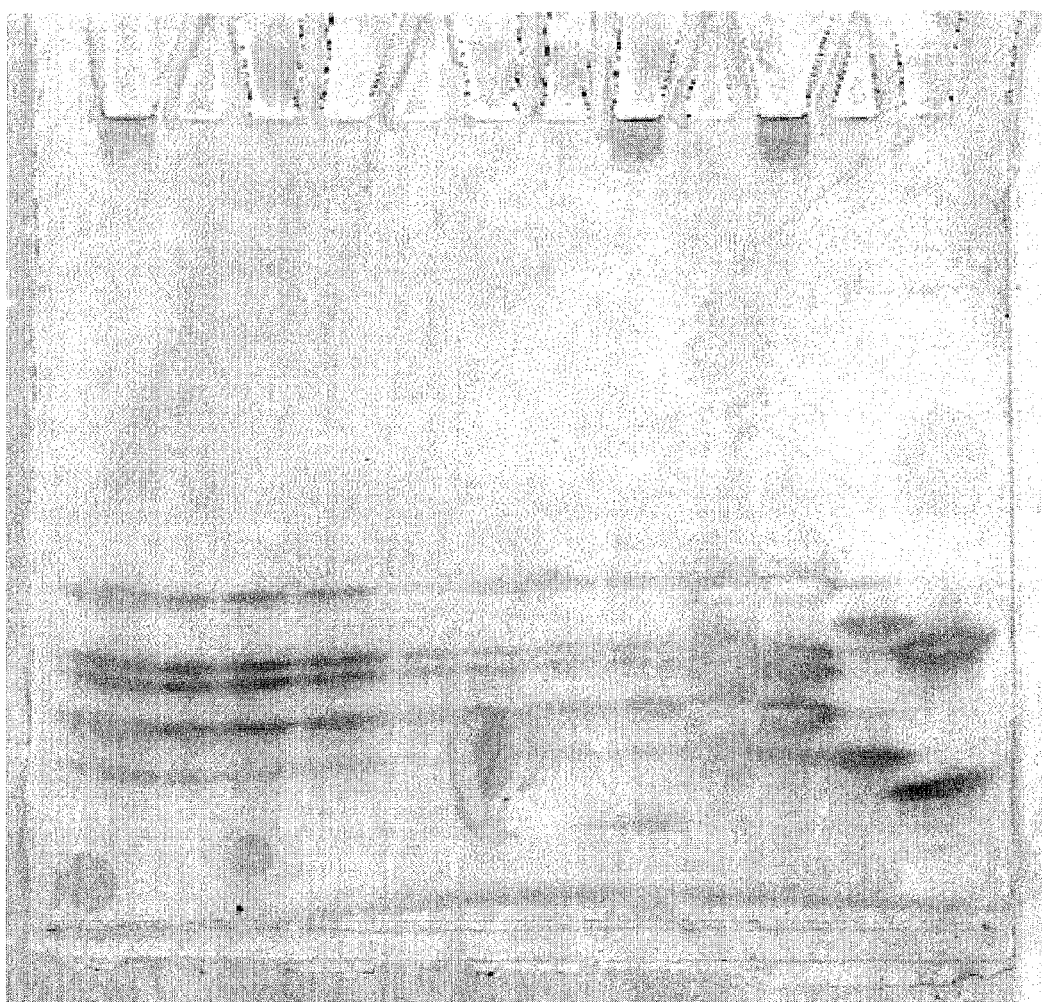
Figure 21D:
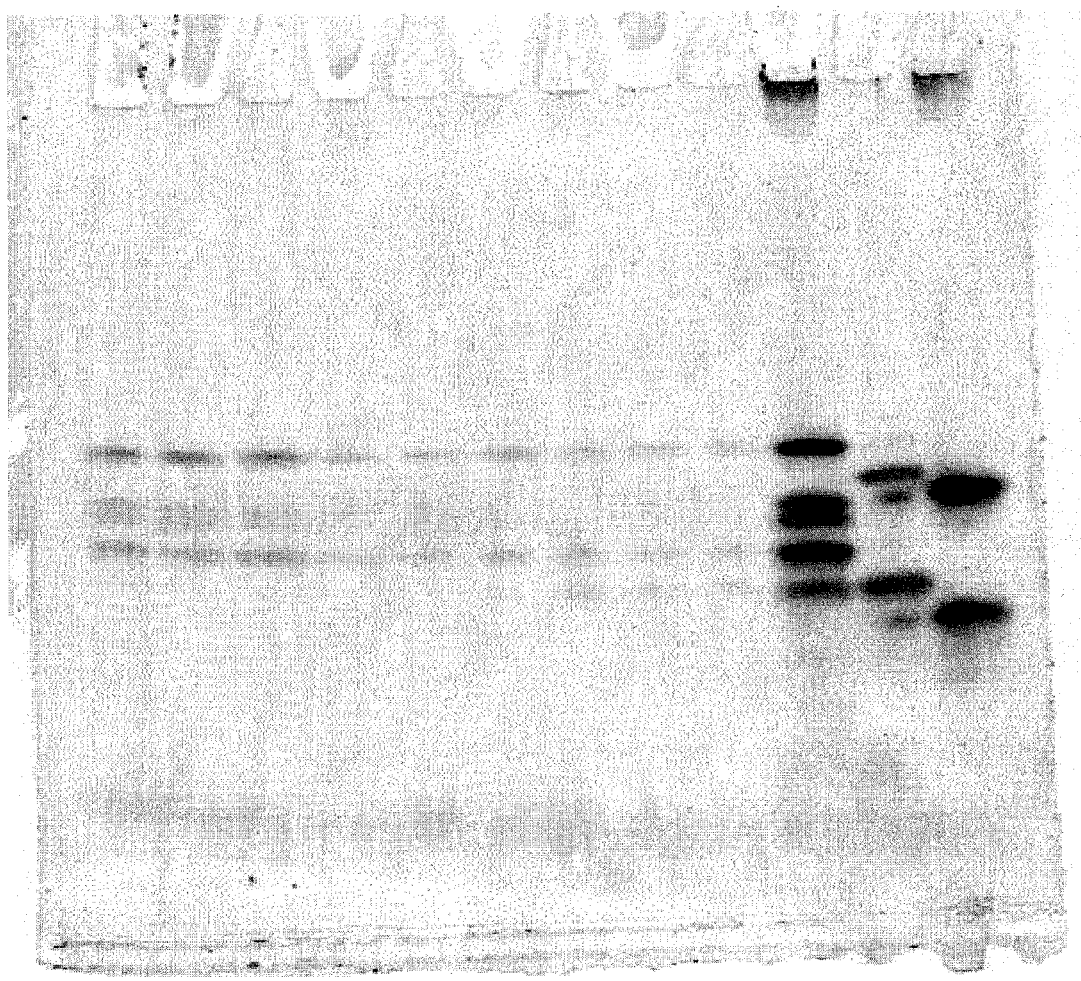

The resulting gel scans shown in FIGS. 21A and 21C have shown that both double stranded (top band) and single stranded DNA (fourth and fifth bands down) bind to zeolite 13X, but the two double stranded RNA bands (second and third from the top) substantially remained unbound. As noted in Example 23, the column based separations (seen in FIG. 21A) have introduced the binding of RNA to the nylon membrane in the column, but this variable is not present in the "pelleted" samples, as shown in FIG. 21C. When looking at the third elutions shown in FIGS. 21B and 21D (lanes 7, 8, and 9 in both gels) the DNA bands (both double stranded and the two single stranded bands) were clearly visible in all 6 samples, but none of the 6 samples showed visible RNA bands (second and third from top). This data has been consistent with the data of Example 23, showing that (a) both double stranded DNA and single stranded DNA are bound to, and eluted from, zeolite 13X, and (b) RNA is not substantially bound to zeolite 13X.

FIGS. 21A through 21D have shown that genomic DNA was bound to zeolite 13X, but has not shown any visible bands in any of the elutions. The elutions showed no visible genomic DNA, even in the third set of elutions where the particles were also included in the sample loaded onto the gel. While not necessary to understand or practice the present invention, one explanation for this may be that the large size of the genomic DNA (90% is 50 kb or larger) would have bound in multiple sites to the zeolite, and thus would have difficulty eluting from the zeolite surface. This property would further enable the separation of RNA from the higher molecular weight genomic DNA found in homogenized tissue lysates.

Figure 21E:
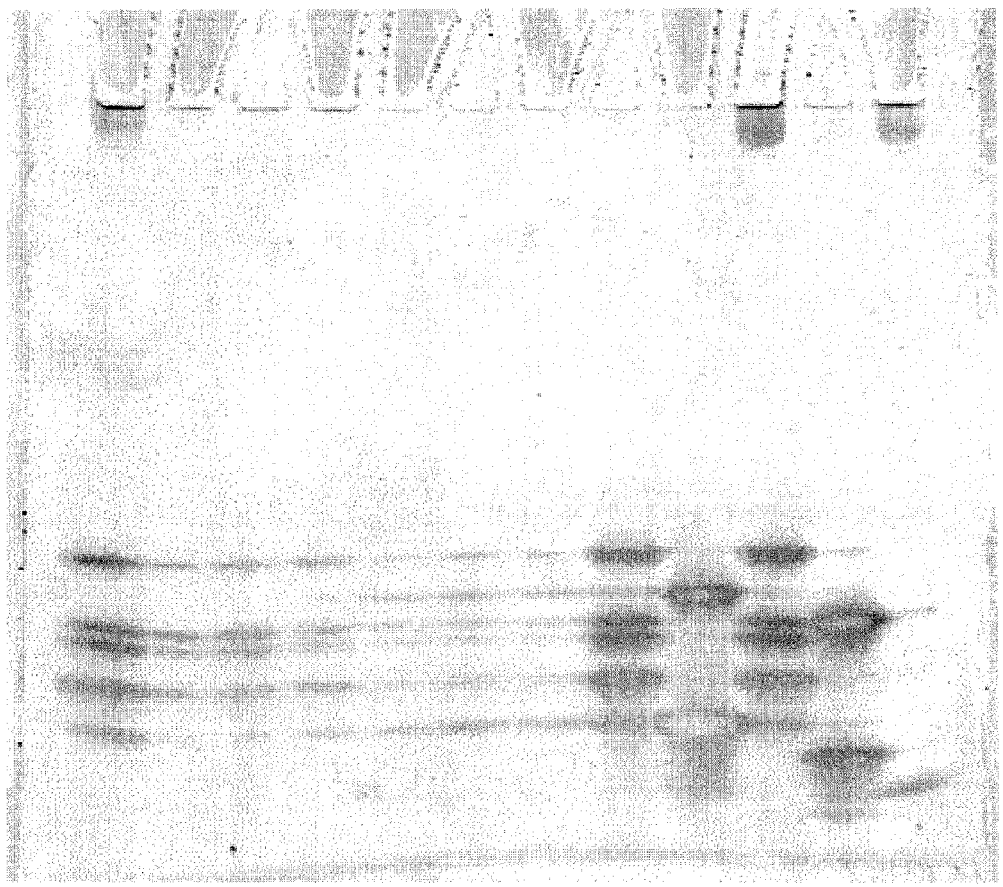
Figure 21F:
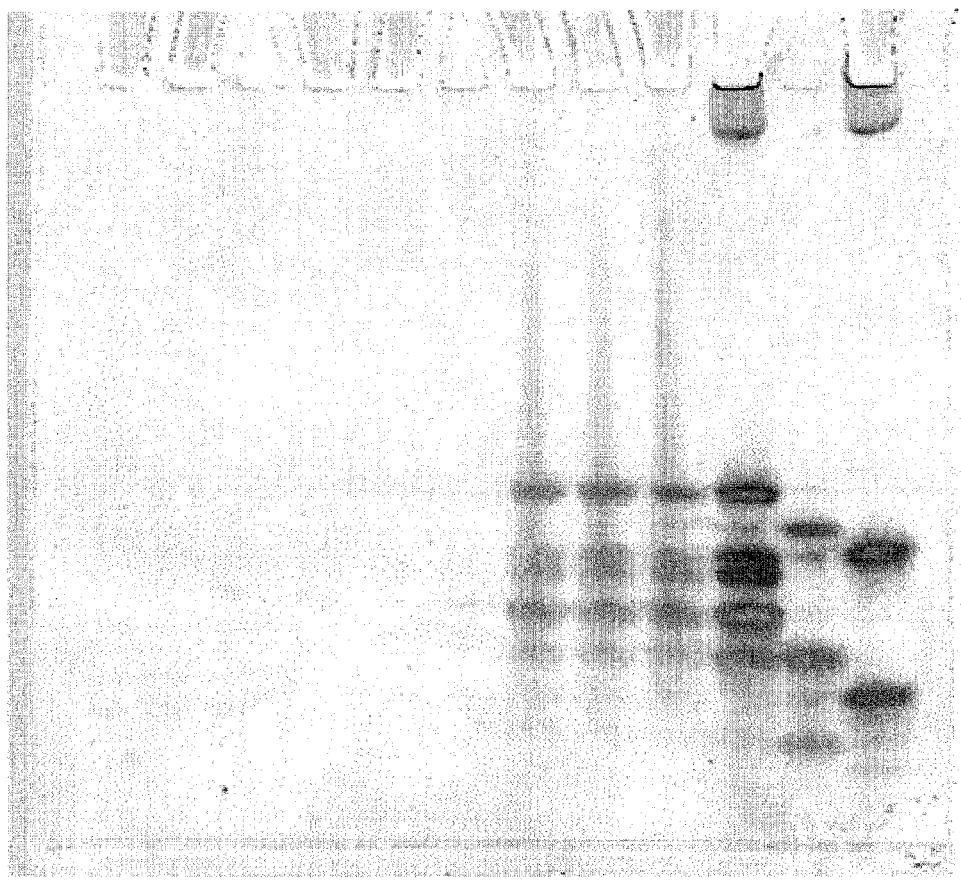

FIGS. 21E and 21F have shown that paramagnetic zeolite 3A particles bind both DNA and RNA, in contrast to the properties of zeolite 13X, noted above.

Example 25

Determination of Genomic DNA and Specific mRNA Content of Total RNA Samples

This example describes the quantitation of genomic DNA contamination in total RNA samples by quantitative PCR (qPCR) and the quantitation of specific mRNAs by quantitative RT-PCR (qRT-PCR). Promega's Plexor™ qPCR System (Cat. #A4011) and Plexor™ One-Step qRT-PCR System (Cat. #A4021) were used. The sensitivity of the Plexor™ technology allowed accurate quantitation of as few as ten copies of a single haploid gene by qPCR. The Plexor™ qPCR reactions were set up on ice as described in the Plexor™ qPCR System Technical Manual (Part #TM262, Promega Corporation, Madison, Wis.). A reaction mix was prepared, composed of 12.5 µl of 2× Plexor™ Master Mix, 1.0 µl of a 25× Plexor™ primer pair mix (5 µM of each primer) and Nuclease-Free Water to a final volume of 20 µl per reaction. The final concentration of each primer in the assay was 200 nM. Twenty µl of reaction mix was distributed to individual wells of a 96-well Optical Reaction Plate (Applied Biosystems, Foster City, Calif.). Five µl of each prepared sample or standard was added to the wells containing reaction mix for a total volume of 25 µl. Each sample and standard was analyzed in triplicate. The optical plate was sealed with an Optical Adhesive Cover. The sealed plate was briefly centrifuged to collect the reactions to the bottom of the wells. Primers that amplified the human thyroid peroxidase (TPOX) short tandem repeat (STR) locus were used for specific quantitation of genomic DNA in the presence of total RNA. The forward primer (5' FAM iso-dC-GTCCTTGTCAGCGTTTATTT; SEQ ID NO:8) was labeled with fluorescein (FAM) and contained a nucleotide analog, methylisocytosine (iso-dC). The reverse primer (5' HO-CCCAGAACCGTCGACTG; SEQ ID NO:9) was unlabelled. Primers were synthesized by EraGen Biosciences (Madison, Wis.) and were diluted in Promega's MOPS/EDTA Buffer (Cat. #Y5101), protected from light. Promega's Human Genomic DNA (Cat. #G3041) standard curve was used for quantitation. Human Genomic DNA was diluted in MOPS/EDTA Buffer to the equivalent of 10,000, 1,000, 100 and 10 haploid genome copies per reaction. The standard curve was based on the assumption that 33 ng of human genomic DNA was equivalent to 10,000 haploid genome copies. That assumption was based on estimates of 6.6 pg of genomic DNA per human diploid cell and a human genome size of 2.9 Gb. The total RNA samples were diluted to 400 ng/µl in Promega's Nuclease-Free Water, based on absorbance at 260 nm. The samples were then diluted to 20 ng/µl in MOPS/EDTA Buffer. One hundred ng of each total RNA sample was analyzed per reaction. The Plexor™ qPCR amplifications were run on an Applied Biosystems 7500 Real-Time PCR System instrument (Applied Biosystems, Foster City, Calif.) as described in the Plexor™ Systems Instrument Setup and Data Analysis for the Applied Biosystems 7300 and 7500 Real-Time PCR Systems Technical Manual (Part #TM265, Promega Corporation, Madison, Wis.). Data analysis was performed using Plexor™ Analysis Software (v.1.1.4, Java VM Version 1.4.2_04-b05, Promega Corporation, Madison, Wis., © EraGen Biosciences, Madison, Wis.).

Figure 22A:
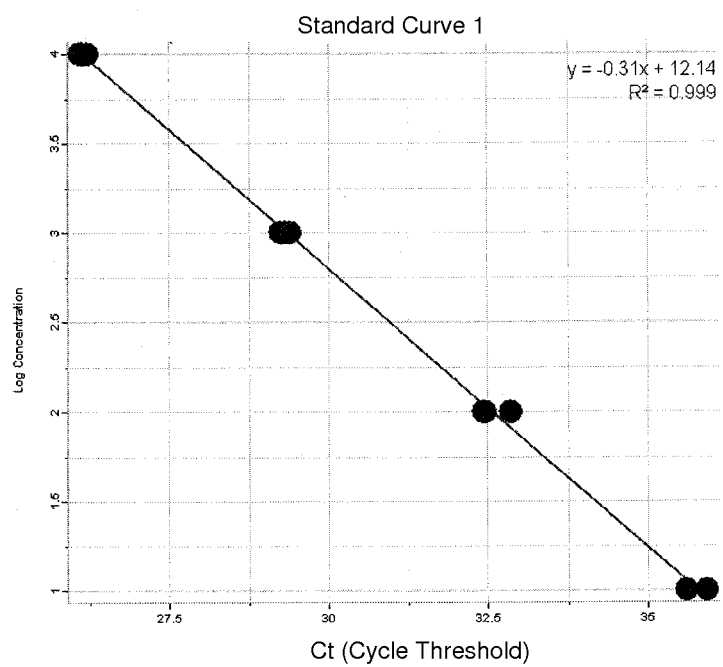
FIG. 22 shows the results of Example 25, which describes the quantitation of genomic DNA contamination in total RNA samples by quantitative PCR (qPCR) and the quantitation of specific mRNAs by quantitative RT-PCR (qRT-PCR).
Figure 22B:
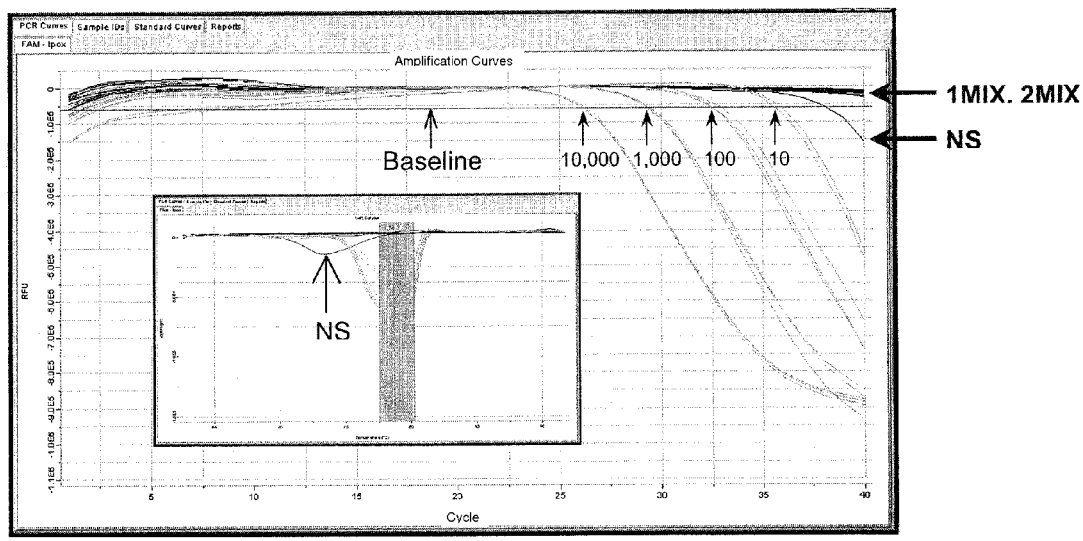

FIG. 22A shows the Plexor™ TPOX qPCR standard curve, generated from a dilution series of Human Genomic DNA. FIG. 22B shows the results of Plexor™ qPCR analysis of the HEK293T 1E8 1MIX and 2MIX total RNA samples that were generated by Example 1. In that example, total RNA was isolated from $1\times10^8$ (1E8) human HEK293T cells per isolation. The 1E8 1MIX 1, 1MIX 2, 2MIX 1 and 2MIX 2 samples (designated "1MIX" and "2MIX" for sample groups) were shown in black and the DNA standards were shown in grey. The genomic DNA amounts were 10,000, 1,000, 100 and 10 haploid genome copies, from left to right across the graph indicated by arrows. The Plexor™ technology was based on quenching of a fluorescent primer during PCR or RT-PCR amplification (e.g., Frackman, S., et al. (2006) Promega Notes 92, 10-13). The initial reactions showed high levels of fluorescence from the fluorescently labeled primer. For the DNA standards, the fluorescent signal decreased proportionally to the amount of template in the reaction. This was due to the specific incorporation of a quencher from the Plexor™ reaction mix, dabcyl-isoguanine (dabcyl-iso-dGTP). The dabcyl quencher was incorporated opposite the iso-dC residue of the labeled primer during amplification, resulting in quenching of the fluorescent signal. As the PCR product accumulated exponentially, the signal decreased proportionally. The early exponential phase was analyzed to provide the most accurate quantitation. The fluorescence of each sample (relative fluorescence units (RFU)) was measured at each PCR cycle by the Real-Time PCR System instrument. A plot of the fluorescence vs. cycle number was generated for each sample. The threshold was calculated, based on the initial background fluorescence. The calculated base line was plotted as a horizontal line, indicated by an arrow in FIG. 22B. When each fluorescent signal decreased below the threshold, the sample was assigned the corresponding cycle threshold ($C_t$) value. A plot of the $C_t$ value vs. the initial template concentration of the Human Genomic DNA standards generated a standard curve that was used to quantitate the unknowns. Higher template amounts produced lower Ct values, due to early quenching. Lower template amounts produced progressively higher $C_t$ values. The absence of a detectable amount of template resulted in a curve with high fluorescence that usually did not cross the threshold, unless non-specific amplification products were generated. "No Template Control" reactions (NTC) were included as a negative control to detect background DNA contamination in the reaction mix. The NTC reactions consisted of 5 µl of MOPS/EDTA Buffer added to 20 µl of reaction mix, in place of template. The NTC reactions displayed high fluorescence with no specific amplification products or $C_t$ values generated (not shown). This indicated that no background DNA was detected. The 1MIX 1, 1MIX 2, 2MIX 1 and 2MIX 2 amplification curves were similar to the NTC amplification curves. They displayed high fluorescence, with no specific amplification products or $C_t$ values. No genomic DNA was detected in the 1MIX or 2MIX samples when 100 ng of total RNA was amplified per reaction. Of note, an outlier occurred in one triplicate reaction and was labeled "NS" for non-specific amplification. This was based on the lower $T_m$, as described below.

Quenching of the fluorescently labeled PCR products was reversible by heat denaturation. The Plexor™ technology included an optional thermal melt curve to determine the melting temperature of the PCR products. As the completed reactions were heated and then cooled, following amplification, the fluorescent signals peaked at the melting temperature ($T_m$). This was due to denaturation, followed by reannealing, of the two DNA strands. As the two strands separated, the fluorescence increased, due to the quencher no longer being adjacent to the fluorescent label. This property reversed when the strands cooled and reannealed. Determining the $T_m$ ensured that changes in fluorescence were due to specific amplification, rather than the production of primer dimers or non-specific amplification products. Specific amplification was indicated by a peak of fluorescence, with a clearly defined $T_m$. Melting curves that showed broadening, multiple peaks or peaks with an altered $T_m$ indicated non-specific amplification products were present (Frackman, S., et al. (2006) Promega Notes 92, 10-13). This resulted from differences in the length and GC content of the non-specific products. The melting curves for the Plexor™ qPCR reactions were shown as an inset to FIG. 22B.

Figure 22C:
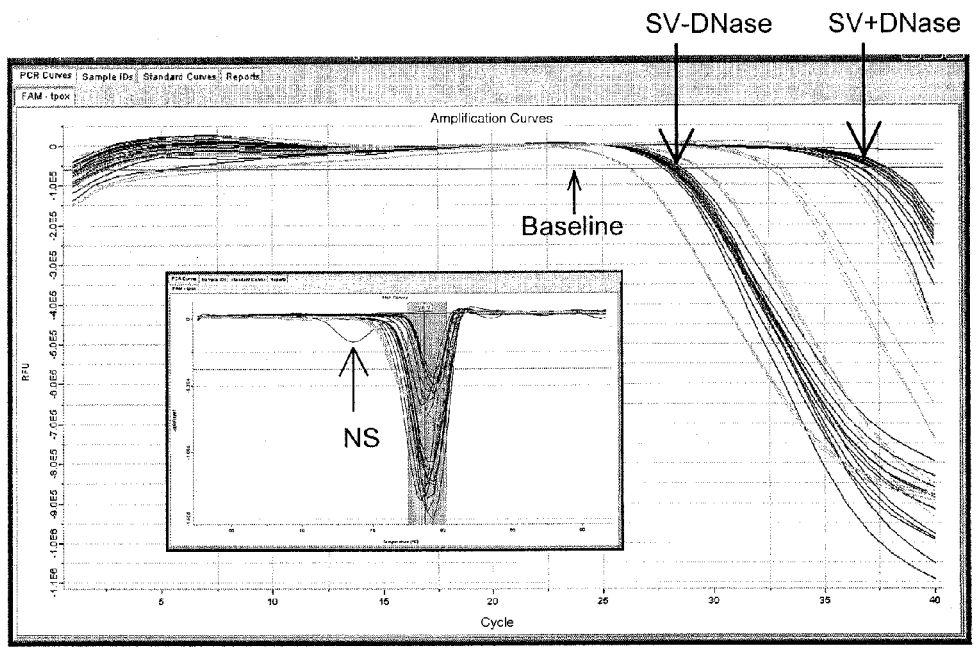

FIG. 22C shows a comparative analysis of total RNA samples isolated using Promega's SV Total RNA Isolation System (Cat. #Z3100). These samples were analyzed in the same experiment as the samples in FIG. 22B. They were shown as a separate figure, in order to distinguish between the samples sets without the use of color. The same standard curve and NTC samples were used for both figures. Total RNA was isolated from $5 \times 10^6$ human HEK293T cells per isolation, with or without DNase treatment (n=4 each). The samples were prepared as in FIG. 22B for qPCR. The same standard curve and NTC samples were used. The SV+/− DNase samples were shown in black and the DNA standards were shown in grey. The genomic DNA amounts were 10,000, 1,000, 100 and 10 haploid genome copies, from left to right across the graph as in FIG. 22B. The standard protocol in the SV Total RNA Isolation System Technical Manual (Promega Corporation, Madison, Wis.) included an on-membrane DNase digestion that removed genomic DNA during the purification process. These samples, designated "SV+ DNase," produced specific amplification products with high $C_t$ values, indicating residual genomic DNA contamination. The SV+DNase values fell below the 10 copy DNA standards, indicating less than 10 copies of genomic DNA contamination per 100 ng of total RNA. Note that one of the triplicate reactions did not give a Ct value and is visible as a line above the threshold. The "SV−DNase" samples were purified without DNase treatment. They gave significantly lower Ct values, indicating higher levels of genomic DNA contamination. The melting curves were shown as an inset. The results showed a clear effect of DNase treatment on the amount of genomic DNA contamination. The integrated DNase treatment dramatically reduced genomic DNA contamination in the SV+DNase samples, compared to the SV−DNase samples. Without DNase treatment, genomic DNA co-purified with the total RNA. The results in FIG. 22C demonstrated that DNase treatment was not completely effective at removing all of the genomic DNA from the samples. In contrast, the 1MIX and 2MIX total RNA samples, purified using Molecular Sieves, type 13X (zeolite) and an acidic dilution buffer, showed complete removal of genomic DNA in FIG. 22B. The results were summarized in Table 12.

| Sample ID | # HEK293T Cells per Total RNA Isolation | Average Genomic DNA Contamination per 100 ng Total RNA (# TPOX Copies) | Standard Deviation |
|---|---|---|---|
| 1E8 1MIX 1 | $1 \times 10^8$ | 0 | NA |
| 1E8 1MIX 2 | $1 \times 10^8$ | 0 | NA |
| 1E8 2MIX 1 | $1 \times 10^8$ | 0 | NA |
| 1E8 2MIX 2 | $1 \times 10^8$ | 0 | NA |
| SV + DNase 1 | $5 \times 10^6$ | 2.9 | 1.0 |
| SV + DNase 2 | $5 \times 10^6$ | 3.4 | 0.5 |
| SV + DNase 3 | $5 \times 10^6$ | 4.5 | 2.9 |
| SV + DNase 4 | $5 \times 10^6$ | 7.0 | 2.3 |
| SV − DNase 1 | $5 \times 10^6$ | 2,362.6 | 96.6 |
| SV − DNase 2 | $5 \times 10^6$ | 2,805.8 | 359.9 |
| SV − DNase 3 | $5 \times 10^6$ | 1,911.9 | 205.4 |
| SV − DNase 4 | $5 \times 10^6$ | 2,542.6 | 215.2 |
| 1MIX/2MIX Samples | $1 \times 10^8$ | 0 | NA |
| SV + DNase Samples | $5 \times 10^6$ | 4.6 | 2.4 |
| SV − DNase Samples | $5 \times 10^6$ | 2,405.7 | 396.4 |

NA = not applicable

Figure 22D:
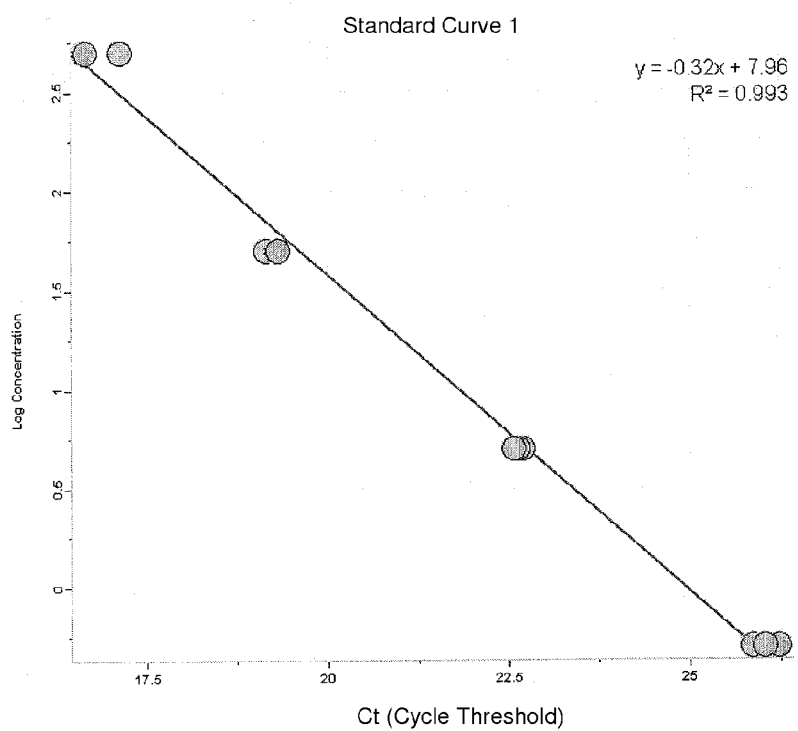
Figure 22E:
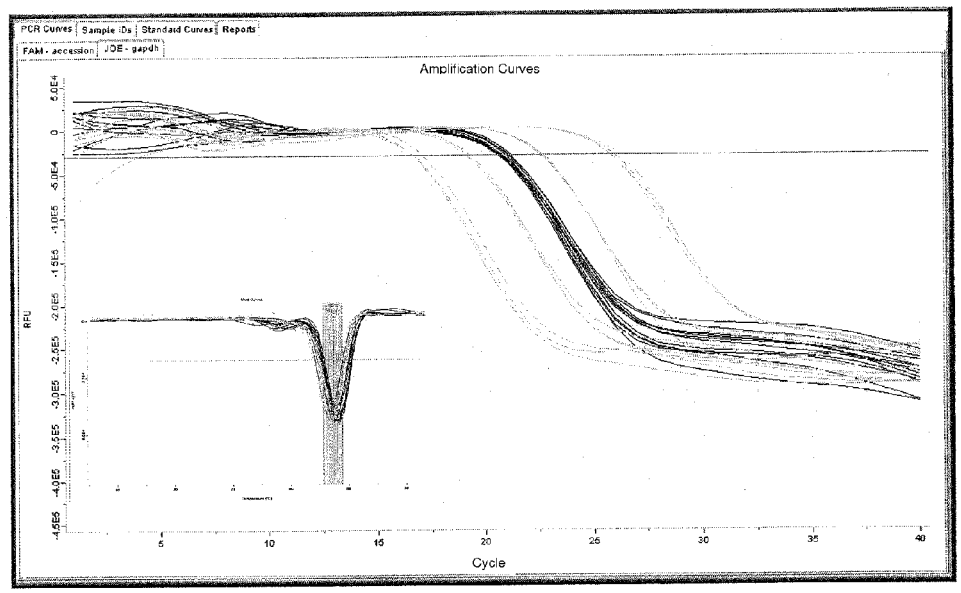
Figure 22F:
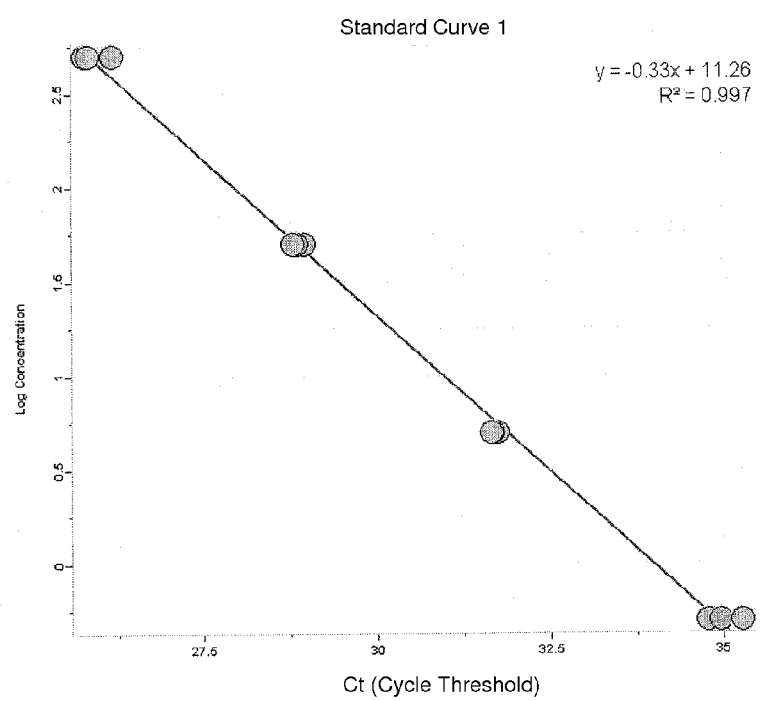
Figure 22G:
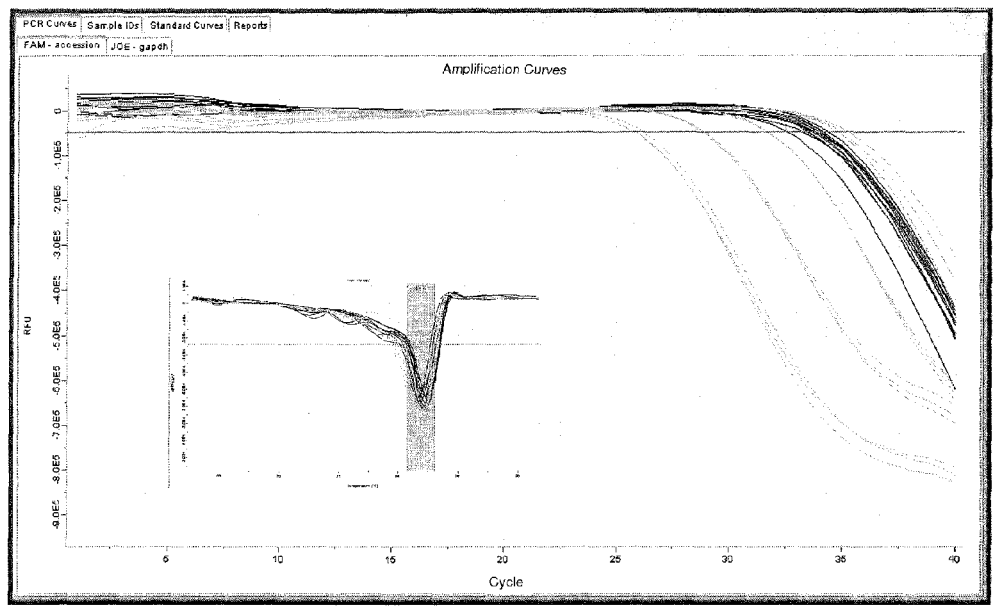

FIGS. 22D through 22G show the results of qRT-PCR using the 1E8 1MIX and 2MIX samples. The Plexor™ One-Step qRT-PCR System was used to quantitate GAPDH (glyceraldehyde-3-phosphate-dehydrogenase) and EDNRB (endothelin receptor type B) mRNAs in 100 ng of total RNA. The total RNA samples were prepared in FIG. 22B. The Plexor™ qRT-PCR amplifications were multiplexed and set up on ice as described in the Plexor™ One-Step qRT-PCR System Technical Manual (Promega Corporation, Madison, Wis.). Two different fluorophores were used. The GAPDH reactions were labeled with JOE and the EDNRB reactions were labeled with FAM. The GAPDH primer sequences were: 5' JOE-iso-dC-AGCCGAGCCACATCG (primer 1, JOE-labeled; SEQ ID NO:10) and 5' HO-GACCAGGCGC-CCAATAC (primer 2, unlabeled; SEQ ID NO:11). The EDNRB primer sequences were: 5' FAM-iso-dC-TC-CCAATATCTTGATCGCCAGCT (primer 1, FAM-labeled; SEQ ID NO:12) and 5' HO-TCTCAGCTCCAAATGGC-CAGT (primer 2, unlabeled SEQ ID NO:13). Primers were synthesized by EraGen Biosciences (Madison, Wis.) and were diluted in MOPS/EDTA Buffer, protected from light. A reaction mix was prepared, composed of 12.5 µl of 2× Plexor™ Master Mix, 0.5 µl of RNasin® Plus RNase Inhibitor, 1.0 µl of a 25× Plexor™ primer pair mix (5 µM of each primer), 0.0625 µl of ImProm-II™ Reverse Transcriptase and Nuclease-Free Water to a final volume of 20 µl per reaction. The final concentration of each primer in the assay was 100 nM for GAPDH and 200 nM for EDNRB. Twenty µl of reaction mix was distributed to individual wells of a 96-well Optical Reaction Plate (Applied Biosystems, Foster City, Calif.). Five µl of each prepared sample or standard was added to the wells containing reaction mix for a total volume of 25 µl. Each sample and standard was analyzed in triplicate. The optical plate was sealed with an Optical Adhesive Cover. The sealed plate was briefly centrifuged to collect the reactions to the bottom of the wells. Each sample and standard was analyzed in triplicate. For the standard curves, a Universal Human Reference RNA (Stratagene Corporation, La Jolla, Calif.), composed of total RNA from 10 different cell lines, was used. The standards were diluted in cold MOPS/EDTA Buffer to generate a dilution series, containing the equivalent of 500 ng, 50 ng, 5 ng and 0.5 ng of total RNA standard. The Plexor™ qRT-PCR amplifications were run on an Applied Biosystems 7500 Real-Time PCR System instrument as described in the Plexor™ Systems Instrument Setup and Data Analysis for the Applied Biosystems 7300 and 7500 Real- Time PCR Systems Technical Manual (Promega Corporation, Madison, Wis.). Reactions were prepared in a 96-well Optical Reaction Plate with Barcode, sealed with an Optical Adhesive Cover. Data analysis was performed using Plexor™ Analysis Software (v.1.1.4, Java VM Version 1.4.2_04-b05, Promega Corporation, Madison, Wis., © EraGen Biosciences, Madison, Wis.). FIGS. 22D and 22E show the GAPDH qRT-PCR standard curve and amplification curves, respectively. FIGS. 22F and 22G show the EDNRB qRT-PCR standard curve and amplification curves, respectively. The 1MIX and 2MIX samples were shown in black and the total RNA standards were shown in grey. The RNA standard amounts were 500 ng, 50 ng, 5 ng and 0.5 ng of total RNA standard, from left to right across the graph. The calculated baseline was plotted as a horizontal line as above. "No Template Control" reactions (NTC) were also run (not shown). The NTC samples showed slight non-specific amplification around cycle 39 (JOE-GAPDH) and cycles 37-39 (FAM-EDNRB), based on their lower Tm's. The insets in FIGS. 22E and 22G showed the melting curves. The results demonstrated that the 1MIX and 2MIX total RNA samples contained specific, quantifiable mRNAs that were reproducible between separately isolated samples.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry and molecular biology or related fields are intended to be within the scope of the following claims.

What is claimed:

1. A method of generating a purified RNA and purified DNA sample from an initial sample that comprises DNA and RNA molecules, said method comprising;
   a) contacting said initial sample with; i) a dilution buffer with an acidic pH, and ii) a nucleic acid binding matrix, which comprises a zeolite, that preferentially binds both single and double stranded DNA molecules in the presence of said dilution buffer, wherein said contacting generates a DNA-bound binding matrix which is substantially RNA free; and
   b) physically separating said DNA-bound binding matrix from said initial sample the remaining initial sample now being a purified RNA sample comprising a plurality of RNA molecules;
   c) contacting the DNA-bound binding matrix with an elution buffer; and
   d) eluting DNA bound to the DNA-bound binding matrix thereby generating a purified DNA sample comprising a plurality of DNA molecules.

2. The method of claim 1, wherein said binding matrix is configured to not bind double stranded or single stranded RNA molecules.

3. The method of claim 1, wherein said initial sample comprises a cell lysate, wherein said cell lysate comprises lysed cells, and wherein said plurality of eluted RNA molecules are present in said purified RNA preparation at a level of at least 5 µg of RNA per 1 million of said lysed cells present in said sample.

4. The method of claim 1, wherein said purified RNA sample is substantially DNA-free.

5. The method of claim 1, wherein said purified DNA is substantially RNA-free.

6. The method of claim 1, wherein said separating comprises centrifuging said initial sample such that a pellet forms which contains said DNA-bound binding matrix, and separating said pellet from the remainder of said initial sample.

7. The method of claim 1, wherein said binding matrix further comprises $Fe_3O_4$ and said separating comprises magnetic separation of said DNA-bound binding matrix from said initial sample.

8. The method of claim 1, wherein said eluting comprises centrifuging said DNA-bound binding matrix such that a pellet forms which contains said binding matrix, and separating said pellet from the remainder of the sample.

9. The method of claim 1, wherein said sample comprises a cell lysate.

10. The method of claim 9, wherein said cell lysate comprises nonnucleic acid cellular debris, and wherein separating said RNA-bound binding matrix serves to remove a substantial proportion of said non-nucleic acid cellular debris from said initial sample.

11. The method of claim 1, wherein said binding matrix comprises a membrane coated with binding particles.

12. The method of claim 11, wherein said binding matrix comprises silicon.

13. The method of claim 1, wherein said binding matrix comprises pores, wherein said pores are about 3 Å to 100 Å in size.

14. The method of claim 1, wherein said dilution buffer has a pH of about 5.3 or less.

15. The method of claim 1, wherein said DNA molecules in said sample comprise genomic DNA molecules.

* * * * *

UNITED STATES PATENT AND TRADEMARK OFFICE
CERTIFICATE OF CORRECTION

PATENT NO. : 8,658,360 B2
APPLICATION NO. : 13/223904
DATED : February 25, 2014
INVENTOR(S) : Rex M. Bitner, Michelle M. Mandrekar and Paula R. Brisco It is certified that error appears in the above-identified patent and that said Letters Patent is hereby corrected as shown below:

Title page, inventors (75), second inventor, "Michelle M. Mandreker" should read --Michelle M. Mandrekar--.

Signed and Sealed this
Fifth Day of May, 2015

Michelle K. Lee
*Director of the United States Patent and Trademark Office*